(12) United States Patent
De Taboada et al.

(10) Patent No.: US 10,758,743 B2
(45) Date of Patent: Sep. 1, 2020

(54) METHOD FOR PROVIDING PHOTOTHERAPY TO THE BRAIN

(75) Inventors: Luis De Taboada, Carlsbad, CA (US); Jackson Streeter, Reno, NV (US)

(73) Assignee: Pthera LLC, Newark, DE (US)

(*) Notice: Subject to any disclaimer, the term of this patent is extended or adjusted under 35 U.S.C. 154(b) by 0 days.

(21) Appl. No.: 12/650,423

(22) Filed: Dec. 30, 2009

(65) Prior Publication Data
US 2010/0105977 A1   Apr. 29, 2010

Related U.S. Application Data

(63) Continuation of application No. 11/482,220, filed on Jul. 7, 2006, which is a continuation of application
(Continued)

(51) Int. Cl.
| | |
|---|---|
| *A61N 5/06* | (2006.01) |
| *A61N 7/00* | (2006.01) |
| *A61N 5/067* | (2006.01) |
| *A61N 5/00* | (2006.01) |
| *A61N 1/40* | (2006.01) |

(52) U.S. Cl.
CPC ......... *A61N 5/0613* (2013.01); *A61N 5/0622* (2013.01); *A61N 1/40* (2013.01); *A61N 5/0617* (2013.01); *A61N 7/00* (2013.01); *A61N 2005/007* (2013.01); *A61N 2005/067* (2013.01); *A61N 2005/0647* (2013.01); *A61N 2005/0652* (2013.01); *A61N 2005/0659* (2013.01)

(58) Field of Classification Search
CPC ................ A61N 5/0613; A61N 5/0622; A61N 2005/067; A61N 2005/0659; A61N 2005/0647; A61N 1/40; A61N 7/00; A61N 5/0617; A61N 2005/007
USPC .......................................... 607/88–94; 606/9
See application file for complete search history.

(56) References Cited

U.S. PATENT DOCUMENTS

| | | | |
|---|---|---|---|
| 1,856,969 A | 5/1932 | Reiter et al. | |
| 3,576,185 A | 4/1971 | Schulz et al. | |
(Continued)

FOREIGN PATENT DOCUMENTS

| | | |
|---|---|---|
| DE | 3200584 | 7/1983 |
| DE | 4108328 | 9/1992 |
(Continued)

OTHER PUBLICATIONS

US 6,344,051 B1, 02/2002, Dumoulin-White et al. (withdrawn)
(Continued)

*Primary Examiner* — Gary Jackson
*Assistant Examiner* — Sebastian X Lukjan
(74) *Attorney, Agent, or Firm* — Fish & Richardson P.C.

(57) ABSTRACT

A therapeutic treatment system and method are provided. The therapeutic system includes a light source adapted to irradiate at least a portion of the brain with light and a non-light energy source adapted to apply non-light energy to the at least a portion of the brain. The therapeutic treatment method includes irradiating at least a portion of a patient's brain with light and applying a non-light energy to the at least a portion of the patient's brain. The therapeutic treatment method provides therapeutic treatment without damaging the scalp tissue of the patient.

14 Claims, 17 Drawing Sheets

Related U.S. Application Data

No. 10/682,379, filed on Oct. 9, 2003, now Pat. No. 7,303,578, which is a continuation-in-part of application No. 10/287,432, filed on Nov. 1, 2002, now abandoned.

(60) Provisional application No. 60/442,693, filed on Jan. 24, 2003, provisional application No. 60/487,979, filed on Jul. 17, 2003, provisional application No. 60/502,147, filed on Sep. 11, 2003, provisional application No. 60/336,436, filed on Nov. 1, 2001, provisional application No. 60/369,260, filed on Apr. 2, 2002.

(56) References Cited

U.S. PATENT DOCUMENTS

| | | |
|---|---|---|
| 3,735,755 A | 5/1973 | Eggleton et al. |
| 3,810,367 A | 5/1974 | Peterson |
| 4,076,393 A | 2/1978 | Bates |
| 4,315,514 A | 2/1982 | Drewes et al. |
| 4,343,301 A | 6/1982 | Indech |
| 4,343,215 A | 8/1982 | Fuchs |
| 4,535,784 A | 8/1985 | Rholicek et al. |
| 4,539,987 A | 9/1985 | Nath et al. |
| 4,630,273 A | 12/1986 | Inoue et al. |
| 4,669,466 A | 6/1987 | L'Esperance |
| 4,671,285 A | 6/1987 | Walker |
| 4,686,986 A | 8/1987 | Fenyo et al. |
| 4,798,215 A | 1/1989 | Turner |
| 4,836,203 A | 6/1989 | MOiier et al. |
| 4,846,196 A | 7/1989 | Wiksell et al. |
| 4,850,351 A | 7/1989 | Herman et al. |
| 4,930,504 A | 6/1990 | Diamantopoulos et al. |
| 4,951,482 A | 8/1990 | Gilbert |
| 4,951,653 A | 8/1990 | Fry et al. |
| 4,966,144 A | 10/1990 | Rochkind et al. |
| 4,998,930 A | 3/1991 | Lundahl |
| 5,029,581 A | 7/1991 | Kaga et al. |
| 5,037,374 A | 8/1991 | Carol |
| 5,047,006 A | 9/1991 | Brandston et al. |
| 5,053,006 A | 10/1991 | Watson |
| 5,054,470 A | 10/1991 | Fry et al. |
| 5,125,925 A | 6/1992 | Lundahl |
| 5,150,704 A | 9/1992 | Tatebayashi et al. |
| 5,167,610 A | 12/1992 | Kitado et al. |
| 5,217,455 A | 6/1993 | Tan |
| 5,259,294 A | 11/1993 | May |
| 5,259,380 A | 11/1993 | Mendes et al. |
| 5,265,598 A | 11/1993 | Searfoss et al. |
| 5,267,294 A | 11/1993 | Kuroda et al. |
| 5,282,797 A | 2/1994 | Chess |
| 5,304,212 A | 4/1994 | Czeisler et al. |
| 5,344,434 A | 9/1994 | Talmore |
| 5,358,503 A | 10/1994 | Bertwell et al. |
| 5,368,555 A | 11/1994 | Sussman et al. |
| 5,401,270 A | 3/1995 | Muller et al. |
| 5,405,368 A | 4/1995 | Eckhouse |
| 5,464,436 A | 4/1995 | Smith |
| 5,441,495 A | 8/1995 | Liboff et al. |
| 5,445,146 A | 8/1995 | Bellinger |
| 5,445,608 A | 8/1995 | Chen et al. |
| 5,447,528 A | 9/1995 | Gerardo |
| 5,474,528 A | 12/1995 | Meserol |
| 5,500,009 A | 3/1996 | Mendes et al. |
| 5,501,655 A | 3/1996 | Rolt et al. |
| 5,503,637 A | 4/1996 | Kyricos et al. |
| 5,511,563 A | 4/1996 | Diamond |
| 5,540,727 A | 7/1996 | Tockman et al. |
| 5,540,737 A | 7/1996 | Fenn |
| 5,571,152 A | 11/1996 | Chen et al. |
| 5,580,550 A | 12/1996 | Gough et al. |
| 5,580,555 A | 12/1996 | Schwartz |
| 5,595,568 A | 1/1997 | Anderson et al. |
| 5,601,526 A | 2/1997 | Chapelon et al. |
| 5,616,140 A | 4/1997 | Prescott |
| 5,617,258 A | 4/1997 | Negus et al. |
| 5,621,091 A | 4/1997 | Kunkel et al. |
| 5,622,168 A | 4/1997 | Keusch et al. |
| 5,683,436 A | 4/1997 | Mendes et al. |
| 5,627,140 A | 5/1997 | Kopecky |
| 5,627,870 A | 5/1997 | Kopecky |
| 5,640,978 A | 6/1997 | Wong |
| 5,643,334 A | 7/1997 | Eckhouse et al. |
| 5,707,396 A | 1/1998 | Benabid |
| 5,709,645 A | 1/1998 | Siever |
| 5,720,894 A | 2/1998 | Neev et al. |
| 5,728,090 A | 3/1998 | Martin et al. |
| 5,735,844 A | 4/1998 | Anderson et al. |
| 5,755,752 A | 5/1998 | Segal |
| 5,762,867 A | 6/1998 | D'Silva |
| 5,766,233 A | 6/1998 | Thiberg |
| 5,769,878 A | 6/1998 | Kamei |
| 5,800,479 A | 9/1998 | Thiberg |
| 5,810,801 A | 9/1998 | Anderson et al. |
| 5,817,008 A | 10/1998 | Rafert et al. |
| 5,824,024 A | 10/1998 | Dial |
| 5,830,208 A | 11/1998 | Muller |
| 5,832,932 A | 11/1998 | Elsberry et al. |
| 5,842,477 A | 12/1998 | Naughton et al. |
| 5,843,073 A | 12/1998 | Sinofsky |
| 5,849,585 A | 12/1998 | Mather et al. |
| 5,871,521 A | 2/1999 | Kaneda et al. |
| 5,879,376 A | 3/1999 | Miller |
| 5,902,741 A | 5/1999 | Puchio et al. |
| 5,928,207 A | 7/1999 | Pisano et al. |
| 5,928,945 A | 7/1999 | Seliktar et al. |
| 5,951,596 A | 9/1999 | Bellinger |
| 5,954,762 A | 9/1999 | DiMino et al. |
| 5,958,761 A | 9/1999 | Yogev et al. |
| 5,983,141 A | 11/1999 | Sluijter et al. |
| 5,989,245 A | 11/1999 | Prescott |
| 5,993,442 A | 11/1999 | Omori |
| 6,015,404 A | 1/2000 | Altshuler et al. |
| 6,027,495 A | 2/2000 | Miller |
| 6,030,767 A | 2/2000 | Wagner et al. |
| RE36,634 E | 3/2000 | Ghaffari |
| 6,033,431 A | 3/2000 | Segal |
| 6,042,531 A * | 3/2000 | Holcomb .................. 600/13 |
| 6,045,575 A | 4/2000 | Rosen et al. |
| 6,046,046 A | 4/2000 | Hassanein |
| 6,056,575 A | 5/2000 | Sato et al. |
| 6,059,820 A | 5/2000 | Baronov |
| 6,060,306 A | 5/2000 | Flatt et al. |
| 6,063,108 A * | 5/2000 | Salansky .............. A61N 5/0616 606/13 |
| 6,074,411 A | 6/2000 | Lai et al. |
| 6,084,242 A | 6/2000 | Brown et al. |
| 6,100,290 A | 8/2000 | Levy et al. |
| 6,107,325 A | 8/2000 | Chan et al. |
| 6,107,608 A | 8/2000 | Hayes |
| 6,112,110 A | 8/2000 | Wilk |
| 6,117,128 A | 9/2000 | Gregory |
| 6,129,748 A | 10/2000 | Kamei |
| 6,143,878 A | 11/2000 | Koopman et al. |
| 6,146,410 A * | 11/2000 | Nagypal .............. A61N 5/0601 606/10 |
| 6,149,679 A | 11/2000 | DiMino et al. |
| 6,153,028 A | 11/2000 | Pleschiutschnigg et al. |
| 6,156,028 A | 12/2000 | Prescott |
| 6,161,048 A * | 12/2000 | Sluijter .............. A61N 1/36021 607/100 |
| 6,162,211 A | 12/2000 | Tankovich et al. |
| 6,179,771 B1 | 1/2001 | Mueller |
| 6,179,830 B1 | 1/2001 | Kokubu |
| 6,187,210 B1 | 2/2001 | Lebouitz et al. |
| 6,197,020 B1 | 3/2001 | O'Donnell, Jr. |
| 6,198,958 B1 | 3/2001 | Ives et al. |
| 6,210,317 B1 | 4/2001 | Bonlie |
| 6,210,425 B1 | 4/2001 | Chen |
| 6,213,998 B1 | 4/2001 | Shen et al. |
| 6,214,035 B1 | 4/2001 | Streeter |
| 6,221,095 B1 | 4/2001 | Van Zuylen et al. |
| 6,223,071 B1 | 4/2001 | Lundahl et al. |

(56) References Cited

U.S. PATENT DOCUMENTS

| | | | |
|---|---|---|---|
| 6,233,480 B1 | 5/2001 | Hochman et al. | |
| 6,235,015 B1 | 5/2001 | Mead et al. | |
| 6,238,424 B1 | 5/2001 | Thiberg | |
| 6,238,425 B1 | 5/2001 | Thiberg | |
| 6,253,097 B1 | 6/2001 | Aronow et al. | |
| 6,264,649 B1 | 7/2001 | Whitcroft et al. | |
| 6,267,779 B1 | 7/2001 | Gerdes | |
| 6,267,780 B1 | 7/2001 | Streeter | |
| 6,273,884 B1 | 8/2001 | Altshuler et al. | |
| 6,273,885 B1 | 8/2001 | Koop et al. | |
| 6,273,905 B1 | 8/2001 | Streeter | |
| 6,277,974 B1 | 8/2001 | Lo et al. | |
| 6,290,713 B1 | 9/2001 | Russel | |
| 6,290,714 B1 | 9/2001 | Streeter | |
| 6,306,130 B1 | 10/2001 | Anderson et al. | |
| 6,312,451 B1 | 11/2001 | Streeter | |
| 6,344,050 B1 | 2/2002 | Chen | |
| 6,358,272 B1 * | 3/2002 | Wilden | A61B 18/22 607/89 |
| 6,363,285 B1 | 3/2002 | Wey | |
| 6,364,907 B1 | 4/2002 | Obochi et al. | |
| 6,366,802 B1 | 4/2002 | Haber et al. | |
| 6,379,295 B1 | 4/2002 | Woo | |
| 6,379,376 B1 | 4/2002 | Lubart | |
| 6,379,939 B1 | 4/2002 | Lubart | |
| 6,391,023 B1 | 5/2002 | Weber et al. | |
| 6,395,016 B1 | 5/2002 | Oron et al. | |
| 6,397,107 B1 | 5/2002 | Lee et al. | |
| 6,402,678 B1 | 6/2002 | Fischell et al. | |
| 6,421,562 B1 | 7/2002 | Ross | |
| 6,432,101 B1 | 8/2002 | Weber et al. | |
| 6,433,872 B1 | 8/2002 | Nishi et al. | |
| 6,436,094 B1 | 8/2002 | Reuter | |
| 6,440,121 B1 | 8/2002 | Weber et al. | |
| 6,443,974 B1 | 9/2002 | Oron et al. | |
| 6,443,977 B1 | 9/2002 | Jaillet | |
| 6,443,978 B1 | 9/2002 | Zharov | |
| 6,447,537 B1 | 9/2002 | Hartman | |
| 6,449,466 B1 | 9/2002 | Jin et al. | |
| 6,454,789 B1 | 9/2002 | Chen et al. | |
| 6,458,120 B1 | 10/2002 | Shen et al. | |
| 6,471,716 B1 | 10/2002 | Pecukonis | |
| 6,494,900 B1 | 12/2002 | Salansky et al. | |
| 6,508,813 B1 | 1/2003 | Altshuler | |
| 6,511,475 B1 | 1/2003 | Altshuler et al. | |
| 6,511,485 B2 | 1/2003 | Hirt et al. | |
| 6,514,220 B2 | 2/2003 | Melton, Jr. et al. | |
| 6,530,920 B1 | 3/2003 | Whitcroft et al. | |
| 6,537,301 B1 | 3/2003 | Kamei | |
| 6,537,302 B1 | 3/2003 | Thiberg | |
| 6,537,304 B1 | 3/2003 | Oron | |
| 6,542,524 B2 | 4/2003 | Miyake | |
| 6,551,308 B1 * | 4/2003 | Muller et al. | 606/10 |
| 6,571,735 B1 | 6/2003 | Wilkinson | |
| 6,602,245 B1 | 8/2003 | Thiberg | |
| 6,602,274 B1 | 8/2003 | Chen | |
| 6,602,275 B1 | 8/2003 | Sullivan | |
| 6,632,219 B1 | 10/2003 | Baronov et al. | |
| 6,638,272 B2 | 10/2003 | Cho et al. | |
| 6,645,230 B2 | 11/2003 | Whitehurst | |
| 6,653,618 B2 | 11/2003 | Zenzie | |
| 6,663,620 B2 | 12/2003 | Altshuler et al. | |
| 6,663,659 B2 | 12/2003 | McDaniel | |
| 6,665,562 B2 | 12/2003 | Gluckman et al. | |
| 6,666,878 B2 | 12/2003 | Calgren | |
| 6,676,655 B2 | 1/2004 | McDaniel | |
| 6,679,877 B2 | 1/2004 | Ota et al. | |
| 6,685,702 B2 | 2/2004 | Quijano et al. | |
| 6,689,062 B1 | 2/2004 | Mesllum | |
| 6,692,486 B2 | 2/2004 | Jaafar et al. | |
| 6,692,517 B2 | 2/2004 | Cho et al. | |
| 6,702,837 B2 | 3/2004 | Gutwein | |
| 6,733,492 B2 | 5/2004 | Ota et al. | |
| 6,743,222 B2 | 6/2004 | Durkin et al. | |
| 6,746,473 B2 | 6/2004 | Shanks et al. | |
| 6,770,069 B1 | 8/2004 | Hobart et al. | |
| 6,800,086 B2 | 10/2004 | Strong | |
| 6,817,997 B2 | 11/2004 | Furuno et al. | |
| 6,832,111 B2 | 12/2004 | Tu et al. | |
| 6,866,678 B2 | 3/2005 | Shenderova et al. | |
| 6,872,221 B2 | 3/2005 | Lytle | |
| 6,878,144 B2 | 4/2005 | Altshuler et al. | |
| 6,896,693 B2 | 5/2005 | Sullivan | |
| 6,899,723 B2 | 5/2005 | Chen | |
| 6,902,563 B2 | 6/2005 | Wilkens et al. | |
| 6,918,922 B2 | 7/2005 | Oron | |
| 6,921,413 B2 | 7/2005 | Mahadevan-Jansen et al. | |
| 6,936,043 B2 | 8/2005 | Peyman | |
| 6,974,224 B2 | 12/2005 | Thomas-Benedict | |
| 6,974,450 B2 | 12/2005 | Weber et al. | |
| 6,974,451 B2 | 12/2005 | Altshuler et al. | |
| 6,976,985 B2 | 12/2005 | Altshuler et al. | |
| 7,037,326 B2 | 5/2006 | Lee | |
| 7,041,094 B2 | 5/2006 | Connors et al. | |
| 7,051,738 B2 | 5/2006 | Oron et al. | |
| 7,054,676 B2 | 5/2006 | Hedlund et al. | |
| 7,066,929 B1 * | 6/2006 | Azar et al. | 606/9 |
| 7,070,611 B2 | 7/2006 | Biel | |
| 7,077,840 B2 | 7/2006 | Altshuler et al. | |
| 7,081,128 B2 | 7/2006 | Hart et al. | |
| 7,083,610 B1 | 8/2006 | Murray et al. | |
| 7,100,615 B1 | 9/2006 | Kert | |
| 7,101,384 B2 | 9/2006 | Benedict | |
| 7,107,997 B1 | 9/2006 | Moses et al. | |
| 7,118,563 B2 | 10/2006 | Weckwerth et al. | |
| 7,127,266 B2 | 10/2006 | Martin et al. | |
| 7,139,612 B2 | 11/2006 | Chow et al. | |
| 7,150,710 B2 | 12/2006 | Haber et al. | |
| 7,217,266 B2 | 5/2007 | Anderson et al. | |
| 7,220,254 B2 | 5/2007 | Altshuler et al. | |
| 7,282,060 B2 | 10/2007 | Debenidictis et al. | |
| 7,288,108 B2 | 10/2007 | Dimauro et al. | |
| 7,309,348 B2 | 12/2007 | Streeter et al. | |
| 7,311,722 B2 | 12/2007 | Larsen | |
| 7,311,723 B2 | 12/2007 | Seibel et al. | |
| 7,344,555 B2 | 3/2008 | Anders et al. | |
| 7,351,252 B2 | 4/2008 | Altshuler et al. | |
| 7,351,253 B2 | 4/2008 | DiMauro et al. | |
| 7,389,776 B2 | 6/2008 | Maksimovich | |
| 7,402,167 B2 | 7/2008 | Nemenov et al. | |
| 7,412,141 B2 | 8/2008 | Gowda et al. | |
| 7,463,916 B2 | 12/2008 | Kawasaki et al. | |
| 7,534,255 B1 | 5/2009 | Streeter | |
| 7,559,945 B2 | 7/2009 | Breden et al. | |
| 7,575,589 B2 | 8/2009 | De Taboada et al. | |
| 7,695,504 B2 | 4/2010 | Anders et al. | |
| 7,744,590 B2 | 6/2010 | Eells et al. | |
| 8,167,921 B2 | 5/2012 | Streeter et al. | |
| 9,795,803 B2 | 10/2017 | Streeter et al. | |
| 9,993,659 B2 | 6/2018 | Streeter et al. | |
| 2001/0029391 A1 * | 10/2001 | Gluckman | A61N 1/36034 607/2 |
| 2001/0034478 A1 * | 10/2001 | Lambert | A61B 5/14532 600/318 |
| 2001/0044623 A1 | 11/2001 | Chen | |
| 2002/0018834 A1 | 2/2002 | Vaughan | |
| 2002/0068927 A1 | 6/2002 | Prescott | |
| 2002/0087205 A1 | 7/2002 | Chen | |
| 2002/0095197 A1 * | 7/2002 | Lardo | A61N 5/0601 607/89 |
| 2002/0099295 A1 | 7/2002 | Gil et al. | |
| 2002/0123781 A1 | 9/2002 | Shanks et al. | |
| 2002/0161418 A1 | 10/2002 | Wilkens et al. | |
| 2002/0177885 A1 | 11/2002 | Eisfield et al. | |
| 2002/0188334 A1 | 12/2002 | Calgren | |
| 2002/0198575 A1 | 12/2002 | Sullivan | |
| 2003/0004556 A1 | 1/2003 | McDaniel | |
| 2003/0021124 A1 | 1/2003 | Elbrecht et al. | |
| 2003/0023283 A1 * | 1/2003 | McDaniel | 607/88 |
| 2003/0087889 A1 | 5/2003 | Strong et al. | |
| 2003/0109906 A1 | 6/2003 | Streeter | |
| 2003/0114872 A1 * | 6/2003 | Mueller et al. | 606/167 |
| 2003/0122782 A1 | 7/2003 | Yamaguchi et al. | |
| 2003/0125782 A1 | 7/2003 | Streeter | |

(56) References Cited

U.S. PATENT DOCUMENTS

| | | |
|---|---|---|
| 2003/0125783 A1 | 7/2003 | Moran |
| 2003/0130709 A1 | 7/2003 | D.C. et al. |
| 2003/0137080 A1 | 7/2003 | Bouras et al. |
| 2003/0144712 A1 | 7/2003 | Streeter |
| 2003/0166156 A1* | 9/2003 | Sheppard ............ C07K 14/575 435/69.4 |
| 2003/0167080 A1* | 9/2003 | Hart .................... A61N 5/0616 607/88 |
| 2003/0181961 A1 | 9/2003 | Kamei |
| 2003/0181962 A1 | 9/2003 | Streeter |
| 2003/0209906 A1* | 11/2003 | McCurdy et al. ......... 285/382.7 |
| 2003/0212442 A1 | 11/2003 | Streeter |
| 2003/0216797 A1* | 11/2003 | Oron .............................. 607/89 |
| 2004/0010300 A1 | 1/2004 | Masotti et al. |
| 2004/0014199 A1 | 1/2004 | Streeter |
| 2004/0015214 A1 | 1/2004 | Simkin et al. |
| 2004/0030325 A1 | 2/2004 | Cahir et al. |
| 2004/0036975 A1 | 2/2004 | Slatkine |
| 2004/0044384 A1* | 3/2004 | Leber .................. A61N 5/0619 607/88 |
| 2004/0073278 A1 | 4/2004 | Pachys |
| 2004/0082862 A1 | 4/2004 | Chance |
| 2004/0093042 A1 | 5/2004 | Altshuler et al. |
| 2004/0111132 A1 | 6/2004 | Shenderova et al. |
| 2004/0116909 A1 | 6/2004 | Neuberger et al. |
| 2004/0122491 A1 | 6/2004 | Strong |
| 2004/0132002 A1 | 7/2004 | Streeter |
| 2004/0138727 A1 | 7/2004 | Taboada et al. |
| 2004/0153130 A1 | 8/2004 | Oron et al. |
| 2004/0153131 A1 | 8/2004 | Yorke |
| 2004/0158300 A1 | 8/2004 | Gardiner |
| 2004/0162596 A1 | 8/2004 | Alshuler et al. |
| 2004/0220513 A1 | 11/2004 | Streeter |
| 2004/0236226 A1 | 11/2004 | Maki et al. |
| 2004/0260367 A1 | 12/2004 | De Taboada et al. |
| 2005/0005626 A1 | 1/2005 | McMahon |
| 2005/0009161 A1 | 1/2005 | Streeter |
| 2005/0015122 A1 | 1/2005 | Mott et al. |
| 2005/0024853 A1 | 2/2005 | Thomas-Benedict |
| 2005/0049452 A1* | 3/2005 | Lawlis .................. A61M 21/00 600/28 |
| 2005/0060012 A1* | 3/2005 | Voorhees .................. A61F 7/02 607/96 |
| 2005/0070518 A1 | 3/2005 | Strong |
| 2005/0107851 A1 | 5/2005 | Taboada et al. |
| 2005/0143792 A1 | 6/2005 | Jay |
| 2005/0159793 A1 | 7/2005 | Streeter |
| 2005/0187595 A1 | 8/2005 | Streeter |
| 2005/0203504 A1* | 9/2005 | Wham ............... A61B 18/1442 606/34 |
| 2005/0203595 A1 | 9/2005 | Oron |
| 2005/0216072 A1 | 9/2005 | Mahadevan-Jansen et al. |
| 2006/0155348 A1 | 7/2006 | deCharms |
| 2006/0167532 A1 | 7/2006 | Parker |
| 2006/0184214 A1 | 8/2006 | McDaniel |
| 2006/0223155 A1 | 10/2006 | Streeter |
| 2006/0253177 A1 | 11/2006 | De Taboada et al. |
| 2007/0066996 A1* | 3/2007 | Katzman et al. .................. 607/3 |
| 2007/0114872 A1 | 5/2007 | Han |
| 2007/0129778 A1 | 6/2007 | Dougal |
| 2007/0162093 A1 | 7/2007 | Porter et al. |
| 2007/0179570 A1 | 8/2007 | De Taboada et al. |
| 2007/0179571 A1 | 8/2007 | De Taboada et al. |
| 2007/0219605 A1 | 9/2007 | Yaroslavsky et al. |
| 2007/0239235 A1 | 10/2007 | DiMauro et al. |
| 2007/0260295 A1 | 11/2007 | Chen et al. |
| 2007/0288072 A1 | 12/2007 | Pascual-Leone et al. |
| 2008/0004565 A1 | 1/2008 | Streeter et al. |
| 2008/0033412 A1 | 2/2008 | Whelan et al. |
| 2008/0033513 A1 | 2/2008 | Man et al. |
| 2008/0051858 A1 | 2/2008 | Haber et al. |
| 2008/0070229 A1 | 3/2008 | Streeter |
| 2008/0077199 A1 | 3/2008 | Shefi et al. |
| 2008/0103562 A1 | 5/2008 | Anders et al. |
| 2008/0114419 A1 | 5/2008 | Crowley |
| 2008/0125836 A1 | 5/2008 | Streeter et al. |
| 2008/0139941 A1 | 6/2008 | Njemanze |
| 2008/0140164 A1 | 6/2008 | Oberreiter et al. |
| 2008/0221630 A1 | 9/2008 | Palti |
| 2008/0221211 A1 | 11/2008 | Streeter |
| 2008/0287930 A1 | 11/2008 | Rapoport |
| 2008/0312715 A1 | 12/2008 | Asirvatham et al. |
| 2009/0054955 A1 | 2/2009 | Kopell et al. |
| 2009/0088680 A1 | 4/2009 | Asirvatham et al. |
| 2009/0112280 A1 | 4/2009 | Wingeier et al. |
| 2009/0163982 A1 | 6/2009 | deCharms |
| 2009/0216301 A1 | 8/2009 | Streeter et al. |
| 2009/0222067 A1 | 9/2009 | Toselli et al. |
| 2009/0254068 A1 | 10/2009 | Karni et al. |
| 2009/0254154 A1 | 10/2009 | De Taboada et al. |
| 2009/0270776 A1 | 10/2009 | Chang |
| 2010/0010592 A1 | 1/2010 | De Taboada et al. |
| 2010/0010594 A1 | 1/2010 | De Taboada |
| 2010/0016841 A1 | 1/2010 | De Taboada |
| 2010/0055074 A1 | 3/2010 | Romanczyk et al. |
| 2010/0067128 A1 | 3/2010 | Delapp |
| 2010/0152820 A1 | 6/2010 | Anders et al. |
| 2010/0161017 A1 | 6/2010 | Choi et al. |
| 2010/0204762 A1 | 8/2010 | De Taboada et al. |
| 2010/0211136 A1 | 8/2010 | De Taboada et al. |
| 2011/0060266 A1 | 3/2011 | Streeter et al. |
| 2011/0102916 A1 | 5/2011 | Delapp et al. |
| 2011/0144723 A1 | 6/2011 | Streeter et al. |

FOREIGN PATENT DOCUMENTS

| | | |
|---|---|---|
| DE | 4213053 | 10/1993 |
| DE | 29515096 | 1/1996 |
| EP | 0130950 | 4/1990 |
| EP | 0763371 | 3/1997 |
| EP | 0783904 | 7/1997 |
| EP | 0827716 | 3/1998 |
| EP | 1074275 | 2/2001 |
| EP | 1226787 | 7/2002 |
| EP | 2 082 696 | 7/2009 |
| JP | H0423634 | 2/1992 |
| WO | WO199203964 | 3/1992 |
| WO | WO199636397 | 11/1996 |
| WO | WO199636396 | 1/1997 |
| WO | WO199804321 | 2/1998 |
| WO | WO199822573 | 5/1998 |
| WO | WO199833556 | 8/1998 |
| WO | WO199942178 | 8/1999 |
| WO | WO1999042178 | 8/1999 |
| WO | WO199946005 | 9/1999 |
| WO | WO199962599 | 12/1999 |
| WO | WO 00/25684 | 5/2000 |
| WO | WO200033534 | 6/2000 |
| WO | WO200035534 | 6/2000 |
| WO | WO200100271 | 1/2001 |
| WO | WO2002055149 | 7/2002 |
| WO | WO2002064084 | 8/2002 |
| WO | WO2002092509 | 11/2002 |
| WO | WO2002098509 | 12/2002 |
| WO | WO2003042376 | 5/2003 |
| WO | WO2003060399 | 7/2003 |
| WO | WO2004022154 | 3/2004 |
| WO | WO2005025672 | 3/2005 |
| WO | WO2005092440 | 10/2005 |
| WO | WO2005118067 | 12/2005 |
| WO | WO2006105254 | 10/2006 |
| WO | WO 06/115761 | 11/2006 |
| WO | WO2006138659 | 12/2006 |
| WO | WO2007087438 | 8/2007 |
| WO | WO2007089615 | 8/2007 |
| WO | WO2007089744 | 8/2007 |
| WO | WO 08/049905 | 5/2008 |
| WO | WO2008054812 | 5/2008 |
| WO | WO2008141296 | 11/2008 |
| WO | WO2009067323 | 7/2009 |
| WO | WO2009117323 | 9/2009 |

(56) References Cited

FOREIGN PATENT DOCUMENTS

| WO | WO2010009452 | 1/2010 |
|---|---|---|
| WO | WO2010031777 | 3/2010 |

OTHER PUBLICATIONS

"Is Laser Therapy Overtaking Ultrasound?" http://www.laser.uk.com/laserTherapy vs. ultrasound.html, dated Feb. 20, 1999.
"Is LLLT Different from Ultrasound?" http://www.thorlaser.com/LLLT/is-LLLT-diff-from-ultrasound.htm, 2 pages.
"Laser Exposure Limits & Hazard Calculations," Excerpts from OSHA Technical Manual, Chapter 6: Laser Hazards, date unknown.
Adamic et al., "Vascular lasers and IPLS: Guidelines for care from the European Society for Laser Dermatology (ESLD)," Journal of cosmetic and laser therapy, Jan. 1, 2007, 9(2):113-124.
Albertini et al., "COX-2 mRNA expression decreases in the subplantar muscle of rat paw subjected to carrageenan-induced inflammation after low level laser therapy," Inflammation Research Jun. 1, 2007, 56(6):228-9.
Alerstam et al., "Parallel computing with graphics processing units for high-speed Monte Carlo simulation of photon migration," Journal of Biomedic Optics, Nov. 2008, 13(6):060504.
Alexander, "Biology of Parkinson's disease—pathogenesis and pathophysiology of a multisystem neurodegenerative disorder", Dialogues Clin Neurosci, Sep. 2004, 6(3):259-344.
Alton et al., "Gene Therapy: The Case for Cystic Fibrosis," J.R. Soc. Med, Dec. 1997, 90(31_suppl):43-46.
Amat et al., "Modification of the intrinsic fluorescence and the biochemical behavior of ATP after irradiation with visible and near-infrared laser light," Journal of Photochemistry and Photobiology B: Biology Oct. 3, 2005 81(1):26-32.
Anders, "The Potential of Light Therapy for Central Nervous System Injury and Disease," Photomedicine and Laser Surgery, Jul. 2009 27(3):379-380.
Arthur, "Parkinson's Disease Brain Mitochondria Have Impaired Respirasome Assembly, Age-Related Increases in Distribution of Oxidative Damage to mtDNA and No Differences in Heteroplasmic mtDNA Mutation Abundance," Molecular Degeneration, Sep. 2009, 13 pages.
Atamna et al., "Mechanisms of mitochondrial dysfunction and energy deficiency in Alzheimer's disease," Mitochondrion Sep. 1, 2007, 7(5):297-310.
Avni et al., "Protection of Skeletal Muscles from Ischemic Injury: Low-Level Laser Therapy Increases Antioxidant Activity", Photomedicine and Laser Surgery, Jun. 1, 2005, 23(3):273-277.
Bashkatov et al., "Estimate of the melanin content in human hairs by the inverse Monte-Carlo method using a system for digital image analysis," Quantum Electronics, 2006, 36(12) 1111-1118.
Baxter "Laser Safety Training Manual," University of Chicago Chemistry Department, date unknown.
Ben-Shachar et al., "Neuroanatomical Pattern of Mitochondrial Complex I Pathology Varies between Schizophrenia, Bipolar Disorder and Major Depression," PLoS One, Nov. 2008, 3(11):e3676, 13 pages.
Bisland et al., "To begin at the beginning: The science of biostimulation in cells and tissues," Proc. of SPIE, Feb. 28, 2006, 6140:612004, 10 pages.
Boelens et al., "An EPR study of the photodissociation reactions of oxidised cytochrome c oxidase-nitric oxide complexes." Biochimica et Biophysica Acta (BBA)-Bioenergetics, Aug. 31, 1983, 31; 724(2):176-83.
Boucher, "Current Status of CF Gene Therapy," Trends in Genetics, Mar. 1, 1996, 12(3):81-84.
Boucher, "Status of Gene Therapy for Cystic Fibrosis Lung Disease," J. Clin. Invest, Feb. 15, 1999, 103(4):441-455.
Brennan et al., "NADPH oxidase is the primary source of superoxide induced by NMDA receptor activation," Nature Neuroscience, Jul. 2009, 12(7):857-864.
Brown, "Mechanisms of inflammatory neurodegeneration: iNOS and NADPH oxidase," Biochemical Society Transactions, 2007, 35(5):1119-1121.
Buckman et al., "Spontaneous Changes in Mitochondrial Membrane Potential in Cultured Neurons," The Journal of Neuroscience, Jul. 15, 2001, 21(14):5054-5065.
Calabrese et al., "Nitric oxide in the central nervous system: neuroprotection versus neurotoxicity," Nature Reviews: Neuroscience, Oct. 2007, 8:766-775.
Carroll et al, "Red Blood Cell Stimulation of Platelet Nitric Oxide Production Indicated by Quantitative Monitoring of the Communication between Cells in the Bloodstream," Analytical Chemistry, Jul. 15, 2007, 79(14):5133-5138.
Carroll, "A 3D dose model for low level laser/led therapy biostimulation and bioinhibition," Proc. of SPIE, Feb. 12, 2008, 6846:684603, 3 pages.
Castello et al., "Oxygen-regulated isoforms of cytochrome c oxidase have differential effects on its nitric oxide production and on hypoxic signaling," PNAS Early Edition, www.pnas.org/cgi/doi/10.1073/pnas.0709461105, 2008, 6 pages.
Catanzaro et al. "Managing Tissue Heating in Laser Therapy to Enable Double-Blind Clinical Study," Proc. SPIE, vol. 6140, 614000 (2006).
Celsi et al., "Mitochondria, calcium and cell death: A deadly triad in neurodegeneration," Biochim. Biophys. Acta., May 2009; 1787(5):335-344.
Chan et al., "Rejuvenation protects neurons in mouse models of Parkinson's disease," Nature, vol. 447, Jun. 28, 2007.
Chance, "The stopped-flow method and chemical intermediates in enzyme reactions—a personal essay," Personal perspective, Photosynthesis Research 2004, 80:387-400.
Chen et al., "Low Level Laser Therapy activates NF-kB via Generation of Reactive Oxygen Species in Mouse Embryonic Fibroblasts," Proc. of SPIE, vol. 7165, Feb. 2009.
Chow et al., "830nnn laser irradiation induces varicosity formation, reduces mitochondrial membrane potential and blocks fast axonal flow in small and medium diameter rat dorsal root ganglion neurons: implications for the analgesic effect of 830nm laser," Journal of the Peripheral Nervous System, 12:28-39 (2007).
Custo et al., "Comparison of Diffusion and Transport in human head," Biomedical Topical Meeting Apr. 14, 2004 (p. WF31). Optical Society of America.
Custo et al., "Effective scattering coefficient of the cerebral spinal fluid in adult head models for diffuse optical imaging," Applied Optics, Jul. 1, 2006, 45(19):4747-4756.
Davies et al., "Prospects for Gene Therapy for Cystic Fibrosis," Mol. Med Today 4(7):292-299, Jul. 1998.
Dawson et al., "Adverse Events Associated With Nonablative Cutaneous Laser, Radiofrequency, and Light-Based Devices," Seminars in Cutaneous Medicine and Surgery, 2007, pp. 15-21.
De Groot et al., "Bijwerkingen van Lasertherapie," Nederlands Tijdschrift voor Dermatologie & Venereologie, vol. 16, Sep. 2006 (In Dutch).
Delori et al., "Maximum permissible exposures for ocular safety (ANSI 2000), with emphasis on ophthalmic devices," J. Opt. Soc. Am. A., May 2007, 24(5):1250-1265.
Demaurex et al., "Reactive oxygen species are NOXious for neurons," Nature Neuroscience, Jul. 2009, 12(7):819-820.
Desmet et al, "Clinical and Experimental Applications of NIR-LED Photobiomodulation" Photomedicine and Laser Surgery-2006;24(2):121-128.
DeTaboada et al.: "Transcranial Application of Low-Energy Laser Irradiation Improves Neurological Deficits in Rats Following Acute Stroke", Lasers in Surgery and Medicine 38:70-73 (2006).
Dhar et al., "Chromosome Conformation Capture of all 13 Genomic Loci in the Transcriptional Regulation of the Multi-subunit Bigenomic Cytochrome C Oxidase in Neurons," The Journal of Biological Chemistry. 2009.
EPO Extended Search Report re Appl. No. 10182415.9, dated Nov. 26, 2010.
Ferrari et al., "Barriers to and New Approaches for Gene Therapy and Gene Delivery in Cystic Fibrosis," Adv. Drug Del. Rev 54(11):1373-1393, 2002.

(56) References Cited

OTHER PUBLICATIONS

Franceschini et al., "Near-infrared absorption and scattering spectra of tissues in vivo." Optical Tomography and Spectroscopy of Tissue III Jul. 15, 1999, 3597:526-532 International Society for Optics and Photonics.
Frigo et al., "The effect of low-level laser irradiation (Ga—Al—AsP—660nm) on in vitro and in vivo melanoma," BMC Cancer, Nov. 20, 2009, 8 pages.
Galuzzi et al., "Targeting post-mitochondrial effectors of apoptosis for neuroprotection," Biochim. Biophys. Acta., 2009, 402-413.
Gao & Xing., "Molecular mechanisms of cell proliferation induced by low power laser irradiation," Journal of Biomedical Science, 2009, 16:4, 16 pages.
Giuliani et al., "Low infra red laser light irradiation on cultured neural cells: effects on mitochondria and cell viability after oxidative stress," BMC Complementary and Alternative Medicine 2009, 9:8.
Goldstein et al., "Patient Safety in Trials of Therapy for Acute Ischemic Stroke," The Journal of the American Medical Association, vol. 287, No. 8, Feb. 27, 2002, 42 pages.
Gourley et al., "Optical Phenotyping of Human Mitochondria in a Biocavity Laser," IEEE Journal of Selected Topics in Quantum Electronics, vol. 11, No. 4, Jul./Aug. 2005, 14 pages.
Haitsma et al., "Monitoring cerebral oxygenation in traumatic brain injury," Progress in Brain Research, vol. 161, Chapter 14, pp. 207-216, 2007.
Han et al., "Proteonnic analysis of active multiple sclerosis lesions reveals therapeutic targets," Nature Feb. 2008, 451:1076-1081.
Hancock et al., "Modulation of Pain in Osteoarthritis: The Role of Nitric Oxide," Clin. J. Pain, vol. 24, No. 4, May 2008, pp. 353-365.
Hausser et al., "Controlling neural circuits with light," Nature: News & Views, vol. 446, Apr. 5, 2007, pp. 617-619.
Hawkins et al., "How Long After Laser Irradiation Should Cellular Responses be Measured to Determine the Laser Effects?" Journal of Laser Applications, vol. 19, No. 2, May 2007, pp. 74-83.
Hawkins-Evans et al., "Effect of Wavelength and Fluence on Morphology, Cellular and Genetic Integrity of Diabetic Wounded Human Skin Fibroblasts," Proc. of SPIE vol. 6140, p. 614006-1 to 614006-13 (2006).
Hawkins-Evans, Denise et al., "Efficacy of a single high does versus multiple low doses of LLLT on wounded skin fibroblasts," Proc. of SPIE vol. 6632, p. 66321U-1 to 66321U-12 (2007).
Henchcliffe et al., "Mitochondrial biology and oxidative stress in Parkinson disease pathogenesis," Nature Clinical Practice Neurology, 4(11):600-609, Nov. 2008.
Hilf, "Mitochondria are targets of photodynamic therapy," J. Bioenerg. Biomembr. (2007) 39:85-89.
Hollenbeck, "The Pattern and Mechanism of Mitochondrial Transport in Axons," Frontiers in Bioscience 1, Jul. 1, 1996.
Hori et al., "Automatic characterization and segmentation of human skin using three-dimensional optical coherence tomography," Optics Express, Mar. 6, 2006, 14(5):1862-1877.
Hu et al., "Helium-Neon Laser Irradiation Stimulates Cell Proliferation through Photostimulatory Effects in Mitochondria," Journal of Investigative Dermatology, Aug. 1, 2007, 127(8):2048-2057.
Huttemann et al., "Regulation of oxidative phosphorylation, the mitochondrial membrane potential, and their role in human disease," J. Bioenerg. Biomembr (2008) 40:445-456, pp. 445-456.
Ilic, S., et al.: "Effects of Power Densities, Continuous and Pulse Frequencies, and Number of Sessions of Low-Level Laser Therapy on Intact Rat Brain" Photomedicine and Laser Surgery-2006; 24(4):458-466.
International Preliminary Report on Patentability in International Application No. PCT/US2007/002219, dated May 2, 1998.
International Preliminary Report on Patentability in International Application No. PCT/US2007/002474, dated Apr. 16, 2008.
International Preliminary Report on Patentability in International Application No. PCT/US2004/029724, dated Mar. 13, 2006, 7 pages.
International Search Report in International Application No. PCT/CA99/00156, dated Jun. 11, 1999 in 3 pages.
International Search Report in International Application No. PCT/US02/36808, dated Apr. 2, 2003 in 3 pages.
International Search Report in International Application No. PCT/US03/00747, dated May 23, 2003 in 4 pages.
International Search Report in International Application No. PCT/US04/029724, dated Jan. 7, 2005 in 3 pages.
Izzetoglu et al., "Functional Brain Imaging Using Near-Infrared Technology, Assessing Cognitive Activity in Real-Life Situations" IEEE Engineering in Medicine and Biology Magazine, Jul./Aug. 2007, p. 38-46.
Jacques et al., "Tutorial on diffuse light transport," Journal of Biomedical Optics, Jul./Aug. 2008, 13(4):041302.
Jekabsone et al., "Nitric oxide from neuronal nitric oxide synthase sensitises neurons to hypoxia-induced death via competitive inhibition of cytochrome oxidase," Journal of Neurochemistry, Oct. 2007, 103(1):346-56.
Jou et al., "Mitochondrial Dysfunction and Psychiatric Disorders," Chang Gung Med. J., Jul.-Aug. 2009, 32(4):370-379.
Kahn et al., "Low Intensity Laser Therapy: The clinical approach," Proc. of SPIE, vol. 6140, 2008.
Karu et al., "Cellular Effects of Low Power Laser Therapy Can be Mediated by Nitric Oxide," Lasers in Surgery and Medicine, 36:307-314 (2005).
Karu et al., "Effects of Low-Power Light on Biological Systems V", Jul. 7, 2000, pp. 1-17.
Karu, "Mitochondrial Signaling in Mammalian Cells Activated by Red and Near-IR Radiation," Photochemistry and Photobiology, 2008, 84:1091-1099.
Karu: "Mechanisms of Low-Power Laser Light Action on Cellular Level", Proceedings of SPIE, vol. 4159, 2000.
Kiguchi, Masashi et al., "Comparison of light intensity on the brain surface due to laser exposure during optical topography and solar irradiation," Journal of Biomedical Optics 12(6), Nov./Dec. 2007.
Kim et al., "Ultrafast Laser Radiation and Conduction Heat Transfer in Biological Tissues," Proceedings of IMECE2005, 2005 ASME International Mechanical Engineering Congress and Exposition, Nov. 5-11, 2005.
Kofke et al., "Near Infrared Laser Therapy," University of Pennsylvania, 2009.
Lampl, "Laser treatment for stroke," Expert Rev. Neurotherapeutics, Aug. 1, 2007, 7(8):961-5.
Lane, "Cell Biology: Power Games" Nature 443:901-903, Oct. 26, 2006.
Lapchak et al., "Advances in ischemic stroke treatment: neuroprotective and combination therapies," Expert Opin. Emerging Drugs, Mar. 2007, 12(1):97-112.
Lapchak et al., "Safety Profile of Transcranial Near-Infrared Laser Therapy Administered in Combination with Thrombolytic Therapy to Embolized Rabbits," Stroke, Nov. 2008.
Lapchak, "Transcranial Near-Infrared Laser Therapy Improves Behavior and Differentially Regulates the Expression of Rapid Response Elements (Genes) in Rabbits Following Embolic Strokes," Stroke 2009; 40; e214; Abstracts From the 2009 International Stroke Conference.
Li, "Managing nonlinearity in optical fiber for high-power lasers," The International Society for Optical Engineering, SPIE Newsroom, 2006.
Liang et al., "Near-Infrared Light Via Light-Emitting Diode Treatment is Therapeutic Against Rotenone- and 1-Methyl-4-Phenylpyridinium Ion-Induced Neurotoxicity," Neuroscience 153 (2008) 936-974.
Liang, et al., "Photobimodulation Partially Rescues Visual Cortical Neurons from Cyanide-Induced Apoptosis" Neuroscience 2006;139: 639-649.
Liesz et al., "Regulatory T cells are key cerebroprotective immunomodulators in acute experimental stroke," Nature Medicine, Jan. 25, 2009, 15(2):192.
Lohr et al., "Enhancement of nitric oxide release from nitrosyl hemoglobin and nitrosyl myoglobin by red/near infrared radiation: Potential role in cardioprotection," Journal of Molecular and Cellular Cardiology 47 (2009) 256-263.

(56) References Cited

OTHER PUBLICATIONS

Longo et al., "Annyotrophinc Lateral Sclerosis (ALS) treated with Low Level LASER Therapy (LLLT): a case report," Laser Florence 2008, A Bridge to the Laser Mediciane World, p. 96-98.
Lopes-Martins et al., "Steroids block the anti-inflammatory effects of low level laser therapy." Mechanisms for Low-Light Therapy Feb. 28, 2006 (vol. 5140, p. 61400D). International Society for Optics and Photonics. 6 pages.
Lubart et al., "Broadband Visible Light Induced NO Formation," 2009, http://proceedings.aip.org/proceedings/cpcr.jsp, 4 pages.
Lubart et al., "Low-Energy Laser Irradiation Promotes Cellular Redox Activity," Photomedicine and Laser Surgery, vol. 23, No. 1, 2005, pp. 3-9.
Lue et al, "Membranotropic photobiomodulation on red blood cell deformability," Proc. of SPIE, vol. 6534, 2007.
Lychagov et al. "Experimental study of NIRtransmittance of the human skull," Proc. of SPIEvol. 6085, 2006 (five pages).
Macklis, "Transplanted Neocrotical Neurons Migrate Selectively into Regions of Neuronal Degeneration Produced by Chromophore-targeted Laser Photolysis," The Journal of Neuroscience, Sep. 1993, 13(9); 3848-3863.
Manczak et al., "Mitochondria are a direct site of AB accumulation in Alzheimer's disease neurons: implications for free radical generation and oxidative damage in disease progression," Human Molecular Genetics, Mar. 21, 2006, 15(9):1437-1449.
Marshall, "Hope after failure in clinical trials," BusinessScan, BioPhotonics, Apr. 2009, 2 pages.
Martin, "Light Activated Tissue Regeneration and Therapy," Notes, Aug. 2004.
Mason, et al., "Nitric oxide inhibition of respiration involves both competitive (heme) and noncompetitive (copper) binding to cytochrome c oxidase," PNAS, vol. 103, pp. 708-713, Jan. 9, 2006.
McClelland et al., "Neurologic Correlates of Infarction-Like Lesion Location on Magnetic Resonance Imaging in the Cardiovascular Health Study," Journal of Stroke and Cerebrovascular Disease, Sep. 1, 2000, 9(5):218-28.
McKinlay et al., "Biological Bases of Maximum Permissible Exposure Levels of Laser Standards," J. Soc. Radiol. Prol. 4(1):25-33 1984.
Meguro et al., "Caspase Inhibitors Attenuate Oxyhemoglobin-Induced Apoptosis in Endothelial Cells," Stroke, 2001; 32; 561-566.
Mester et al., "The Biomedical Effects of Laser Application," Lasers in Surgery and Medicine, 5:31-39 (1985).
Mohanty et al., "Generation of ROS in cells on exposure to CW and pulsed near-infrared laser tweezers," Photochemical & Photobiological Sciences, 2006, pp. 134-139.
Molinaro, "Light/Tissue Interaction IST 8A," Lecture #5, Jan. 23, 2006.
Moncada et al., "Nitric oxide, cell bioenergetics and neurodegeneration," Journal of Neurochemistry, 2006, 97, pp. 1676-1689.
Moriyama et al., "In Vivo Study of the Inflammatory Modulating Effects of Low-level Laser Therapy on iNOS Expression Using Bioluminescence Imaging," Photochemistry and Photobiology, 2005, 81:1351-1355.
Moser et al., "Darwin at the molecular scale: selection and variance in electron tunneling proteins including cytochrome c oxidase," Philosophical Transactions of the Royal Society B, 2006, 361:1295-1305.
Mthunzi et al., "Influence of Beam Shape on in-vitro Cellular Transformations in Human Skin Fibroblasts," Proc. of SPIE, vol. 5876, 2005.
Mudra et al., "Analysis of near-infrared spectroscopy and indocyanine green dye dilution with Monte Carlo simulation of light propagation in the adult brain," Journal of Biomedical Optics, 11(4):1-14, Jul./Aug. 2006.
Myers et al., "Proposed Reference Spectral Irradiance Standards to Improve Concentrating Photovoltaic System Design and Performance Evaluation," National Renewable Energy Laboratory, May 2002, 7 pages.
Naviaux, "Mitochondria-Light Interactions" "Mechanisms of Cell Sparing and Regeneration," The Mitochondrial and Metabolic Disease Center, 2007, 30 pages.
Ng, "Non-Ionizing Radiations" "Sources, Biological Effects, Emissions and Exposures," Proceedings of the International Conference on Non-Ionizing Radiation at UNITEN, Electromagnetic Fields and Our Health, Oct. 20-22, 2003, 16 pages.
Oron et al., "Low-Level Laser Therapy Applied Transcranially to Rats After Induction of Stroke Significantly Reduces Long-Term Neurological Deficits," Stroke, 2006; 37:2620-2624.
Osipov, A.N. et al., "Biological Activity of Hemoprotein Nitrosyl Complexes," Biochemistry, 2007, 72(13):1491-1504.
Palacios-Callender et al., "Cytochrome c-oxidase regulates endogenous nitric oxide availability in respiring cells: A possible explanation for hypoxic vasodilation," PNAS, Nov. 20, 2007, 104(47):18508-18513.
Parathath et al., "Nitric Oxide Synthase Isoforms Undertake Unique Roles During Excitotoxicity," Stroke Apr. 19, 2007, 38:1938-1945.
Parihar, "Mitoenergetic failure in Alzheimer disease," Am J Physiol Cell Physiol, Jun. 28, 2006, 292:C8-C23.
Partial International Search Report for PCT/US05/004873, dated Sep. 5, 2005.
Pislea et al., "Low Level Long Wavelength Laser Irradiation Effects on Cells Cycle Progression and Apoptosis of Energy Restricted Jurkat T-Cells," Romanian J. Biophys., 19(1):1-18, 2009.
Pogue et al., "Transient absorption changes in vivo during photodynamic therapy with pulsed-laser light," British Journal of Cancer (1999) 80(3/4):344-351.
Popp, "On the Coherence of Ultraweak Photon Emission from Living Tissues," Disequilibrium and Self-Organisation, pp. 207-230, 1986.
Powers et al., "Cerebral mitochondrial metabolism in early Parkinson's disease," Journal of Cerebral Blood Flow & Metabolism, Oct. 2008, 28:1754-1760.
Ratner, "The Alzheimer's Divide," In Vivo, Sep. 2008.
Rohn et al., "Caspases as Therapeutic Targets in Alzheimer's Disease: Is it Time to "Cut" to the Chase?" Int J Clin Exp Pathol, 2009, 2(2):108-118.
Romano et al., "Latest Developments in Gene Transfer Technology: Achievements, Perspectives, and Controversies over Therapeutic Applications," Stem Cells, Jan. 1, 2000 18(1):19-39.
Rose et al., "Mode Field Pertubations and Numerical Aperture Broadening Due to Angular Misalignment in Multimode Fiber Coupling," Proc. of SPIE, vol. 7173, 2009, 9 pages.
Rosenecker et al., "Towards Gene Therapy of Cystic Fibrosis," Eur. J. Med. 23(3): 149-156, Mar. 1998.
Rosenfeld, et al., "Gene therapy for cystic fibrosis," Chest, Jan. 1, 1996, 109(1):241-252.
Sarasa et al., "Natural Non-Transgenic Animal Models for Research in Alzheimer's Disease," Current Alzheimer's Research, Apr. 1, 2009, 6(2):171-178.
Schaffer et al., "Two-Photon Imaging of Cortical Surface Microvessels Reveals a Robust Redistribution in Blood Flow after Vascular Occlusion," PLOS Biology, Feb. 2006, vol. 4, Issue 2, pp. 0258-0270.
Schumm, "Laser blood irradiation for multiple sclerosis: a new treatment procedure with significant improvement of the quality of life," Komplementäre and Integrative Medizin Nov./Dec. 2008, 49(11-12):38-43.
Seremet et al., "Photobiomodulation of Quercetin Antiproliferative Effects Seen in Human Acute Leukemia Jurkat Cells,"Romanian J. Biophys., 17(1):33-43, 2007.
Sharpe, "Interaction of Peroxynitrite with Mitochondrial Cytochrome Oxidase," The Journal of Biological Chemistry, Nov. 20, 1998, 273(47):30961-30972.
Shichita et al., "Pivotal role of cerebral interleukin-17-producing yÅ T cells in the delayed phase of ischemic brain injury," Nature Medicine, Aug. 2009, 15(8):946-951.
Shimada et al., "Intracellular disruption of mitochondria in a living HeLa cell with 76-MHz femtosecond laser oscillator," Optics Express, Nov. 28, 2005, 13(24):9869-9880.

(56) References Cited

OTHER PUBLICATIONS

Shiva, "Shining a light on tissue NO stores: Near infrared release of NO from nitrite and nitrosylated hemes," Journal of Molecular and Cellular Cardiology, 46, 2009, pp. 1-3.
Soane et al., "Mechanisms of Impaired Mitochondrial Energy Metabolism in Acute and Chronic Neurodegenerative Disorders," J. Neurosci. Res., Nov. 15, 2007; 85(15): 3407-3415.
Somia et al., "Gene Therapy: Trials and Tribulations," Nature Reviews Genetics, Nov. 2000, 1(2):91-99.
Stoll et al., "Quantum Dots on Gold: Electrodes for Photoswitchable Cytochrome c Electrochemistry," Small Journal, 2006, 2(6):741-743.
Stopp et al., "A new concept for navigated laser surgery," Laser Med. Sci. (2008) 23:261-266.
Szundi et al., "Flash-Photolysis of Fully Reduced and Mixed-Valence CO-Bound Rhodobacter sphaeroides Cytochrome c Oxidase: Heme Spectral Shifts," Biochemistry, 2007, 46:12567-12578.
Tafur et al., "Low-Intensity Light Therapy: Exploring the Role of Redox Mechanisms," Photomedicine and Laser Surgery, Nov. 4, 2008, 26(4):321-326.
Tajima et al., "A light-emitting diode fabricated from horse-heart cytochrome c," Solid State Communications, 126 (2003) 579-581.
The Laser Exchange: Delivering the medicine of the future, "Is it different from Ultrasuound?" www.laserexchange.co.uk/laser-therapy/ultrasound.htm, 2 pages Retreived Jul. 11, 2005.
Thor Product List, LLLT, Low Level Laser Therapy, Laz., http://www.thorlaser.com/prodlist/index.html, Oct. 6, 1999, pp. 1-4.
Trimmer et al., "Reduced axonal transport in Parkinson's disease cybrid neurites is restored by light therapy," Molecular Neurodegeneration, Jun. 17, 2009, 4(26):1-11.
Troy et al., "Optical properties of human skin in the near infrared wavelength range of 1000 to 2200 nm." Journal of biomedical optics. Apr. 2001;6(2):167-77.
Tuchin, "Tissue Optics: Light Scattering Methods and Instruments for Medical Diagnosis," SPIE Press, Tutorial Texts in Optical Engineering, vol. TT38, 2000, pp. 3-11.
Vakoc et al., "Real-time microscopic visualization of tissue response to laser thermal therapy," Journal of Biomedical Optics, Mar./Apr. 2007, vol. 12(2):1-3.
Van Breugel et al., "Power density and exposure time of He—Ne laser irradiation are more important than total energy dose in photo-biomodulation of human fibroblasts in vitro." Lasers in surgery and medicine. 1992;12(5):528-37.
Verkruysse et al., "Infrared Measurement of Human Skin Temperature to Predict the Individual Maximum Safe Radiant Exposure (IMSRE)," Lasers in Surgery and Medicine, 39:757-766, 2007.
Villringer et al., "Non-invasive optical spectroscopy and imaging of human brain function," TINS, 20(10):435-442, 1997.
Wang et al., "The Role of Abnormal Mitochondrial Dynamics in the Pathogenesis of Alzheimer's Disease," J Neurochem, May 2009, 109(Suppl 1):153-159.
Wells et al., "Biophysical Mechanisms of Transient Optical Stimulation of Peripheral Nerve," Biophysical Journal, Oct. 2007, 93:2567-2580.
Willis, "Intraocular microinjections repair experimental Parkinsons' disease," Brain Research, Jun. 2008, 1217:119-131.
Wilson, "Gene Therapy for Cystic Fibrosis: Challenges and Future Directions," J. Clin. Invest, Dec. 1, 1995, 96(6):2547-2554.
Wong-Riley, et al.: "Photobionnodulation Directly Benefits Primary Neurons Functionally Inactivated by Toxins", The Journal of Biological Chemistry, 2005; 280(6):4761-4771.
Yi et al., "Control of mitochondrial motility and distribution by the calcium: a homeostatic circuit," The Journal of Cell Biology, Nov. 22, 2004, 167:661-672.
Yujung et al., "Development of the fully automated program system; Can calculate transporting light intensity to the specific position in the brain tissue," http://pbil.kaist.ac.kr/lectures/bis500/report/proposal/team3proposalfinal.doc, accessed Apr. 30, 2007.
Zhang et al., "Near infrared light protects cardiomyocytes from hypoxia and reoxygenation injury by a nitric oxide dependent mechanism," Journal of Molecular and Cellular Cardiology, 46 (2009) pp. 4-14.
Zhu et al., "Cellular Model Studies of Brain-Mediated Monochromatic Phototherapy on Alzheimer's Disease," Seventh International Conference on Photonics and Imaging in Biology and Medicine, Mar. 6, 2009, (vol. 7280, p. 72801E). International Society for Optics and Photonics.
U.S. Appl. No. 10/723,171, filed Nov. 26, 2003, Streeter.
"Association of outcome with early stroke treatment: pooled analysis of ATLANTIS, ECASS, and NINOS rt-PA stroke trials," The Lancet, vol. 363, Mar. 6, 2004, pp. 768-774.
"Welcome to Lasers and Physical Therapy Care," http://copland.udel.edu/-17179/indexl .htm, Accessed Jan. 24, 2000 (p. 7 and 8 missing).
Acceliys, "Optical Absorption Spectra of Melanins—a Comparison of Theoretical and Experimental Results," Chemicals Case Study, Accelyrys, Oct. 5, 2005, http://accelrys.com/references/casestudies/archive/studies/melan ins-oartII.pdf.
Ad, N. et al, "Impact of low level laser irradiation on infaret size in the rat following myocardial infarction," International Journal of Cardiology, 80 (2001 ), pp. 109-116.
Agov, B. S., et al., "On the mechanism of therapeutic action of helium-neon laser in ischemic heart disease," KUN MED (Mose), pp. 102-105, 1985 (Abstract only).
Akai, Masami et al., "Laser's Effect on Bone and Cartilage Change Induced by Joint Immobilization: An Experiment With Animal Model," Lasers in Surgery and Medicine, 21 :480-484 (1997).
Albrecht-Buehler, Guenter. "Reversible, excitation light-induced enhancement of fluorescence of live mammalian mitochondria," The FASEB Journal, vol. 14, Oct. 2000, pp. 1864-1866.
Alexopoulous, George S. et al., "Clinically Defined Vascular Depression," American Journal of Psychiatry, 154:4, Apr. 1997, pp. 562-565.
Altshuler et al. "Extended Theory of Selective Photothermolysis," Lasers in Surgery and Medicine, 29:416-432 (2001).
Al-Watban, Farouk A.H. et al., "The Comparison of Effects between Pulsed and CW Lasers on Wound Healing," Journal of Clinical Laser Medicine & Surgery, vol. 22, No. 1, 2004, pp. 15-18.
Anders et al., Low power laser irradiation alters the rate of regeneration of the rat facial nerve, Laser Surg. Med., 13:72-82 (1993).
Anders, JJ, et al.: "Phototherapy Promotes Regeneration and Functional Recovery of Injured Peripheral Nerve", Neurological Research, 2004; 26: 233-239.
Anonymous, "Engineer, heal thyself," News Brief, Optoelectronics Report 3, www.optoelectronicsworld. com, Nov. 1, 1999.
Anonymous, "Practice Guideline for the Treatment of Patients With Major Depressive Disorder (Revision)," Am. J. Psychiatry, 257: 4, Apr. 2000, pp. 1-43.
Antunes, Fernando et al., "On the mechanism of biology of cytochrome oxidase inhibition by nitric acid," PNAS, vol. 101, No. 48, Nov. 30, 2004, pp. 16774-16779.
Arvidsson, Andreas, et al., Neuronal replacement from endogenous precursors in the adult rat brain after stroke, Nature Medicine, vol. 8, No. 9, Sep. 2002, pp. 963-970.
Asahi, Minoru, et al., Expression of Interleukin B Converting Enzyme Gene Family and bcI-2 Gene Family in the Rat Brain Following Permanent Occlusion of the Middle Cerebral Artery, Journal of Cerebral Blood Flow & Metabolism, vol. 17, No. 1, Jan. 1997, 12 pages.
Ashendorf, Douglas, "The Ability of Low Level Laser Therapy (LLL T) to Mitigate Fibromyalgic Pain," The CFIDS Chronicle Physicians' Forum Fall 1993.
Assia et al., "Temporal Parameters of Low Energy Laser Irradiation for Optimal Delay of Post-Traumatic Degeneration of Rat Optic Nerve", Brain Research, vol. 476, 1989, pp. 205-212.
Ataullakhanov et al. "What Determines the Intracellular ATP Concentration," Bioscience Reports, vol. 22, No. 5 and 6, Oct. and Dec. 2002.

(56) References Cited

OTHER PUBLICATIONS

Barnett, Alex H. et al., "Robust inference of baseline optical properties of the human head with three-dimensional segmentation from magnetic resonance imaging," Applied Optics, vol. 42, No. 16, Jun. 1, 2004, pp. 3095-3108.
Basford, Jeffrey R., "A Randomized Controlled Evaluation of Low-Intensity Laser Therapy. Plantar Fasciitis," Arch Phys Med Rahabil, vol. 79, Mar. 1998, pp. 249-254.
Basford, Jeffrey R., "Laser Therapy: A Randomized, Controlled Trial of the Effects of Low-Intensity ND:YAG Laser Irradiation on Musculoskeletal Back Pain," Arch Phys Med Rhabil, vol. 80, Jun. 1999, pp. 647-652.
Basford, Jeffrey R., M.D., PhD., "Lasers in Orthopedic Surgery—Laser Therapy: Scientific Basis and Clinical Role," May 1993, vol. 16, No. 5,pp. 541-547.
Beal, M. Flint, "Mitochondrial Dysfunction and Oxidative Damage in Alzheimer's and Parkinson's Diseases and Coenzyme 010 as a Potential Treatment," Journal of Bioenergetics and Biomembranes, vol. 26, No. 4, Aug. 2004, pp. 381-386.
Beauvoit, B. et al. "Contribution of the Mitochondrial Compartment to the Optical Properties of the Rat Liver: A Theoretical and Practical Approach," Biophysical Journal, vol. 67, Dec. 1994, pp. 2501-2510.
Beckerman, Heleen et al., "The Efficacy of Laser Therapy for Musculoskeletal and Skin Disorders: A Criteria-Based Meta-analysis of Randomized Clinical Trials," Physical Therapy, vol. 72, No. 7, Jul. 1992, pp. 483-491.
Belevich et al. "Exploring the proton pump mechanism of cytochrome c oxidase in real time," Preceedings of the National Academy of Sciences of the United States of America, vol. 104, No. 8, 2685-2690, Feb. 20, 2007.
Belevich et al. "Proton-coupled electron transfer drives the proton pump of cytochrom c oxidase," Nature: vol. 440, Apr. 2006.
Belkin, M. et al., "A Critical Review of Low Energy Laser Bioeffects", Lasers and Light in Ophthalmology, vol. 2, No. 1, pp. 63-71, 1988.
Bevilacqua et al; "In Vivo Local Determination of Tissue Optical Properties: Applications to the Human Brain"; Applied Optics; vol. 38, No. 22; Aug. 1, 1999; pp. 4939-4950.
Bibikova, A. et al., "Enhancement of Angiogenesis in Regenerating Gastroenemius Muscle of the Toad (*Bufo viridis*) by Low-Energy Laser Irradiation", Anatomy and Embryology (1994), vol. 190, pp. 597-602.
Bibikova, A. et al., "Promotion of Muscle Regeneration in the Toad (*Bufo viridis*) Gastrocnemius Muscle by Low-Energy Laser Irradiation", The Anatomical Record, vol. 235, 1993, pp. 374-380.
Bjordal, Jan Magnus et al., "Low Level Laser Therapy for Tendinopathy. Evidence of a Dose-Response Pattern," Physical Therapy Review, 2001, 6: 91-99, pp. 91-99.
Boelens, R. et al., "EPR Studies of the Photodissociation Reactions of Cytochrome c Oxidase-Nitric Oxide Complexes," Biochimica et Biophysica Acta, 679 (1982) pp. 84-94.
Boelens, Rolf et al., "An EPR Study of the Photodissociation Reactions of Oxidised Cytochrome c Oxidase-Ntiric Oxide Complexes," Biochimica et Biophysica Acta, 924 (1983) pp. 176-183.
Bolton, Peter et al., "The Direct Effect of 860nm Light on Cell Proliferation and on Succinic Dehydrogenase Activity of Human Fibroblasts In Vitro," Laser Therapy, 1995; 7: 055-060.
Borutaite, Vilmante et al., "Reversal of nitric oxide-, peroxynitrite- and S-nitrosothiol-induced inhibition of mitochondrial repiration or complex I activity by light and thiols," Biochimica et Biophysica Acta, 1459, (2000) Po. 405-412.
Brain Injury Source, vol. 3, Issue 4 (1999).
Brazzle, John, et al., Active Microneedles with Integrated Functionality, Technical Digest of the 2000 Solid-State Sensor and Actuator Workshop, Department of Bioengineering, University of Utah, Salt Lake City, Utah 84112 (five pages).

Brill, G.E., et al., Modifj;ing influence of low level laser irradiation on the relationships in endothelial cell-blood platelet system, 10th Congress of the European Society for Photobiology, Vienna, Austria (one page).
Bruch, Reinhard "Low Level Laser Therapy (LLL T)," Nevada Health Forum, Dec. 4, 2003.
Bullock, M. Ross et al., "Outcome measures for clinical trials in neurotrauma," Neurosurg. Focus 13 (1):Jul. 2002, pp. 1-11.
Burton et al. "Relation Between Blood Pressure and Flow in the Human Forearm," Journal of Applied Physiology, vol. 4, No. 5, pp. 329-339, Nov. 1951.
Byrnes, K.R., et al., Light Therapy Promotes Axonal Regeneration After Acute Spinal Cord Injury in Adult Rats, Program No. 275.2, Societv for Neuroscience, 2003, Abstract.
Calatrava, I. Ruiz et al., "Histological and Clinical Responses of Articular Cartilage to Low-level Laser Therapy: Experimental Study," Lasers in Medical Science, 1997, 12:117-121.
Campos et al. "Ruby Laser Hair Removal: Evaluation of Long-Term Efficacy and Side Effects," Lasers in Surgery and Medicine, 26: 177-185 (2000).
Cantanzaro et al. "Managing Tissue Heating in Laser Therapy to Enable Double-Blind Clinical Study," Proc. SPIE, vol. -6140, 614000 (2006).
Carati, Colin J. et al., "Treatment of postmastectomy lymphedema with low-level laser therapy. A double blind, placebo-controlled trial," Abstract accessed Sep. 29, 2003 from Cancer, vol. 98, Issue 6, Aug. 1, 2003, pp. 1114-1122.
Chance et al.: "Comparison of Time-Resolved and -Unresolved Measurements of Deoxyhemoglobin in Brain"; Proc. Natl Acad. Sc.i USA; vol. 85; ul. 1988; pp. 4971-4975.
Chance, et al., "Comparison of Time-Resolved and -Unresolved Measurements of Deoxyhemoglobin in Brain," Proc. Natl. Acad. Sci. USA, Jul. 1988, pp. 4971-4975.
Chen, James et al., "New Technology for Deep Light Distribution in Tissue for Phototherapy," The Cancer Journal, vol. 8, No. 2, Mar./Apr. 2002, pp. 154-163.
Chims Equipment Supplies, "Erchonia the healing light," http://www.chiros.com/au.erchonia.php, Accessed Feb. 7, 2002.
Choi, JeeHyun et al, "Noninvasive determination of the optical properties of adult brain: near-infrared spectroscopy approach," Journal of Biomedical Optics 9(1), pp. 221-229 (Jan./Feb. 2004).
Cohen, Michael A., Method of Forming Microneedles and other Micron-Scale Transdermal Probes, Office of Technology Licensing, University of California, Berkeley, http://otl.berkeley.edu/technology/inventiondetail. DhD/1000335, Abstract (two pages).
Conlan, M.J. et al., Biostimulation of Wound Healing by Low-Energy Laser Irradiation:, Journal of Clin. Periodontology, vol. 23, 1996, pp. 492-496.
De Scheerder, Ivan K. et al., "Intravascular Low-Power Laser Irradiation After Coronary Stenting: Long-Term Follow-Up," Lasers in Surgery and Medicine, 28:212-215, 2001.
De Scheerder, Ivan K. et al., "Optimal Dosing of Intravascular Low-Power Red Laser Light as an Adjunct to Coronary Stent Implantation: Insights from a Porcine Coronary Stent Model," Journal of Clinical Laser Medicine & Surgery, vol. 19, No. 5, 2001, pp. 261-265.
Diaz, Sergio H. et al., "Modeling the Thermal Response of Porcine Cartilage to Laser Irradiation," IEEE Journal on Selected Topics in Quantum Electronics, vol. 7, No. 6, Nov./Dec. 2001, pp. 944-951.
Dirnagl, Ulrich, et al., Pathobiology of ischaemic stroke: an integrated view, TINS, vol. 22, No. 9,1999, pp. 391-397.
Dobson, J., et al., Theory and Applications of a Magnetic Force Bioreactor, European Cells and Materials, vol. 4, Suppl. 2, 2002 (pp. 42-43).
Drugova, Olga et al., "Phototherapeutic effect of low-power red light on processes of lipid peroxidation in myocardium tissues of rats after ischemia," Proceedings of SPIE, vol. 4159 (2000), pp. 48-51.
Eells, J. T., et al.: "Mitochondrial signal transduction in accelerated wound and retinal healing by near-infrared light therapy" © 2004 Elsevier B.V. and Mitochondria Research Society, Mitochondrion 4 (2004) 559-567.

(56) References Cited

OTHER PUBLICATIONS

Eells, J.T., et al., Therapeutic photobiomodulation for methanol-induced retinal toxicity, Proceedings National Academv of Science(PNAS), vol. 100, No. 6, Mar. 18, 2003, DD. 3439-3444.
Elimadi, Aziz, et al., Trimetazidine Counteracts the Hepatic Injury Associated with Ischemia-Reperfusion by Preserving Michondrial Function, Journal of Pharmacology and Experimental TheraDeutics, vol. 286, No. 1, 1998, pp. 23-28.
Encyclopaedia Britanica Article—"Electromagnetic Field".
England, S. et al., "Low Power Laser Therapy of Shoulder Tendonitis," Scand J Rheumatology, 18:427-431, 1989.
EPO Extended Search Report re EP Application No. 09170679.6, dated Jan. 4, 2010. in 6 pages.
Examination Report for European Application No. 04 783 805.7 dated Mar. 25, 2009.
Finnie, J.W. et al., "Animal Models: Traumatic Brain Injury," Vet Pathol., 39:979-689 (2002).
Firbank et al; "A Theoretical Study of the Signal Contributions of Regions of the Adult Head to Near-Infrared Spectroscopy Studies of Visual Evoked Responses": Neuroimage; No. 8; 1998; pp. 69-7.
Fisher, M., "Characterizing the Target of Acute Stroke Therapy", Stroke, 1997, vol. 28, pp. 866-872.
Frank, Andrzej et al., "Does low output laser stimulation enhance the healing of crural ulceration? Some critical remarks," Medical Engineering & Physics 24 (2002) pp. 607-615.
Frank, Sandra et al., "Infrared Radiation Affects the Mitochondrial Pathway of Apoptosis in Human Fibroblasts," The Journal of Investigative Dermatology, 123:824-831, 2004.
Gage, Fred H., Brain, Repair Yourself, Scientific American, Sep. 2003, pp. 47-53.
Garn, Arne Nyholm et al., "The effect of low-level laser therapy on musculoskeletal pain: a metaanalysis," Pain, 52 (1993) pp. 63-66.
Gasparyan, L.V., et al., The influence of LED irradiation at different wavelengths on functional activity of blood platelets, 10th Congress of the European Society for Photobiology, Vienna, Austria, 2003 (one page).
Gasparyan, L.V., et al., The influence of LED irradiation at different wavelengths with antioxidants onfunctional activity of blood platelets, Laser, Florence, 2003 (one page).
Gasparyan, Levon et al., "Activation of Angiogenesis Under Influence of Red Low Level Laser Radiation," Laser Florence, 2004, pp. 1-8.
Gasparyan, Levon V., Biochemical and Biophysical Effects of Low Level Laser Irradiation, MAL 2000, Helsinki, Finland (three pages).
Gasparyan, Levon V., et al., Low Level Laser Therapy of Male Genital Tract Chronic Inflammations, WALT 2-nd Congress (Kansas City, USA), 1998 (two pages).
Gasparyan, Levon V., Experience of Russian (former USSR) Scientists in LLLT and UV Blood Irradiation, MAL 2000, Helsinki, Finland (four pages).
Gasparyan, Levon V., Investigation of Sensations, Associated with Laser Blood Irradiation, WALT 2-nd Congress (Kansas City, USA), 1998 (two pages).
Gasparyan, Levon V., Millimeter Wave Therapy, MAL 2000, Helsinki, Finland (three pages).
Genina et al., "Visualisation of the distributions of melanin and indocyanine green in biological tissues," Quantum Electronics, 38(3), pp. 263-268 (2008).
Gigo-Benato, D. et al., "Low-power laser biostimulation enhances nerve repair after end-to-side neurorrhaphy: a double-blind randomized study in the rat median nerve model," Lasers in Medical Science (2004), 19: pp. 57-65.
Go-Jo, Inc., (2002). "Watch for 'Subtle Energies' Featuring Dr. Larry Lytle," Flyer, South Dakota.
Gordon, G. A., "The Use of low power lasers in sports medicine", Clinical Sports Medicine 2, 53-61 (1990).
Gross, Garrett J., et al., Mechanisms of Postischemic Contractile Dysfunction, Myocardial Protection From Surgical Ischemic-Reperfusion Injury, An International Symposium, Asheville, North Carolina, Sep. 21-24, 1997, pp. 1897-1904.

Hamblin et al. "Mechanisms of Low Level Light Therapy," Proc. of SPIE, vol. 6140 614001-1 (2006).
Hammon, John W. Jr, MD, et al., Myocardial Protection Form Surgical Ischemic-Reperfusion Injury, Ann. Thorac. Surg., 1999:68:1897.
Harris, David Met al., "Laser Biostimulation. Review and Hypothesis," Laser Topics, 1988, pp. 9-14.
Harris, L.K. et al., "Traumatic Brain Injury-Induced Changes in Gene Expression and Functional Activity of Mitochondrial Cytochrome C Oxidase," Journal of Neurotrauma, vol. 18, No. 10, 2001, pp. 993-1009.
Hopkins, J Ty et al., "Low-Level Laser Therapy Facilitates Superficial Wound Healing in Humans: A Triple-Blind, Sham-Controlled Study," Journal of Athletic Training, 2004; 39(3):pp. 223-229.
Iadecola, Costantino, et al., Inhibition of inducible nitric oxide synthase ameliorates ischemic damaGe, Am. J. Phvsiol., vol. 268, 1995, pp. R286-R292.
Ilev, i., et al., "Smart optical fiber probes for precise tissue treatment," Proc. SPIE, 4616:220-228 (2002).
International Examination Report for EP 04 783 805, dated Jan. 19, 2010.
International Preliminary Report of Patentability for PCT/US2007/002474 dated Apr. 16, 2008.
International Preliminary Report on Patentability for PCT/US2007/00219 dated May 2, 2008.
International Search Report and Written Opinion dated Oct. 28, 2009 for PCT/US2009/037121 in 17 pages.
International Search Report and Written Opinion for PCT/US2005/004873 dated Sep. 5, 2005.
International Search Report and Written Opinion for PCT/US2007/002219 dated Jul. 5, 2007.
International Search Report and Written Opinion for PCT/US2007/002474 dated Sep. 28, 2007.
INVOS® Cerebral Oximeters, 2000 Mallinckrodt.
Ionto Corned® Product Brochure, date unknown, (In Greek).
Iverson, Grant L. et al., "Immediate Post-Concussion Assessment and Cognitive Testing," Normative Data for lmPACT Version 2.0; 28 pages, 2003.
Iverson, Grant L. et al., "Interpreting Change on lmPACT Following Sport Concussion," The Clinical Neuropsychologist, 2003, vol. 17, No. 4, pp. 460-467.
Jacques, Steven L. "Skin Optics," Oregon Medical Laser Center News, Jan. 1998, http://omlc.ogi/edu/news/jan98/skinoptics.html.
Janssen et al. "Modelling of temperature and perfusion during scalp cooling," Physics in Medicine and Biology, vol. 50, pp. 4065-4073 (2005).
Kaplan, Justin et al., "Mechanisms of lschemic Cerebral Injury," Resuscitation, 15 (1987) pp. 149-169.
Kaplan, Michael, "The Theralaser," date unknown.
Karrer et al., Long Pulsed Dye Laser for Photodynamic Therapy: Investigations In Vitro and In Vitro; Lasers in srug & Med.: vol. 25; 1999; pp. 51-59.
Karu et al. "Cell Attachment to Extracellular Matrices is Modulated by Pulsed Radiation at 820 nm and Chemicals that Modify the Activity of Enzymes in the Plasma Membrane," Lasers in Surgery and Medicine, 29: 274-281 (2001).
Karu, et al., Biostimulation of HeLa Cells by Low-Intensity Visible Light. II. Stimulation of DNA and RNA Synthesis in a Wide Spectral Range. Il Nuovo Cimento. (1984) p. 309-318.
Karu, llNA, Mechanisms of Low-Power Laser Light Action on Cellular Level, Effects of Low-Power Light on Biological Systems V, Proceedings of SPIE vol. 4159 (2000), pp. 1-17.
Karu, T.I., "Cellular mechanisms of low-power laser therapy," Proc. of SPIE, vol. 5149, 2003, pp. 60-66.
Karu, T.I., Low power laser therapy, in Biomedical Photonics Handbook, Ch. 48, Editor-in-Chief Tuan Vo-Dinh, Boca Raton, CRC Press, 2003.
Karu, Tiina I. et al., "A Novel Mitochondrial Signaling Pathway Activated by Visible-to-near Infrared Radiation," Photochemistry and Photobiology, 2004, 80: 366-372.
Karu, Tiina I. et al., "Changes in absorbance of monolayer of living cells induced by laser irradiation at 633, 670, and 820 nm," Proc. of SPIE, vol. 4431, 2002, pp. 306-312.

(56) References Cited

OTHER PUBLICATIONS

Karu, Tiina I. et al., "Irradiation with a diode at 820 nm induces changes in circular dichroism spectra (250-780 nm) ofliving cells," Proc. ofSPIE, vol. 4433, 2001, pp. 97-102.

Karu, Tiina, "Primary and secondary mechanisms of action of visible to near-IR radiation on cells," Journal of Photochemistry and Photobiology, 49 (1999) pp. 1-17.

Karu, Tiina, "Primary mechanisms of action of low-intensity laser light on cells," SPIE, vol. 3829, 1999, pp. 42-53.

Karu, Tiina, Mechanisms of interaction of monochromatic visible light with cells, Proc. SPIE, vol. 2630, pp. 2-9.

Karu, Tiina, Photobiological Fundamentals of Low Power Laser Therapy, IEEE Journal of Quantum Electronics, vol. QE-23, No. 10, Oct. 1987, pp. 1703-1717.

Karu, Tiina. "Can a mechanism based on changes in redox properties of cytochrome c oxidase be crucial in explaining of low-power laser effects?" SPIE, vol. 3732, 1999. pp. 202-213.

Katona, Eva et al., "Membrane Effects of Low Level Infrared Laser Irradiation, as seen in Metabolically Intact and Impaired Human Blood Cells," Romania J Biphys., vol. 14, Nos. 1-4, 2004, pp. 99-108.

Kemp, Graham J "Mitochondrial dysfunction in chronic ischemia and peripheral vascular disease," Department of Musculoskeletal Science, Royal Liverpool University Hospital, University of Liverpool, Jul. 12, 2004.

Khodjakov, Alexey et al., "Laser micro-irradiation of mitochondria: is there an amplified mitochondrial death signal in neural cells?" Mitochondrion 3 (2004) pp. 217-227.

Kipshidze, Nicholas et al., "Low-Power Helium: Neon Laser Irradiation Enhances Production of Vascular Endothelial Growth Factor and Promotes Growth of Endothelial Cells in Vitro," Lasers in Suroerv and Medicine, 28:355-364 (2001).

Klein, Robert G. et al., "Low-Energy Laser Treatment and Exercise for Chronic Low Back Pain: Double-Blind Controlled Trial," Arch Phys Med Rehabil, vol. 71, Jan. 1990, pp. 34-37.

Kolpakova et al., "Effect of the He—Ne laser irradiation on resistance of the isolated heart to the ischemic and reperfusion injury," Ross Fiziol Zh Im I M Sechenova, English Abstract accessed on Nov. 9, 2004 from Medscaoe WebMD, Dec. 2003; 89(12):1496-1502.

Kosiak, Michael M.D.,: "Etiology and Pathology of Ischemic Ulcers", Archives of Physical Medicine and Rehabilitation, vol. 40, No. 1, 37th Annual Session, Minneapolis, Aug. 30-Sep. 4, 1959, pp. 62-69.

Kriesler et al.: "Effect of low-level GaAIAs laser irradiation on the proliferation rate of human periodontal ligament fibroblasts: an in vitro study," Journal of Clinical Periodontology, (2003), 30: 353-358.

Lagan, Katie M., "Low-Intensity Laser Therapy/Combined Phototherapy in the Management of Chronic Venous Ulceration: A Placebo-Controlled Study," Journal of Clinical Laser Medicine & Surgery, vol. 20, No. 3, 2002, pp. 109-116.

Lam, T.S., et al., "Laser stimulation of collagen synthesis in human skin fibroblast cultures," Lasers Life Sci., 1:61-77 (1986).

Lapchak, P.A., et al.: "Transcranial Infrared Laser Therapy Improves Clinical Rating Scores After Embolic Strokes in Rabbits", Stroke 2004; 35: 1985-1988.

Laser Exchange: The Laser Exchange: Delivering the medicine of the future, http://www.laserexchan!!e.co.uk/laser-theraov/ultrasound.h!m; 2 pages.

Lasermedics, Inc., "The Effects of the Microlight 830 on Repetitive Stress Injuries," Aug. 4, 1993.

Lee, Garret et al., "New concepts in pain management and in the application of low-power laser for relief of cervicothoracic pain syndromes," American Hearth Journal, vol. 132, No. 6, Dec. 1996, pp. 1329-1334.

Leker, R. R., et al.: "Cerebral ischemia and trauma—different etiologies yet similar mechanisms: neuroprotective opportunities", Brain Research Reviews 39 (2002) pp. 55-73.

Lepselter et al. "Biological and clinical aspects in laser hair removal," Journal of Dermatological Treatment, 15, 72-83 (2004).

Leung, Mason C.P., et al., Treatment of Experimentally Induced Transient Cerebral Ischemia with Low Energy Laser Inhibits Nitric Oxide Synthase Activity and Up-Regulates the Expression of TransforminR Growth Factor-Beta I, Lasers in Surnerv and Medicine~vol. 31, 2002, pp. 283-288.

Lievens, P.O, "The Effect of 1.R. Laser Irradiation on the Vasomotricity of the Lymphatic System," Lasers in Medical Science, vol. 5: 189, 1991.

Lisman et al. "Two Light-Induced Processes in the Photoreceptor Cells of Limulus Ventral Eyes," The Journal of General Physiology, vol. 58, pp. 544-561, 1971.

Liu, Dong et al., "Activation of Mitochondrial ATP-Dependent Potassium Channels Protects Neurons Against Ischemia-Induced Death by a Mechanism Involving Suppression of Bax Translocation and Cytochrome c Release," Journal of Cerebral Blood Flow & Metabolism, 22:431-443, 2002.

Liu, Timon Cheng-Yi et al., "Membrane mechanism of low intensity laser Biostimulation on a cell," Biomedical Photonics and Optoelectronic Imaging, Proceedings of SPIE, vol. 4224 (2000), pp. 186-192.

Lo, Eng H. et al., "Mechanisms, Challenges and Opportunities in Stroke," Nature Reviews: Neuroscience, vol. 4, May 2003, pp. 399-415.

Low-Level Laser Therapy: Compu-Lase, Spectra-Medics Pty Ltd—Low-Level Laser Therapy Specialists, http://www.spectra-medics.com/compulase.html, 1998.

Lychagov, V. V., et al.: "Experimental study of cadavers head transmittance", Saratov Fall Meeting 2004: Optical Technologies in Biophysics and Medicine VI, Proc. of SPIE vol. 5771, pp. 328-331.

Lychagov, Vladislav V., et al. Experimental study of NIRtransmittance of the human skull, Proc. of SPIE, vol. 6085, 2006 (five pages).

MacDonald, Loch R. et al., "Pathophysiology of Cerebral Ischemia," Neural Med Chir (Tokyo) 38, Jan. 1998, pp. 1-11.

Maegawa, Yasuyo et al., "Effects of Near-Infrared Low-Level Laser Irradiation on Microcirculation," Lasers in Surgery and Medicine, 27:427-437 (2000).

Manstein, D. et al., "Effects of Diode Laser Versus Flashlamp Exposure on Hair Follicles," American Society for Laser Medicine and Surgery Abstracts, 2004.

Manstein, D. et al., "Effects of Fluence and Pulsed Duration for Flashlamp Exposure on Hair Follicles," Presented at the 21st Annual Meeting of the American Society for Laser Medicine & Surgery, Apr. 2001.

Matas et al."Eliminating the Issue of Skin Color in Assessment of the Blanch Response," Advances in Skin & Wound Care, vol. 14 (4, Part 1 of 2), pp. 180-188, Jul./Aug. 2001.

Mautes, Angelika E.M. et al., "Changes in Regional Energy Metabolism After Closed Head Injury in the Rat," Journal of Molecular Neuroscience, vol. 16, 2001, pp. 33-39.

Mayorga, Maria A., "The pathology of primary blast overpressure injury," Toxicology 121 (1997) pp. 1-28.

Mester, E., et al., Effect of Laser Rays on Wound Healing, The American Journal of Surgery, vol. 122, Oct. 1971, pp. 532-535.

Mester, Endre et al., The Biomedical Effects of Laser Application, Lasers in Surgery and Medicine, 5:31-39 (1985).

Minoru, Asahi, et al, Expression of lnterleukin-1 [beta] Converting Enzyme Gene Family and bcl-2 Gene Family in the Rat Brain Following Permanent Occlusion of the Middle Cerebral Artery, Journal of Cerebral Blood Flow & Metabolism, vol. 17(1), Jan. 1997, pp. 11-18.

Mirsky, N. et al., "Promotion of Angiogenesis by Low Energy Laser Irradiation," Antioxidants & Redox Signaling, vol. 4, No. 5, 2002, pp. 785-791.

Mochizuki-Oda, Noriko et al., "Effects of Near-Infrared Laser on Neural Cell Activity," American Institute of Physics, 2004, pp. 192-195.

Mochizuki-Oda, Noriko et al., Effects of Near-Infra-Red Laser Radiation on Adenosine Triphosphate and Adenosine Diphosphate Contents of Rat Brain Tissue, Neuroscience Letters, vol. 323, 2002, pp. 207-210.

Moore, K.C., "The Use of Low Level Laser Biostimulation for the Treatment of Chronic Pain Syndromes," Laser Systems for Photobiology and Photomedicine, 1991, pp. 129-135.

(56) References Cited

OTHER PUBLICATIONS

Morita, Hideki et al., "Clinical Application of Low Reactive Level Laser Therapy (LLL T) for Atopic Dermatitis," Keio J Med, 42 (4): 174-176, 1993.
Morrone, G. et al., "Muscular Trauma Treated with a Ga—Ai—As Diode Laser: In Vivo Experimental Study," Lasers Med Sci, 1998, 13:293-298.
Nadareishvili, Zurab et al., "Neural Regeneration after Stroke," The New England Journal of Medicine, 348; 23, Jun. 5, 2003, pp. 2355-2356.
Naeser, Margaret A. et al., "Carpal Tunnel Syndrome Pain Treated With Low-Level Laser and Microamperes Transcutaneous Electric Nerve Stimulation: A Controlled Study," Arch Phys Med Rahbil, vol. 83, Jul. 2002, pp. 978-988.
Narayan, Raj K. et al., "Clinical Trials in Head Injury," Journal of Neurotrauma, vol. 19, No. 5, 2002, pp. 503-557.
Neumar, Robert W., "Molecular Mechanisms of Ischemic Neuronal Injury," Annals of Emergency Medicine, 35:5, Nov. 2000, pp. 483-506.
Niitsuma et al. "Experimental study of decubitus ulcer formation in the rabbit ear lobe," Journal of Rehabilitation Research and Development, vol. 40, No. 1, pp. 67-72, Jan./Feb. 2003.
Nilsson, Thomas, "Photoinduced electron transfer from tris(2,2'-bipyridyl)ruthenium to cytochrome c oxidase," Proc. Natl. Acad. Sci. USA 89 (1992) pp. 6497-6501.
Nishioka, Norman S., et al., Reflection and Transmission of Laser Light From the Esophagus: The Influence of Incident Angle, Gastroenterology, vol. 94, 1988, pp. 1180-1185.
Nissan, M. et al., "HeNe Laser Irradiation Delivered Transcutaneously: Its Effect on the Sciatic Nerve of Rats", Lasers in Surgery and Medicine, vol. 6, pp. 435-438, 1986.
Noble, Peter B. et al., "Locomotory Characteristics of Fibroblasts Within a Three-Dimensional Collagen Lattice: Modulation by a Helium/Neon Soft Laser," Lasers in Surgery and Medicine, 12:669-674 (1992).
Notes by Joan B. Martin MD from presentations on Light Activated Tissue Regeneration and Therapy given Aug. 22-27, 2004.
Nussbaum, E. et al., "Comparison of Ultrasound/Ultraviolet-C and Laser for Treatment of Pressure Ulcers in Patients With Spinal Cord Injury," Physical Therapy, vol. 74, No. 9, Sep. 1994, pp. 812-823.
Okada, Eiji et al, "Near-infrared light propagation in an adult head model. II. Effect of superficial tissue thickness on the sensitivity of the near-infrared spectroscopy signal," Applied Optics, Jun. 1, 2003, vol. 42, No. 16, Po. 2915-2922.
Olesin, Al, et al., Laser irradiation of venous blood for production of reperfusion syndrome in myocardial infarction, Patologisheskaia fiziologiia, 1992 (Abstract only).
Optical Properties of Tissues with Strong (Multiple) Scattering, source unknown.
Oron, Uri, et al., Attenuation of Infarct Size in Rats and Dogs after Myocardial Infarction by Low-Ener'ZV Laser Irradiation, Lasers in Survery and Medicine vol. 28, 2001, on. 204-211.
Oron, Uri, et al., Low-Energy Laser Irradiation Reduces Formation of Scar Tissue After Myocardial Infarction in Rats and Dogs, Circulation, vol. 103, Jan. 16, 2001, pp. 296-301.
Palmgren, Nina et al., "Low-Power Laser Therapy in Rheumatoid Arthritis," Lasers in Medical Science, vol. 4:193, 1989.
Park, James L., Ph.D., et al., Mechanisms of Myocardial Reperfusion Injury, The Annals of Thoracic Surgery, Official Journal of the Society of Thoracic Surgeons and the Southern Thoracic Surgical Association, vol. 68, No. 5, Nov. 1999, DD. 1905-1912.
Passarella, S., et al.: "Increase in the ADP/ATP Exchange in Rat Liver Mitochondria Irradiated In Vitro by Helium-Neon Laser", Biochemical and BioPhysical Research Communications, vol. 156, No. 2, Oct. 31, 1988, pp. 978-986.
Peszynski-Drews, Cezary et al., "Laser biostimulation of the patients suffering from multiple sclerosis in respect of biological influence of laser light," Proceedings of SPIE, vol. 5229 (2004), pp. 97-103.

Peterson, Jill et al., "Material Properties of the Human Cranial Vault and Zygoma," The Anatomical Record Part A, 274A:785-797 (2003).
Physical Therapy, The Efficacy of Laser Therapy for Musculoskeletal and Skin Disorders: A Criteria-Based Metanalysis of Randomized Clinical Trials, vol. 72, No. 7, Jul. 1992, pp. 483/12-491/21.
Pogue et al; "Comparison of Image Geometries for Diffuse Optical Tomography of Tissue": Optics Express; vol. 4, No. 8; Apr. 12, 1999; pp. 270-286.
Puett, David W. et al., "Published Trials of Nonmedicinal and Noninvasive Therapies for Hip and Knee Osteoarthritis," American College of Physicians, vol. 121, No. 2, Jul. 15, 1994, pp. 133-140.
Reddy, G. Kesava et al., "Laser Photostimulation of Collagen Production in Healing Rabbit Achilles Tendons," Lasers in Surgery and Medicine, 22:281-287 (1998).
Regulatory Insight Inc., "Tuco Erchonia PL2000," Premarket Notification, 2001.
Respond 2400 Laser Therapy System, http://www.nmia.com/-pegasus/las2400.html, Accessed Nov. 3, 1998.
Respond Systems, Inc., "Understanding Low Level Laser Therapy," 1991.
Respond Systems, Inc., "Understanding Pulse Magnetic Field Therapy," 1991.
Reznikov, LL. et al., "The Biomechanism of Low-Energy Laser Irradiation is Similar to General Adaptive Reaction," Proc. SPIE, vol. 2086, 380 (1994).
Rochkind, S. et al., "New trend in neuroscience: Low-power laser effect on peripheral and central nervous system (basic science, preclinical and clinical studies)," Neurological Research, vol. 14, Mar. 1992, pp. 2-11.
Rochkind, S. et al., "Spinal Cord Response to Laser Treatment of Injured Peripheral Nerve," Spine, vol. 15, No. 1, 1990, pp. 6-10.
Rochkind, S. et al., "Stimulatory Effect of He—Ne Low Dose Laser on Injured Sciatic Nerves of Rats," Neurosurgery, vol. 20, No. 6, 1987, pp. 843-847.
Rochkind, S.: Central Nervous System Transplantation Benefitted by Low-power Laser Irradiation, 1992, Lasers in Medical Science, 7: 143-151.
Roynesdal, A.K. et al., "The effect of soft-laser application on postoperative pain and swelling, A double-blind, crossover study," International Journal of Oral Maxillofacial Surgery, 1993: 22: 242-245.
Rumpf, Christian, "New minimally-invasive laser treatment in orthopaedics on spinal deformations and bone tumours," Dissertation, University of Heidelberg, 2001.
Samosiuk et al., "Magnetic and laser therapy of acute ischemic stroke," Vopr Kurortol Fizioter Lech Fiz Kult, English Abstract accessed on Nov. 9, 2004 from Medscape from WebMD, Mar.-Apr. 2003;(2):19-20.
Sasaki, K. et al., "To Examine the Adverse Photothermal Effects of Extended Dosage Laser Therapy InVivo on the Skin and Subcutaneous Tissue in the Rat Model," Laser Therapy, vol. 4, No. 2, Apr.-Jun. 1992.
Savchenko, Eugeny P., et al.: "Monte-Carlo simulation of brain activity response for intense NIRradiation", Proc. of SPIE vol. 5696, Mar. 29, 2005, pp. 232-239.
Scheele, Jurgen S. et al., "Kinetics of NO Ligation with Nitric-oxide Synthase by Flash Photolysis and Stopped-flow Spectrophotometry," The Journal of Biological Chemistry, vol. 274, No. 19, May 1999, Po. 13105-13110.
Schultz, Robert J. et al., "Effects of Varying Intensities of Laser Energy on Articular Cartilage: A Preliminary Study," Lasers in Surgery and Medicine, 5:577-588 (1985).
Semenza, Gregg L., et al., Regulation of Mammalian 02 Homeostasis by Hypoxia-Inducible Factor 1, Ann. Rev. Cell Dev. Biol., vol. 15, 1999, pp. 551-578.
Shefer, Gabriella et al., "Low-energy laser irradiation promotes the survival and cell cycle entry of skeletal muscle satellite cells," Journal of Cell Science, 115, 1461-1469 (2002).
Sieren, A. et al., "Our Own Experience in Clinical Use of Low Power Laser Therapy," Przegl Lek, 1995; 52(1):13-5.
Sim-Med Ltd, Laser Therapy Manufacturers, www.therapylaser.com, date unknown.

(56) References Cited

OTHER PUBLICATIONS

Sims, Neil R., "Mitochondrial contributions to tissue damage in stroke," Neurochemistry International, 40 (2002), pp. 511-526.
Simunovic, Zlatko et al., "Treatment of Medial and Lateral Epicondylitis—Tennis and Golfer's Elbow-with Low Level Laser Therapy: A Multicenter Double Blind, Placebo-Controlled Clinical Study on Patients," Journal of Clinical Laser Medicine & Surgery, vol. 16, No. 3, 1998, pp. 145-151.
Siposan, Dan G. et al., "Effect of Low-Level Laser Radiation on Some Rheological Factors in Human Blood: An in Vitro Study," Journal of Clinical Laser Medicine & Surgery, vol. 18, No. 4, 2000, pp. 185-195.
Smith, Kendric C., "The Photobiological Basis of Low Level Laser Radiation Therapy," Photobiological Basis of LLL T, pp. 1-7.
Smith, Rich, "Seeing the Light: How light therapy is surprising skeptics and gaining converts," Physical Therapy Products, Apr./May 2004.
Snyder, S.K., et al., "Quantitation of calcitonin gene-related peptide mRNA and neuronal cell death infacial motor nuclei following axotomy and 633 nm low power laser treatment," Surg. Med., 31:216-222 (2002).
Snyder-Mackler, Lynn et al., "Effect of Helium-Neon Laser on Musculoskeletal Trigger Points," Physical Therapy, vol. 66, No. 7, Jul. 1986, pp. 1087-1090.
Sofiano Bros Ltd., Medical Laser, date unknown.
Sommer, A, et al., "Biostimulatory Windows in Low-Intensity Laser Activation: Lasers, Scanners, and NASA's Light-Emitting Diode Array System," Journal of Clinical Laser Medicine & Surgery, vol. 19, No. 1, 2001, pp. 29-33.
Spivak, Jeffrey M. et al., "The Effect of Low-Level ND:YAG Laser Energy on Adult Articular Cartilage InVitro," Arthroscopy: The Journal of Arthroscopic and Related Surgery, 8(1):36-43, 1992.
Stelian, Jean et al., "Improvement of Pain and Disability in Elderly Patients with Degenerative Osteoarthritis of the Knee Treated with Narrow-Band Light Therapy," The American Geriatrics Society, vol. 40, No. 1, Jan. 1992, pp. 31-34.
Streeter, J., et al., "Mechanisms of action of light therapy for stroke and acute myocardial infarction," Mitochondrion 4:569-576 (2004).
Stys, Peter K., Anoxis and Ischemic Injury of Myelinated Axons in CNS White Matter: From Mechanistic Concepts to Therapeutics, J. Cereb. Blood Flow Metab., vol. 18, No. 1, Jan. 1998, 42 pages.
Sukstanskii, A.L. et al., "An analytical model of temperature regulation in human head," Journal of Thermal Biology, 29 (2004), pp. 583-587.
Super Lizer™, Spot Type Polarized Light Therapy Equipment Model HA-550, Tokyo Iken Co., Ltd. (date unknown).
Tavalin, Steven J. et al., "Inhibition of the Electrogenic Na Pump Underlies Delayed Depolarization of Cortical Neurons After Mechanical Injury or Glutamate," The American Physiological Society, 1997, pp. 632-638.
The Laser Exchange, "LEDS," http://laser.uk.com/tech/index.html, Accessed Jan. 24, 2000 (p. 1 missing).
Theralase Inc., "Low Level Light Therapy (LLL T)," 1999.
Theralase Inc., "Therapeutic Lasers," date unknown.
Theralase Inc., "Therapeutic Medical Laser Summary," date unknown.
Therapeutic Laser Corporation, "Healing Light Healing the World," website unknown, Accessed Jul. 1, 1999.
Thor Laser, 200m W, Thor, lilt, LLL T, Low Level Laser Therapy, low level laser therapy, Lazer, Thorl, http://www.thorlaser.com/specs/200m W.html Oct. 6, 1999, p. I.
Thor Laser, 200mW, Thor, lilt, LLLT, Low Level Laser Therapy, low level laser therapy, Laser, Thor!., http://www.thorlaser.com/specs/200m W650nm.html Oct. 6, 1999, p. I.
Thor Laser, 500m W, Thor, lilt, LLLT, Low Level Laser Therapy, low level laser therapy, Lazer, Thor!., http://www.thorlaser.com/specs/500m W.htm! Oct. 6, 1999, p. I.
Thor Laser, 680nm Probe, Thor, lilt, LLL T, Low Level Laser Therapy, low-level laser therapy, Laser, http://www.thorlaser.com/specs/680.htm! Oct. 6, 1999, p. I.

Thor Laser, IOOmW, Thor, lilt, LLLT, Low Level Laser Therapy, low level laser therapy, Lazer, Thorl., http://www.thorlaser.com/specs/ IOOm W.html Oct. 6, 1999, p. I.
Thor Laser, Is LLLT Different from Ultrasound?, http://www.thorlaser.com/LLLT/is-LLLT-difffrom-ultrasound.htm, 2 pages.
Thor Laser, Product List, Thor, lilt, LLLT, Low Level Laser Therapy, Laz., http://www.thorlaser.com/orodlist/index.html Oct. 6, 1999, on. 1-4.
Thor Laser, Specifications, Thor, lilt, LLL T, Low Level Laser Therapy, low-level laser therapy, http://www.thorlaser.com/snec~ Oct. 6, 1999, pp. 1-2.
Thor Models LX, DOii & DD, Accessed Jul. 1, 1999.
Tio, Rene A. et al., "PET for Evaluation of Differential Myocardial Perfusion Dynamics After VEGF Gene Therapy and Laser Therapy in End-Stage Coronary Artery Disease," The Journal of Nuclear Medicine, vol. 45, No. 9, Sep. 2004, pp. 1437-1443.
Tolias, Christos M. et al., "Critical Appraisal of Neuroprotection Trials in Head Injury: What Have We Learned?" The Journal of the American Society for Experimental NeuroTherapeutics, vol. 1, pp. 71-79, Jan. 2004.
Toon, John, Taking the "Ouch" Out of Needles: Arrays of Micron-Scale "Microneedles" Offer New Technique for Drug Delivery, Georgia Tech Research News, Jun. 22, 1998 (three pages).
Toricelli, P., et al., Laser Biostimulation of cartilage: in vitro evaluation, Biomed Pharmacother 2001, vol. 55, pp. 117-120.
Trelles, M.A. et al., "Bone Fracture Consolidates Faster With Low-Power Laser," Lasers in Surgery and Medicine, 7:36-45 (1987).
Trimmer, Patricia A. et al., "Mitochondrial abnormalities in cybrid cell models of sporadic Alzheimer's disease worsen with passage in culture," Neurobiology of Disease, vol. 15, 2004, pp. 29-39.
Trimmer, Patricia A. et al., "Parkinson's disease transgenic mitochondrial cybrids generate Lewy inclusion. bodies," Journal of Neurochemistry, (2004) 88, pp. 800-812.
Trimmer, Patricia A., "Abnormal Mitochondrial Morphology in Sporadic Parkinson's and Alzheimer's Disease Cybrid Cell Lines," Experimental Neurology, 162, 37-50 (2000).
Tuchin, V., Optical Properties of Tissues With Strong (Multiple) Scattering, Tissue Optics. Light Scattering Methods and Instruments for Medical Diagnosis, SPIE Press, Bellingham, WA 20000 (2000), pp. 3-11.
Tuner, Jan et al., "It's All in the Parameters: A Critical Analysis of Some Well-Known Negative Studies on Low-Level Laser Therapy," Journal of Clinical Laser Medicine & Surgery, vol. 16, No. 5, 1998, pp. 245-248.
Tuner, Jan, et al., Low Level Laser Therapy, Clinical Practice and Scientific BackgrounQ, Prima Books in Sweden AB, 1999, pp. 1-9, 45-58, 59-109, 62-114; 113-116, 118, 132-134, 134-135; 149-151; 151-156; 185; 334-364.
U.S. Appl. No. 10/764,986, filed Jan. 26, 2004.
Udekwu, Pascal et al., "Glasgow Coma Scale Score, Mortality, and Functional Outcome in Head-Injured Patients," The Journal of Trauma, Injury, Infection, and Critical Care, 2004; 56:1084-1089.
Usuba, Mariko et al., "Effect of Low-Level Laser Therapy (LLL T) on Viscoelasticity of the Contracted Knee Joint: Comparison With Whirlpool Treatment Rats," Lasers in Surgery and Medicine, 22:81-85 (1998).
Van Brugel, H.H.F.1., Bar, P.R., "He—Ne Laser Irradiation Affects Profileration of Cultered Rat Schwann Cells in Dose-dependent Manner," 1993, Journal of Neurocytology, 22, 185-190.
Van Brugel, Hans H.F.I., et al., Power Density and Exposure Time of He—Ne Laster Irradiation are More Important Than Total Energy Dose in Photo-Biododucation of Human Fibroblasts in Vitro, 1992, Wilev-Liss, Inc., pp. 528-537.
Vangsness Jr., C. Thomas et al., "A Literature Review of Lasers and Articular Cartilage," Lasers in Orthopedic Surgery, May 1993, 16:5(593-598).
Vasseljen, Otto et al., "Low Level Laser Versus Placebo in the Treatment of Tennis Elbow," Scand J Rehab Med, 24:37-42, 1992.
Verma, et al., Gene Therapy—promises, problems, and prospects, Nature 389: 239-242, 1997.
Vladimirov, Yu. A. et al., "Molecular and Cellular Mechanisms Triggered by Low-level Laser Irradiation," Biophysics, vol. 49, No. 2, 2004, pp. 325-336.

(56) References Cited

OTHER PUBLICATIONS

Vladimirov, Yu. A. et al., "Photobiological Principles of Therapeutic Applications of Laser Radiation," Biochemistry (Moscow), vol. 69, No. 1, 2004, pp. 81-90.

Volotovskaia et al., "Antioxidant action and therapeutic efficacy of laser irradiation of blood in patients with ischemic heart disease," Vopr Kurortol Fizioter Lech Fiz Kult, English Abstract accessed Nov. 9, 2004 from Medscaoe from WebMD, Mav-Jun. 2003; (3):22-5.

Walker, J., "Relief from Chronic Pain by Low Power Laser Irradiation," Neuroscience Letters, 43(1983) 339-344.

Warburg, Otto, "The Chemical Constitution of Respiration Ferment," Science, vol. LXVIII, No. 1767, Nov. 9, 1928, pp. 437-443.

Warburg, Otto, "The oxygen-transferring ferment of respiration," Nobel Lecture, Dec. 10, 1931, pp. 254-268.

Waynant, R et al., "Review of Laser Therapy: Current Status and Consensus for Research Needed for Further Progress," NML T Conference 2003.

Weiss, N. et al., "Enhancement of Muscle Regeneration in the Rat Gastrocnemius Muscle by Low Energy Laser Irradiation", Anat. Embroyl. (1992), vol. 186, pp. 497-503.

Wever, R. et al., "The Photoreactivity of the Copper-NO Complexes in Cytochrome c Oxidase and in Other Copper-Containing Proteins," Laboratory of Biochemistry, Journal of Inorganic Biochemistry, 23, 227-232 (1985).

Whelan, H.T., et al., "Effect of NASA Light-Emitting Diode Irradiation on Wound Healing," J. Clinical Laser Med. & Surg., 19:305-314 (2001).

Whittaker, Peter et al., "Ventricular Remodeling After Acute Myocardial Infarction: Effect of Low-Intensity Laser Irradiation," Lasers in Surgery and Medicine, 27:29-38 (2000).

Wong-Riley, Margaret T.T., et al., Light-emitting diode treatment reverses the effect of TTX on cytochrome oxidase in neurons, NeuroReoort, vol. 12, No. 14, Oct. 8, 2001, pp. 3033-3037.

Yaakobi, Tali, et al., Long-term effect of low energy laser irradiation on infarction and reperfusion injury in the rat heart, J. Appl. Physiol., vol. 90, 2001, pp. 2411-2419.

Yahoo! News, "Light on Knees Affects Body's Clock," http://omlc.ogi.edu/news/feb98/pressrelease/knees_1.html, Accessed Apr. 6, 2007.

Yamamoto, Yahuhiro et al., "Effect of Low-Power Laser Irradiation on Procollagen Synthesis in Human Fibroblasts," Journal of Clinical Laser Medicine & Surgery, vol. 14, No. 3, 1996, pp. 129-132.

Yang, Fu-Shou, "Medical Applications of Low Power Lasers in China," Laser Systems for Photobiology and Photomedicine, 1991, pp. 115-127.

Yaroslaysky, A. N. et al., "Optical properties of selected native and coagulated human brain tissues in Vitro in the visible and near infrared spectral range," Physics in Medicine and Biology, 47 (2002), pp. 2059-2073.

Yin, Xiao-Ming et al., "Bid-mediated Mitochondrial Pathway is Critical to Ischemic Neuronal Apoptosis 303 and Focal Cerebral Ischemia," The Journal of Biological Chemistry, vol. 277, No. 44, Nov. 1, 2002, pp. 42074-42081.

Young, A.E.R. et al., "Behaviour of near-infrared light in the adult human head: implications for clinical near-infrared spectroscopy," British Journal of Anaesthesia, 84 (1): 38-42 (2000).

Yu, W. et al., "Photomodulation of Oxidative Metabolism and Electron Chain Enzymes in Rat Liver Mitochondria," Photochem and Photobio, 66:866-871 (1997).

Yu, Wei et al., "The Effect of Laser Irradiation on the Release of bFGF From 3T3 Fibroblasts," Photochemistry and Photobiology, vol. 59, No. 2, pp. 167-170, 1994.

Zeischegg, Peter M., "Low Level Laser Therapy (LLL T)," http://www.drz.org/laser.htm, Accessed Oct. 1, 1999.

Zenzie et al. "Evaluation of Cooling Methods for Laser Dermatology," Lasers in Surgery and Medicine, 26:130-144 (2000).

* cited by examiner

METHOD FOR PROVIDING PHOTOTHERAPY TO THE BRAIN

CLAIM OF PRIORITY

This application is a continuation of U.S. patent application Ser. No. 11/482,220, filed Jul. 7, 2006, which is a continuation of U.S. patent application Ser. No. 10/682,379, filed Oct. 9, 2003, and which claims benefit to U.S. Provisional Application No. 60/442,693, filed Jan. 24, 2003, U.S. Provisional Application No. 60/487,979, filed Jul. 17, 2003, and U.S. Provisional Application No. 60/502,147, filed Sep. 11, 2003, and which is a continuation-in-part of U.S. patent application Ser. No. 10/287,432, filed Nov. 1, 2002, which claims benefit to U.S. Provisional Application No. 60/336,436, filed Nov. 1, 2001 and U.S. Provisional Application No. 60/369,260, filed Apr. 2, 2002. U.S. patent application Ser. Nos. 11/482,220, 10/682,379 and 10/287,432 and U.S. Provisional Application Nos. 60/442,693, 60/487,979, 60/336,436, and 60/369,260 are incorporated in their entireties by reference herein.

BACKGROUND OF THE INVENTION

Field of the Invention

The present invention relates in general to phototherapy, and more particularly, to novel apparatuses and methods for phototherapy of brain tissue affected by stroke.

Description of the Related Art

Stroke, also called cerebrovascular accident (CVA), is a sudden disruption of blood flow to a discrete area of the brain that is brought on by a clot lodging in an artery supplying that area of that brain, or by a cerebral hemorrhage due to a ruptured aneurysm or a burst artery. The consequence of stroke is a loss of function in the affected brain region and concomitant loss of bodily function in areas of the body controlled by the affected brain region. Depending upon the extent and location of the primary insult in the brain, loss of function varies greatly from mild or severe, and may be temporary or permanent. Lifestyle factors such as smoking, diet, level of physical activity and high cholesterol increase the risk of stroke, and thus stroke is a major cause of human suffering in developed nations. Stroke is the third leading cause of death in most developed nations, including the United States.

Until recently, stroke treatment was restricted to providing basic life support at the time of the stroke, followed by rehabilitation. Recently, new drug therapies have taken the approach of breaking up blood clots or protecting surviving at-risk neurons from further damage.

Thrombolytic therapy includes aspirin or intravenous heparin to prevent further clot formation and to maintain blood flow after an ischemic stroke. Thrombolytic drugs include tissue plasminogen activator (TPA) and genetically engineered versions thereof, and streptokinase. However, streptokinase does not appear to improve the patient's outlook unless administered early (within three hours of stroke). TPA when administered early appears to substantially improve prognosis, but slightly increases the risk of death from hemorrhage. In addition, over half of stroke patients arrive at the hospital more than three hours after a stroke, and even if they arrive quickly, a CT scan must first confirm that the stroke is not hemorrhagic, which delays administration of the drug. Also, patients taking aspirin or other blood thinners and patients with clotting abnormalities should not be given TPA.

Neuroprotective drugs target surviving but endangered neurons in a zone of risk surrounding the area of primary infarct. Such drugs are aimed at slowing down or preventing the death of such neurons, to reduce the extent of brain damage. Certain neuroprotective drugs are anti-excitotoxic, i.e., work to block the excitotoxic effects of excitatory amino acids such as glutamate that cause cell membrane damage under certain conditions. Other drugs such as citicoline work by repairing damaged cell membranes. Lazaroids such as Tirilazed (Freedox) counteract oxidative stress produced by oxygen-free radicals produced during stroke. Other drugs for stroke treatment include agents that block the enzyme known as PARP, and calcium-channel blockers such as nimodipine (Nimotop) that relax the blood vessels to prevent vascular spasms that further limit blood supply. However, the effect of nimodipine is reduced if administered beyond six hours after a stroke and it is not useful for ischemic stroke. In addition, drug therapy includes the risk of adverse side effects and immune responses.

Surgical treatment for stroke includes carotid endarterectomy, which appears to be especially effective for reducing the risk of stroke recurrence for patients exhibiting arterial narrowing of more than 70%. However, endarterectomy is highly invasive, and risk of stroke recurrence increases temporarily after surgery. Experimental stroke therapies include an angiography-type or angioplasty-type procedure using a thin catheter to remove or reduce the blockage from a clot. However, such procedures have extremely limited availability and increase the risk of embolic stroke. Other surgical interventions, such as those to repair an aneurysm before rupture remain controversial because of disagreement over the relative risks of surgery versus leaving the aneurysm untreated.

Against this background, a high level of interest remains in finding new and improved therapeutic apparatuses and methods for the treatment of stroke. In particular, a need remains for relatively inexpensive and non-invasive approaches to treating stroke that also avoid the limitations of drug therapy.

SUMMARY OF THE INVENTION

One aspect of the present invention provides a therapy apparatus for treating a patient's brain. The therapy apparatus comprises a light source having an output emission area positioned to irradiate a portion of the brain with an efficacious power density and wavelength of light. The therapy apparatus further comprises an element interposed between the light source and the patient's scalp. The element is adapted to inhibit temperature increases at the scalp caused by the light.

Another aspect of the present invention provides a therapy apparatus for treating brain tissue. The therapy apparatus comprises a light source positioned to irradiate at least a portion of a patient's head with light. The light has a wavelength and power density which penetrates the cranium to deliver an efficacious amount of light to brain tissue. The therapy apparatus further comprises a material which inhibits temperature increases of the head.

Another aspect of the present invention provides a therapy apparatus for treating a patient's brain. The therapy apparatus comprises a light source adapted to irradiate at least a portion of the brain with an efficacious power density and wavelength of light. The therapy apparatus further comprises an element adapted to inhibit temperature increases at the scalp. At least a portion of the element is in an optical path of the light from the light source to the scalp.

Another aspect of the present invention provides a therapy apparatus for treating a patient's brain. The therapy apparatus comprises a light source adapted to irradiate at least a portion of the brain with an efficacious power density and wavelength of light. The therapy apparatus further comprises a controller for energizing said light source so as to selectively produce a plurality of different irradiation patterns on the patient's scalp. Each of said irradiation patterns is comprised of at least one illumination area that is small compared to the patient's scalp, and at least one non-illuminated area.

Another aspect of the present invention provides a method comprising interposing a head element between a light source and the patient's scalp. The element is comprised of a material which, for an efficacious power density at the brain, inhibits temperature increases at the scalp.

Another aspect of the present invention provides a therapy apparatus for treating a patient's brain. The therapy apparatus comprises a light source adapted to irradiate at least a portion of the brain with an efficacious power density and wavelength of light. The therapy apparatus further comprises a biomedical sensor configured to provide real-time feedback information. The therapy apparatus further comprises a controller coupled to the light source and the biomedical sensor. The controller is configured to adjust said light source in response to the real-time feedback information.

Another aspect of the present invention provides a method of treating brain tissue. The method comprises introducing light of an efficacious power density onto brain tissue by directing light through the scalp of a patient. Directing the light comprises providing a sufficiently large spot size on said scalp to reduce the power density at the scalp below the damage threshold of scalp tissue, while producing sufficient optical power at said scalp to achieve said efficacious power density at said brain tissue.

Another aspect of the present invention provides a method of treating a patient's brain. The method comprises covering at least a significant portion of the patient's scalp with a light-emitting blanket.

Another aspect of the present invention provides a method of treating a patient's brain following a stroke. The method comprises applying low-level light therapy to the brain no earlier than several hours following said stroke.

Another aspect of the present invention provides a method for treating a patient's brain. The method comprises introducing light of an efficacious power density onto a target area of the brain by directing light through the scalp of the patient. The light has a plurality of wavelengths and the efficacious power density is at least 0.01 mW/cm$^2$ at the target area.

Another aspect of the present invention provides a method for treating a patient's brain. The method comprises directing light through the scalp of the patient to a target area of the brain concurrently with applying an electromagnetic field to the brain. The light has an efficacious power density at the target area and the electromagnetic field has an efficacious field strength.

Another aspect of the present invention provides a method for treating a patient's brain. The method comprises directing an efficacious power density of light through the scalp of the patient to a target area of the brain concurrently with applying an efficacious amount of ultrasonic energy to the brain.

Anther aspect of the present invention provides a method of providing a neuroprotective effect in a patient that had an ischemic event in the brain. The method comprises identifying a patient who has experienced an ischemic event in the brain. The method further comprises estimating the time of the ischemic event. The method further comprises commencing administration of a neuroprotective effective amount of light energy to the brain no less than about two hours following the time of the ischemic event.

For purposes of summarizing the present invention, certain aspects, advantages, and novel features of the present invention have been described herein above. It is to be understood, however, that not necessarily all such advantages may be achieved in accordance with any particular embodiment of the present invention. Thus, the present invention may be embodied or carried out in a manner that achieves or optimizes one advantage or group of advantages as taught herein without necessarily achieving other advantages as may be taught or suggested herein.

DETAILED DESCRIPTION OF THE PREFERRED EMBODIMENT

Low level light therapy ("LLLT") or phototherapy involves therapeutic administration of light energy to a patient at lower power outputs than those used for cutting, cauterizing, or ablating biological tissue, resulting in desirable biostimulatory effects while leaving tissue undamaged. In non-invasive phototherapy, it is desirable to apply an efficacious amount of light energy to the internal tissue to be treated using light sources positioned outside the body. (See, e.g., U.S. Pat. No. 6,537,304 to Oron and U.S. patent application Ser. No. 10/353,130, both of which are incorporated in their entireties by reference herein.) However, absorption of the light energy by intervening tissue can limit the amount of light energy delivered to the target tissue site, while heating the intervening tissue. In addition, scattering of the light energy by intervening tissue can limit the power density or energy density delivered to the target tissue site. Brute force attempts to circumvent these effects by increasing the power and/or power density applied to the outside surface of the body can result in damage (e.g., burning) of the intervening tissue.

Non-invasive phototherapy methods are circumscribed by setting selected treatment parameters within specified limits so as to preferably avoid damaging the intervening tissue. A review of the existing scientific literature in this field would cast doubt on whether a set of undamaging, yet efficacious, parameters could be found. However, certain embodiments, as described herein, provide devices and methods which can achieve this goal.

Figure 1:
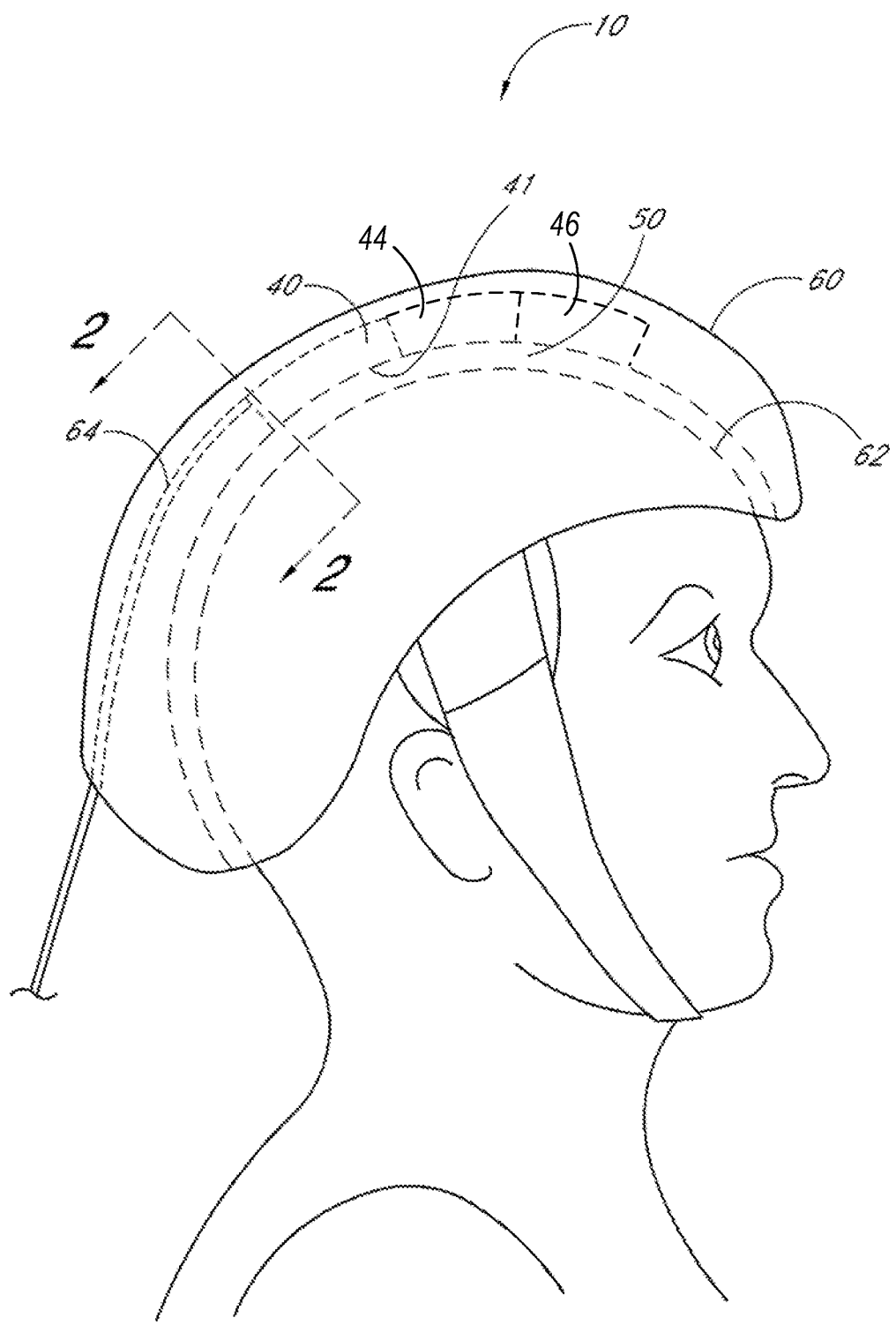
FIG. 1 schematically illustrates a therapy apparatus comprising a cap which fits securely over the patient's head.
Figure 2:
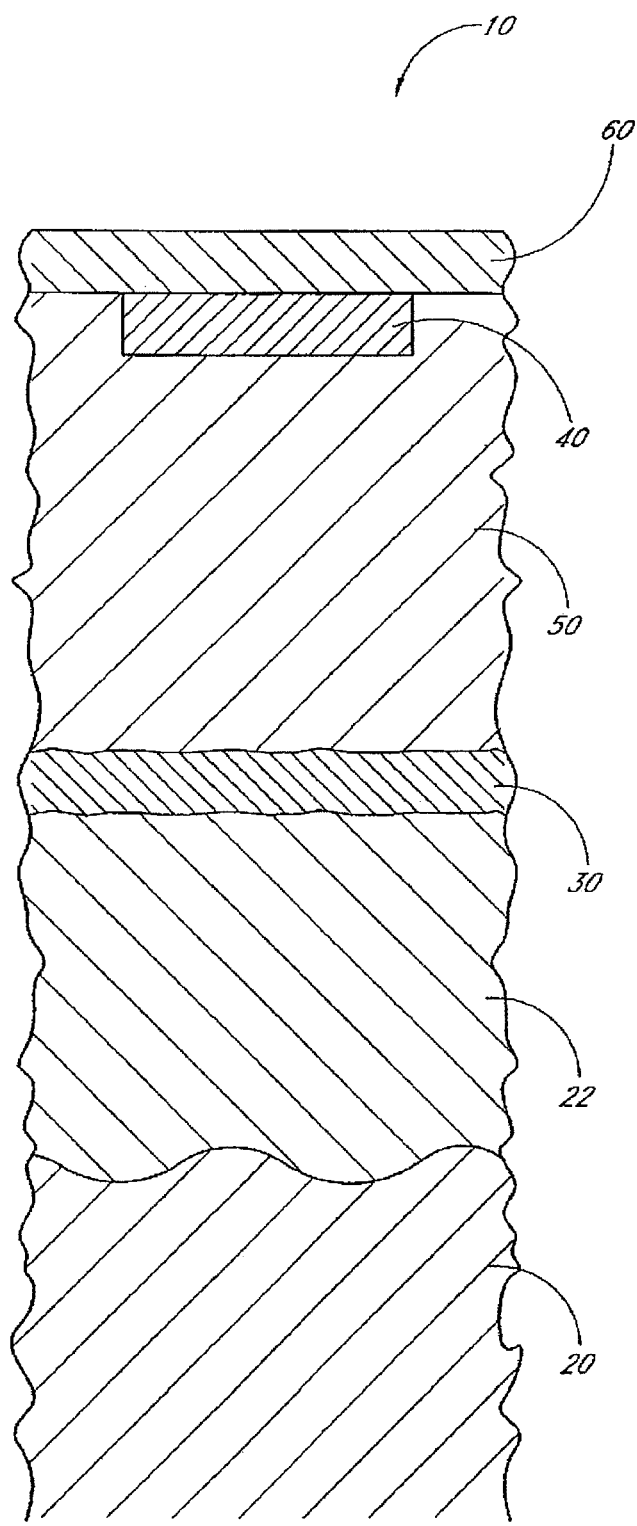
FIG. 2 schematically illustrates a fragmentary cross-sectional view taken along the lines 2-2 of FIG. 1, showing one embodiment of a portion of a therapy apparatus comprising an element and its relationship to the scalp and brain.

Such embodiments may include selecting a wavelength of light at which the absorption by intervening tissue is below a damaging level. Such embodiments may also include setting the power output of the light source at very low, yet efficacious, power densities (e.g., between approximately 100 $\mu$W/cm$^2$ to approximately 10 W/cm$^2$) at the target tissue site, and time periods of application of the light energy at a few seconds to minutes to achieve an efficacious energy density at the target tissue site being treated. Other parameters can also be varied in the use of phototherapy. These other parameters contribute to the light energy that is actually delivered to the treated tissue and may play key roles in the efficacy of phototherapy. In certain embodiments, the irradiated portion of the brain can comprise the entire brain.
Element to Inhibit Temperature Increases at the Scalp FIGS. 1 and 2 schematically illustrate an embodiment of a therapy apparatus 10 for treating a patient's brain 20. The therapy apparatus 10 comprises a light source 40 having an output emission area 41 positioned to irradiate a portion of the brain 20 with an efficacious power density and wavelength of light. The therapy apparatus 10 further comprises an element 50 interposed between the light source 40 and the patient's scalp 30. The element 50 is adapted to inhibit temperature increases at the scalp 30 caused by the light.

As used herein, the term "element" is used in its broadest sense, including, but not limited to, as a reference to a constituent or distinct part of a composite device. In certain embodiments, the element 50 is adapted to contact at least a portion of the patient's scalp 30, as schematically illustrated in FIGS. 1-4. In certain such embodiments, the element 50 is in thermal communication with and covers at least a portion of the scalp 30. In other embodiments, the element 50 is spaced away from the scalp 30 and does not contact the scalp 30.

In certain embodiments, the light passes through the element 50 prior to reaching the scalp 30 such that the element 50 is in the optical path of light propagating from the light source 40, through the scalp 30, through the bones, tissues, and fluids of the head (schematically illustrated in FIG. 1 by the region 22), to the brain 20. In certain embodiments, the light passes through a transmissive medium of the element 50, while in other embodiments, the light passes through an aperture of the element 50. As described more fully below, the element 50 may be utilized with various embodiments of the therapy apparatus 10.

In certain embodiments, the light source 40 is disposed on the interior surface of a cap 60 which fits securely over the patient's head. The cap 60 provides structural integrity for the therapy apparatus 10 and holds the light source 40 and element 50 in place. Exemplary materials for the cap 60 include, but are not limited to, metal, plastic, or other materials with appropriate structural integrity. The cap 60 may include an inner lining 62 comprising a stretchable fabric or mesh material, such as Lycra or nylon. In certain embodiments, the light source 40 is adapted to be removably attached to the cap 60 in a plurality of positions so that the output emission area 41 of the light source 40 can be advantageously placed in a selected position for treatment of a stroke or CVA in any portion of the brain 20. In other embodiments, the light source 40 can be an integral portion of the cap 60.

The light source 40 illustrated by FIGS. 1 and 2 comprises at least one power conduit 64 coupled to a power source (not shown). In some embodiments, the power conduit 64 comprises an electrical conduit which is adapted to transmit electrical signals and power to an emitter (e.g., laser diode or light-emitting diode). In certain embodiments, the power conduit 64 comprises an optical conduit (e.g., optical waveguide) which transmits optical signals and power to the output emission area 41 of the light source 40. In certain such embodiments, the light source 40 comprises optical elements (e.g., lenses, diffusers, and/or waveguides) which transmit at least a portion of the optical power received via the optical conduit 64. In still other embodiments, the therapy apparatus 10 contains a power source (e.g., a battery) and the power conduit 64 is substantially internal to the therapy apparatus 10.

In certain embodiments, the patient's scalp 30 comprises hair and skin which cover the patient's skull. In other embodiments, at least a portion of the hair is removed prior to the phototherapy treatment, so that the therapy apparatus 10 substantially contacts the skin of the scalp 30.

In certain embodiments, the element 50 is adapted to contact the patient's scalp 30, thereby providing an interface between the therapy apparatus 10 and the patient's scalp 30. In certain such embodiments, the element 50 is coupled to the light source 40 and in other such embodiments, the element is also adapted to conform to the scalp 30, as schematically illustrated in FIG. 1. In this way, the element 50 positions the output emission area 41 of the light source 40 relative to the scalp 30. In certain such embodiments, the element 50 is mechanically adjustable so as to adjust the position of the light source 40 relative to the scalp 30. By fitting to the scalp 30 and holding the light source 40 in place, the element 50 inhibits temperature increases at the scalp 30 that would otherwise result from misplacement of the light source 40 relative to the scalp 30. In addition, in certain embodiments, the element 50 is mechanically adjustable so as to fit the therapy apparatus 10 to the patient's scalp 30.

In certain embodiments, the element 50 provides a reusable interface between the therapy apparatus 10 and the patient's scalp 30. In such embodiments, the element 50 can be cleaned or sterilized between uses of the therapy apparatus, particularly between uses by different patients. In other embodiments, the element 50 provides a disposable and replaceable interface between the therapy apparatus 10 and the patient's scalp 30. By using pre-sterilized and pre-packaged replaceable interfaces, certain embodiments can advantageously provide sterilized interfaces without undergoing cleaning or sterilization processing immediately before use.

In certain embodiments, the element 50 comprises a container (e.g., a cavity or bag) containing a material (e.g., gel). The container can be flexible and adapted to conform to the contours of the scalp 30. Other exemplary materials contained in the container of the element 50 include, but are not limited to, thermal exchange materials such as glycerol and water. The element 50 of certain embodiments substantially covers the entire scalp 30 of the patient, as schematically illustrated in FIG. 2. In other embodiments, the element 50 only covers a localized portion of the scalp 30 in proximity to the irradiated portion of the scalp 30.

In certain embodiments, at least a portion of the element 50 is within an optical path of the light from the light source 40 to the scalp 30. In such embodiments, the element 50 is substantially optically transmissive at a wavelength of the light emitted by the output emission area 41 of the light source 40 and is adapted to reduce back reflections of the light. By reducing back reflections, the element 50 increases the amount of light transmitted to the brain 20 and reduces the need to use a higher power light source 40 which may otherwise create temperature increases at the scalp 30. In certain such embodiments, the element 50 comprises one or more optical coatings, films, layers, membranes, etc. in the optical path of the transmitted light which are adapted to reduce back reflections.

In certain such embodiments, the element 50 reduces back reflections by fitting to the scalp 30 so as to substantially reduce air gaps between the scalp 30 and the element 50 in the optical path of the light. The refractive-index mismatches between such an air gap and the element 50 and/or the scalp 30 would otherwise result in at least a portion of the light propagating from the light source 40 to the brain 20 to be reflected back towards the light source 40.

In addition, certain embodiments of the element 50 comprise a material having, at a wavelength of light emitted by the light source 40, a refractive index which substantially matches the refractive index of the scalp 30 (e.g., about 1.3), thereby reducing any index-mismatch-generated back reflections between the element 50 and the scalp 30. Examples of materials with refractive indices compatible with embodiments described herein include, but are not limited to, glycerol, water, and silica gels. Exemplary index-matching gels include, but are not limited to, those available from Nye Lubricants, Inc. of Fairhaven, Mass.

In certain embodiments, the element 50 is adapted to cool the scalp 30 by removing heat from the scalp 30 so as to inhibit temperature increases at the scalp 30. In certain such embodiments, the element 50 comprises a reservoir (e.g., a chamber or a conduit) adapted to contain a coolant. The coolant flows through the reservoir near the scalp 30. The scalp 30 heats the coolant, which flows away from the scalp 30, thereby removing heat from the scalp 30 by active cooling. The coolant in certain embodiments circulates between the element 50 and a heat transfer device, such as a chiller, whereby the coolant is heated by the scalp 30 and is cooled by the heat transfer device. Exemplary materials for the coolant include, but are not limited to, water or air.

Figure 3:
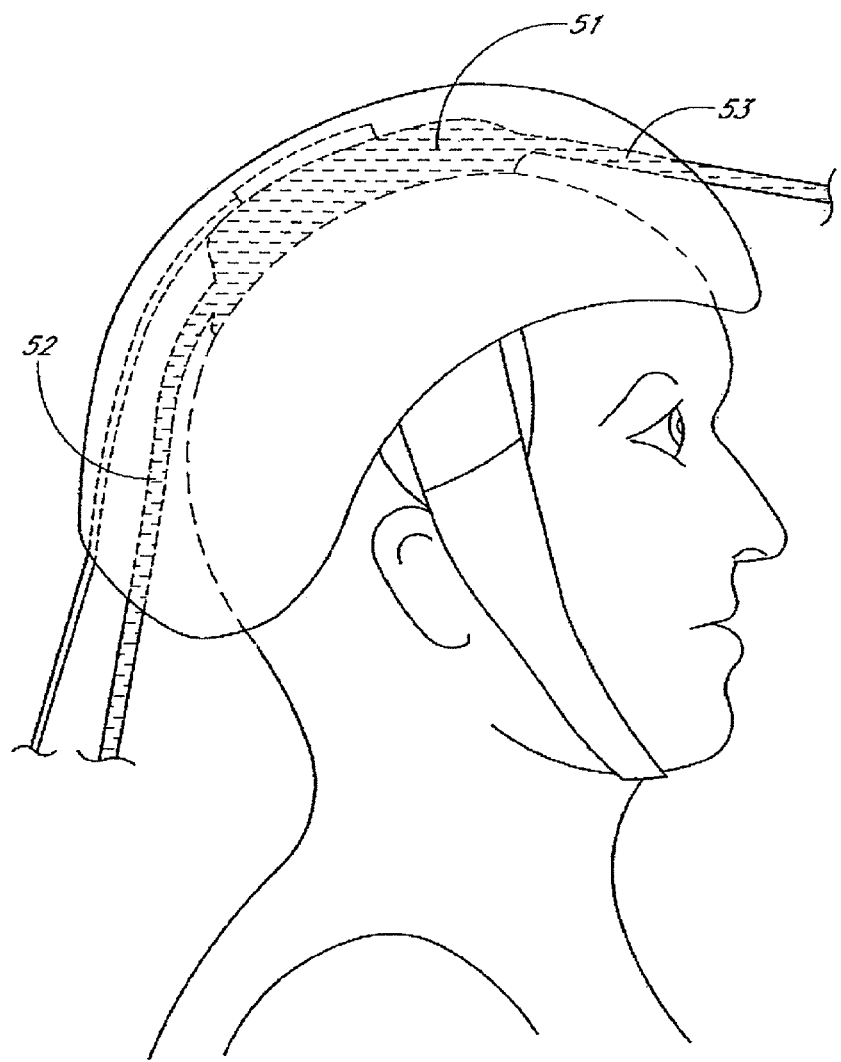
FIG. 3 schematically illustrates an embodiment with an element comprising a container coupled to an inlet conduit and an outlet conduit for the transport of a flowing material through the element.

In certain embodiments, the element 50 comprises a container 51 (e.g., a flexible bag) coupled to an inlet conduit 52 and an outlet conduit 53, as schematically illustrated in FIG. 3. A flowing material (e.g., water, air, or glycerol) can flow into the container 51 from the inlet conduit 52, absorb heat from the scalp 30, and flow out of the container 51 through the outlet conduit 53. Certain such embodiments can provide a mechanical fit of the container 51 to the scalp 30 and sufficient thermal coupling to prevent excessive heating of the scalp 30 by the light. In certain embodiments, the container 51 can be disposable and replacement containers 51 can be used for subsequent patients.

In still other embodiments, the element 50 comprises a container (e.g., a flexible bag) containing a material which does not flow out of the container but is thermally coupled to the scalp 30 so as to remove heat from the scalp 30 by passive cooling. Exemplary materials include, but are not limited to, water, glycerol, and gel. In certain such embodiments, the non-flowing material can be pre-cooled (e.g., by placement in a refrigerator) prior to the phototherapy treatment to facilitate cooling of the scalp 30.

In certain embodiments, the element 50 is adapted to apply pressure to at least a portion of the scalp 30. By applying sufficient pressure, the element 50 can blanch the portion of the scalp 30 by forcing at least some blood out the optical path of the light energy. The blood removal resulting from the pressure applied by the element 50 to the scalp 30 decreases the corresponding absorption of the light energy by blood in the scalp 30. As a result, temperature increases due to absorption of the light energy by blood at the scalp 30 are reduced. As a further result, the fraction of the light energy transmitted to the subdermal target tissue of the brain 20 is increased.

Figure 4A:
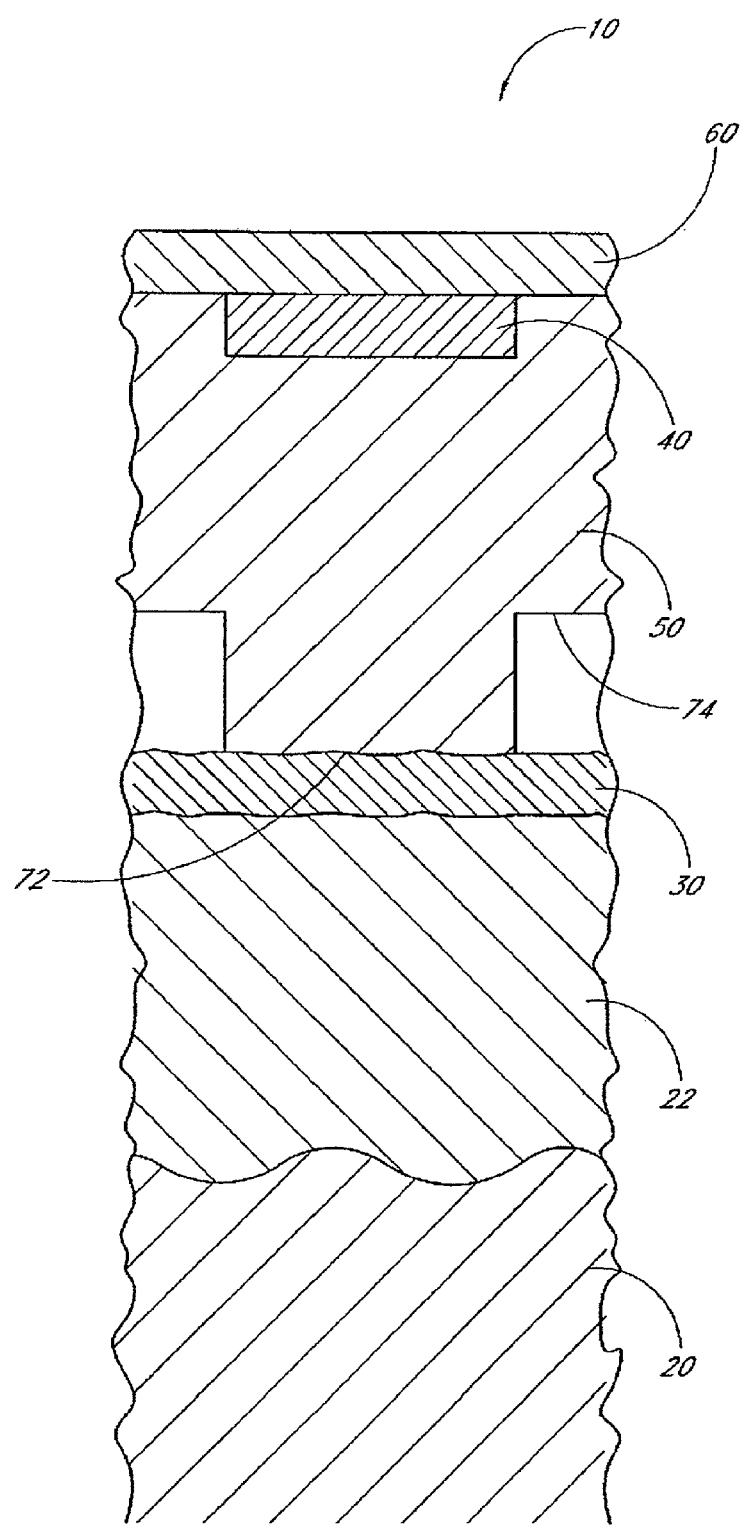
FIG. 4A schematically illustrates a fragmentary cross-sectional view taken along the lines 2-2 of FIG. 1, showing another embodiment of a portion of a therapy apparatus comprising an element with a portion contacting the scalp and a portion spaced away from the scalp.
Figure 4B:
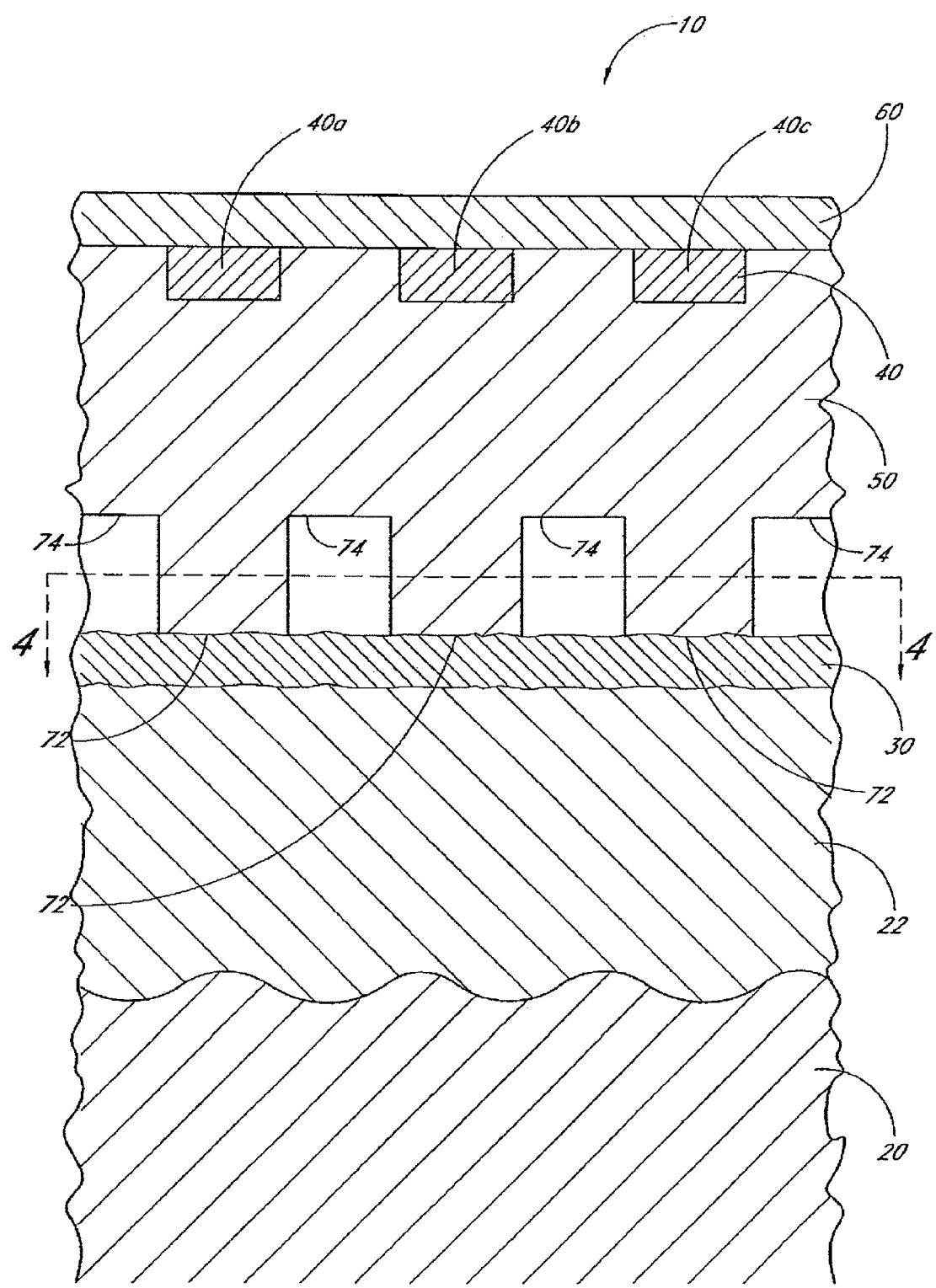
FIG. 4B schematically illustrates a fragmentary cross-sectional view taken along the lines 2-2 of FIG. 1, showing an embodiment of a portion of a therapy apparatus comprising a plurality of light sources and an element with portions contacting the scalp and portions spaced away from the scalp.

FIGS. 4A and 4B schematically illustrate embodiments of the element 50 adapted to facilitate the blanching of the scalp 30. In the cross-sectional view of a portion of the therapy apparatus 10 schematically illustrated in FIG. 4A, certain element portions 72 contact the patient's scalp 30 and other element portions 74 are spaced away from the scalp 30. The element portions 72 contacting the scalp 30 provide an optical path for light to propagate from the light source 40 to the scalp 30. The element portions 72 contacting the scalp 30 also apply pressure to the scalp 30, thereby forcing blood out from beneath the element portion 72. FIG. 4B schematically illustrates a similar view of an embodiment in which the light source 40 comprises a plurality of light sources 40a, 40b, 40c.

Figure 5A:
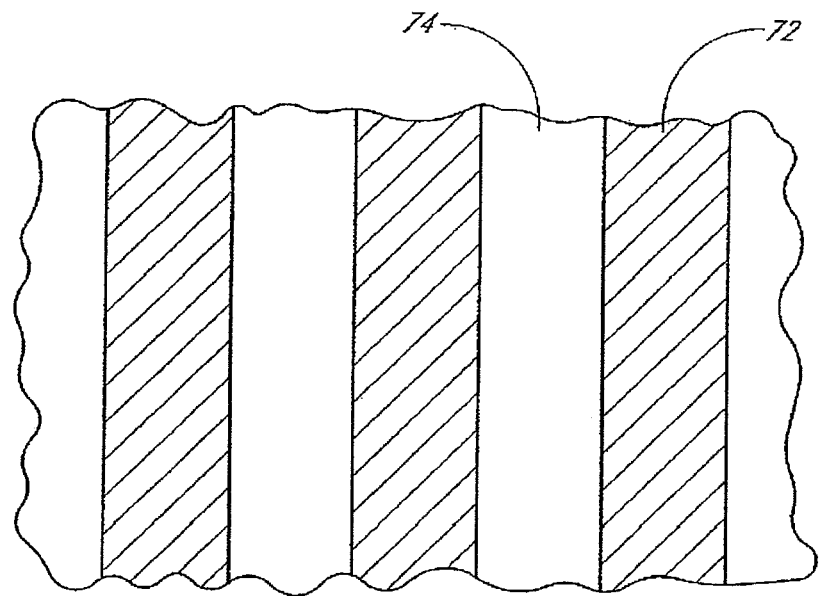
FIGS. 5A and 5B schematically illustrate cross-sectional views of two embodiments of the element in accordance with FIG. 4B taken along the line 4-4.
Figure 5B:
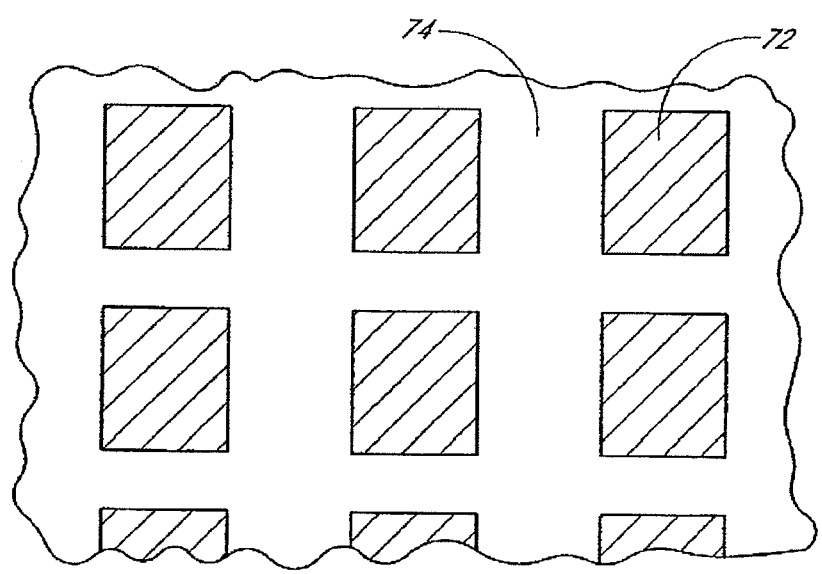

FIG. 5A schematically illustrates one embodiment of the cross-section along the line 4-4 of FIG. 4B. The element portions 72 contacting the scalp 30 comprise ridges extending along one direction, and the element portions 74 spaced away from the scalp 30 comprise troughs extending along the same direction. In certain embodiments, the ridges are substantially parallel to one another and the troughs are substantially parallel to one another. FIG. 5B schematically illustrates another embodiment of the cross-section along the line 4-4 of FIG. 4B. The element portions 72 contacting the scalp 30 comprise a plurality of projections in the form of a grid or array. More specifically, the portions 72 are rectangular and are separated by element portions 74 spaced away from the scalp 30, which form troughs extending in two substantially perpendicular directions. The portions 72 of the element 50 contacting the scalp 30 can be a substantial fraction of the total area of the element 50 or of the scalp 30.

Figure 6A:
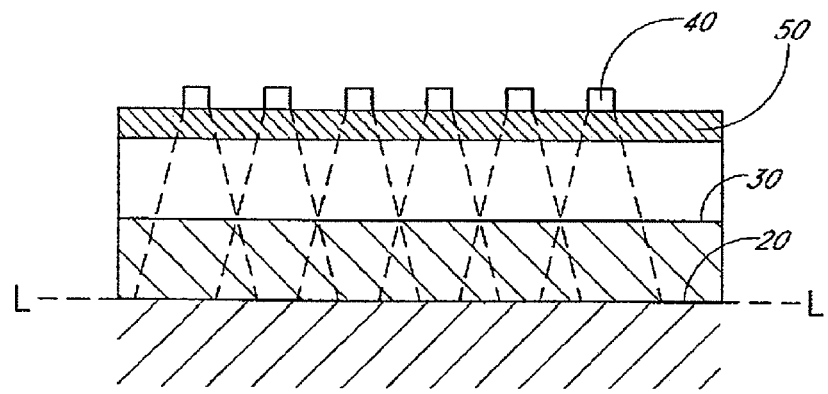
FIGS. 6A-6C schematically illustrate an embodiment in which the light sources are spaced away from the scalp.
Figure 6B:
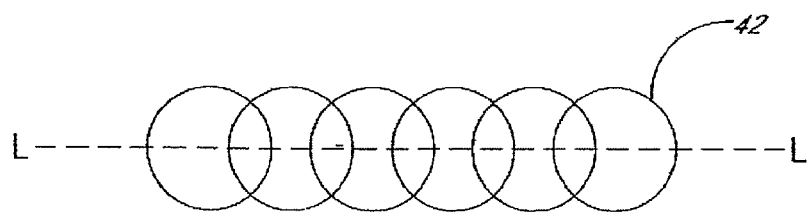
Figure 6C:
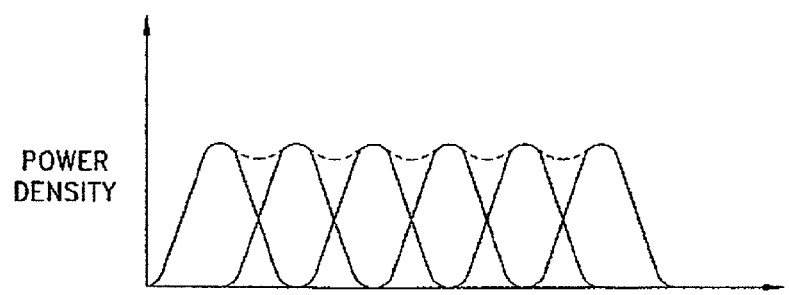

FIGS. 6A-6C schematically illustrate an embodiment in which the light sources 40 are spaced away from the scalp 30. In certain such embodiments, the light emitted by the light sources 40 propagates from the light sources 40 through the scalp 30 to the brain 20 and disperses in a direction generally parallel to the scalp 30, as shown in FIG. 6A. The light sources 40 are preferably spaced sufficiently far apart from one another such that the light emitted from each light source 40 overlaps with the light emitted from the neighboring light sources 40 at the brain 20. FIG. 6B schematically illustrates this overlap as the overlap of circular spots 42 at a reference depth at or below the surface of the brain 20. FIG. 6C schematically illustrates this overlap as a graph of the power density at the reference depth of the brain 20 along the line L-L of FIGS. 6A and 6B. Summing the power densities from the neighboring light sources 40 (shown as a dashed line in FIG. 6C) serves to provide a more uniform light distribution at the tissue to be treated. In such embodiments, the summed power density is preferably less than a damage threshold of the brain 20 and above an efficacy threshold.

Figure 7A:
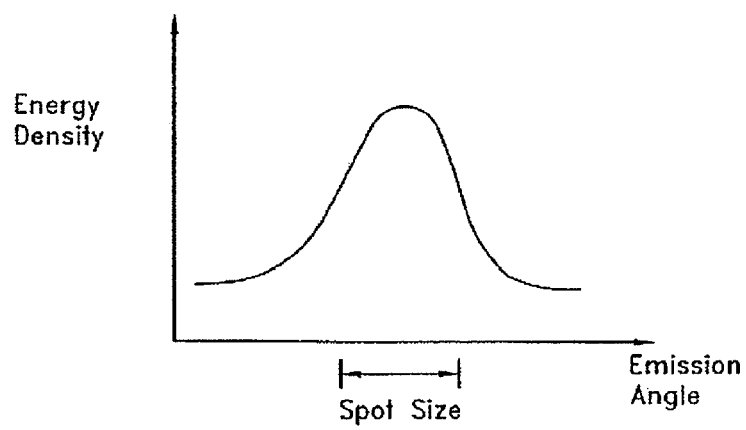
FIGS. 7A and 7B schematically illustrate the diffusive effect on the light by the element.
Figure 7B:
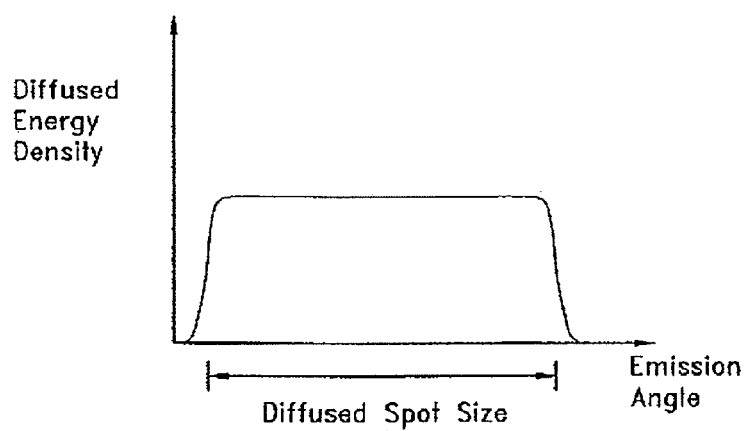

In certain embodiments, the element 50 is adapted to diffuse the light prior to reaching the scalp 30. FIGS. 7A and 7B schematically illustrate the diffusive effect on the light by the element 50. An exemplary energy density profile of the light emitted by a light source 40, as illustrated by FIG. 7A, is peaked at a particular emission angle. After being diffused by the element 50, as illustrated by FIG. 7B, the energy density profile of the light does not have a substantial peak at any particular emission angle, but is substantially evenly distributed among a range of emission angles. By diffusing the light emitted by the light source 40, the element 50 distributes the light energy substantially evenly over the area to be illuminated, thereby inhibiting "hot spots" which would otherwise create temperature increases at the scalp 30. In addition, by diffusing the light prior to its reaching the scalp 30, the element 50 can effectively increase the spot size of the light impinging the scalp 30, thereby advantageously lowering the power density at the scalp 30, as described more fully below. In addition, in embodiments with multiple light sources 40, the element 50 can diffuse the light to alter the total light output distribution to reduce inhomogeneities.

In certain embodiments, the element 50 provides sufficient diffusion of the light such that the power density of the light is less than a maximum tolerable level of the scalp 30 and brain 20. In certain other embodiments, the element 50 provides sufficient diffusion of the light such that the power density of the light equals a therapeutic value at the target tissue. The element 50 can comprise exemplary diffusers including, but are not limited to, holographic diffusers such as those available from Physical Optics Corp. of Torrance, Calif. and Display Optics P/N SN1333 from Reflexite Corp. of Avon, Conn.

Power Density

Phototherapy for the treatment of stroke is based in part on the discovery that power density (i.e., power per unit area or number of photons per unit area per unit time) and energy density (i.e., energy per unit area or number of photons per unit area) of the light energy applied to tissue appear to be significant factors in determining the relative efficacy of low level phototherapy. This discovery is particularly applicable with respect to treating and saving surviving but endangered neurons in a zone of danger surrounding the primary infarct after a stroke or cerebrovascular accident (CVA). Preferred methods described herein are based at least in part on the finding that, given a selected wavelength of light energy, it is the power density and/or the energy density of the light delivered to tissue (as opposed to the total power or total energy delivered to the tissue) that appears to be important factors in determining the relative efficacy of phototherapy.

Without being bound by theory, it is believed that light energy delivered within a certain range of power densities and energy densities provides the desired biostimulative effect on the intracellular environment, such that proper function is returned to previously nonfunctioning or poorly functioning mitochondria in at-risk neurons. The biostimulative effect may include interactions with chromophores within the target tissue, which facilitate production of ATP thereby feeding energy to injured cells which have experienced decreased blood flow due to the stroke. Because strokes correspond to blockages or other interruptions of blood flow to portions of the brain, it is thought that any effects of increasing blood flow by phototherapy are of less importance in the efficacy of phototherapy for stroke victims. Further information regarding the role of power density and exposure time is described by Hans H. F. I. van Breugel and P. R. Dop Bar in "Power Density and Exposure Time of He—Ne Laser Irradiation Are More Important Than Total Energy Dose in Photo-Biomodulation of Human Fibroblasts In Vitro," Lasers in Surgery and Medicine, Volume 12, pp. 528-537 (1992), which is incorporated in its entirety by reference herein.

Figure 8B:
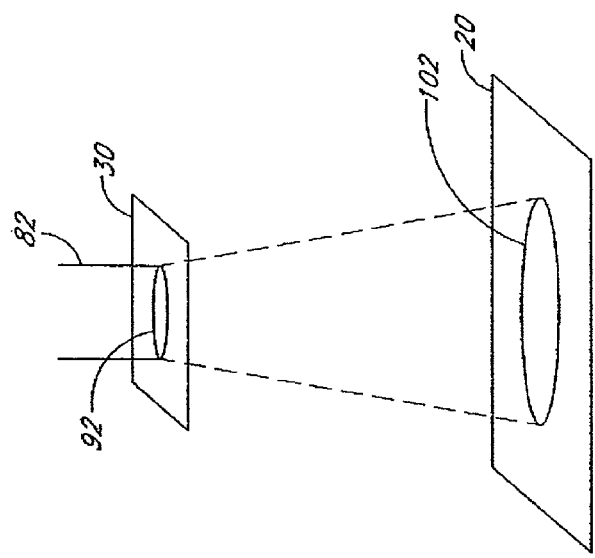
FIGS. 8A and 8B schematically illustrate two light beams having different cross-sections impinging a patient's scalp and propagating through the patient's head to irradiate a portion of the patient's brain tissue.
Figure 8A:
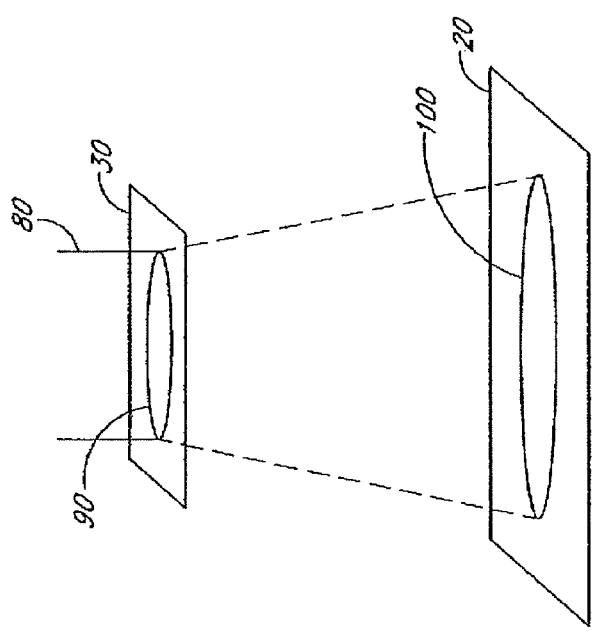

The significance of the power density used in phototherapy has ramifications with regard to the devices and methods used in phototherapy of brain tissue, as schematically illustrated by FIGS. 8A and 8B, which show the effects of scattering by intervening tissue. Further information regarding the scattering of light by tissue is provided by V. Tuchin in "Tissue Optics: Light Scattering Methods and Instruments for Medical Diagnosis," SPIE Press (2000), Bellingham, Wash., pp. 3-11, which is incorporated in its entirety by reference herein.

FIG. 8A schematically illustrates a light beam 80 impinging a portion 90 of a patient's scalp 30 and propagating through the patient's head to irradiate a portion 100 of the patient's brain tissue 20. In the exemplary embodiment of FIG. 8A, the light beam 80 impinging the scalp 30 is collimated and has a circular cross-section with a radius of 2 cm and a cross-sectional area of approximately 12.5 $cm^2$. For comparison purposes, FIG. 8B schematically illustrates a light beam 82 having a significantly smaller cross-section impinging a smaller portion 92 of the scalp 30 to irradiate a portion 102 of the brain tissue 20. The light beam 82 impinging the scalp 30 in FIG. 8B is collimated and has a circular cross-section with a radius of 1 cm and a cross-sectional area of approximately 3.1 $cm^2$. The collimations, cross-sections, and radii of the light beams 80, 82 illustrated in FIGS. 8A and 8B are exemplary; other light beams with other parameters are also compatible with embodiments described herein. In particular, similar considerations apply to focussed beams or diverging beams, as they are similarly scattered by the intervening tissue.

As shown in FIGS. 8A and 8B, the cross-sections of the light beams 80, 82 become larger while propagating through the head due to scattering from interactions with tissue of the head. Assuming that the angle of dispersion is 15 degrees and the irradiated brain tissue 20 is 2.5 cm below the scalp 30, the resulting area of the portion 100 of brain tissue 20 irradiated by the light beam 80 in FIG. 8A is approximately 22.4 $cm^2$. Similarly, the resulting area of the portion 102 of brain tissue 20 irradiated by the light beam 82 in FIG. 8B is approximately 8.8 $cm^2$.

Irradiating the portion 100 of the brain tissue 20 with a power density of 10 mW/cm² corresponds to a total power within the portion 100 of approximately 224 mW (10 mW/cm²×22.4 cm²). Assuming only approximately 5% of the light beam 80 is transmitted between the scalp 30 and the brain tissue 20, the incident light beam 80 at the scalp 30 will have a total power of approximately 4480 mW (224 mW/0.05) and a power density of approximately 358 mW/cm² (4480 mW/12.5 cm²). Similarly, irradiating the portion 102 of the brain tissue 20 with a power density of 10 mW/cm² corresponds to a total power within the portion 102 of approximately 88 mW (10 mW/cm²×8.8 cm²), and with the same 5% transmittance, the incident light beam 82 at the scalp 30 will have a total power of approximately 1760 mW (88 mW/0.05) and a power density of approximately 568 mW/cm² (1760 mW/3.1 cm²). These calculations are summarized in Table 1.

TABLE 1

|  | 2 cm Spot Size (FIG. 8A) | 1 cm Spot Size (FIG. 8B) |
|---|---|---|
| Scalp: | | |
| Area | 12.5 cm² | 3.1 cm² |
| Total power | 4480 mW | 1760 mW |
| Power density | 358 mW/cm² | 568 mW/cm² |
| Brain: | | |
| Area | 22.4 cm² | 8.8 cm² |
| Total power | 224 mW | 88 mW |
| Power density | 10 mW/cm² | 10 mW/cm² |

These exemplary calculations illustrate that to obtain a desired power density at the brain 20, higher total power at the scalp 30 can be used in conjunction with a larger spot size at the scalp 30. Thus, by increasing the spot size at the scalp 30, a desired power density at the brain 20 can be achieved with lower power densities at the scalp 30 which can reduce the possibility of overheating the scalp 30. In certain embodiments, the light can be directed through an aperture to define the illumination of the scalp 30 to a selected smaller area.

Light Source

The light source 40 preferably generates light in the visible to near-infrared wavelength range. In certain embodiments, the light source 40 comprises one or more laser diodes, which each provide coherent light. In embodiments in which the light from the light source 40 is coherent, the emitted light may produce "speckling" due to coherent interference of the light. This speckling comprises intensity spikes which are created by constructive interference and can occur in proximity to the target tissue being treated. For example, while the average power density may be approximately 10 mW/cm², the power density of one such intensity spike in proximity to the brain tissue to be treated may be approximately 300 mW/cm². In certain embodiments, this increased power density due to speckling can improve the efficacy of treatments using coherent light over those using incoherent light for illumination of deeper tissues.

In other embodiments, the light source 40 provides incoherent light. Exemplary light sources 40 of incoherent light include, but are not limited to, incandescent lamps or light-emitting diodes. A heat sink can be used with the light source 40 (for either coherent or incoherent sources) to remove heat from the light source 40 and to inhibit temperature increases at the scalp 30.

In certain embodiments, the light source 40 generates light which is substantially monochromatic (i.e., light having one wavelength, or light having a narrow band of wavelengths). So that the amount of light transmitted to the brain is maximized, the wavelength of the light is selected in certain embodiments to be at or near a transmission peak (or at or near an absorption minimum) for the intervening tissue. In certain such embodiments, the wavelength corresponds to a peak in the transmission spectrum of tissue at about 820 nanometers. In other embodiments, the wavelength of the light is preferably between about 630 nanometers and about 1064 nanometers, more preferably between about 780 nanometers and about 840 nanometers, and most preferably includes wavelengths of about 790, 800, 810, 820, or 830 nanometers. It has also been found that an intermediate wavelength of about 739 nanometers appears to be suitable for penetrating the skull, although other wavelengths are also suitable and may be used.

In other embodiments, the light source 40 generates light having a plurality of wavelengths. In certain such embodiments, each wavelength is selected so as to work with one or more chromophores within the target tissue. Without being bound by theory, it is believed that irradiation of chromophores increases the production of ATP in the target tissue, thereby producing beneficial effects. In certain embodiments, the light source 40 is adapted to generate light having a first wavelength concurrently with light having a second wavelength. In certain other embodiments, the light source 40 is adapted to generate light having a first wavelength sequentially with light having a second wavelength.

In certain embodiments, the light source 40 includes at least one continuously emitting GaAlAs laser diode having a wavelength of about 830 nanometers. In another embodiment, the light source 40 comprises a laser source having a wavelength of about 808 nanometers. In still other embodiments, the light source 40 includes at least one vertical cavity surface-emitting laser (VCSEL) diode. Other light sources 40 compatible with embodiments described herein include, but are not limited to, light-emitting diodes (LEDs) and filtered lamps.

The light source 40 is capable of emitting light energy at a power sufficient to achieve a predetermined power density at the subdermal target tissue (e.g., at a depth of approximately 2 centimeters from the dura). It is presently believed that phototherapy of tissue is most effective when irradiating the target tissue with power densities of light of at least about 0.01 mW/cm² and up to about 1 W/cm². In various embodiments, the subsurface power density is at least about 0.01, 0.05, 0.1, 0.5, 1, 5, 10, 15, 20, 30, 40, 50, 60, 70, 80, or 90 mW/cm², respectively, depending on the desired clinical performance. In certain embodiments, the subsurface power density is preferably about 0.01 mW/cm² to about 100 mW/cm², more preferably about 0.01 mW/cm² to about 50 mW/cm², and most preferably about 2 mW/cm² to about 20 mW/cm². It is believed that these subsurface power densities are especially effective at producing the desired biostimulative effects on the tissue being treated.

Taking into account the attenuation of energy as it propagates from the skin surface, through body tissue, bone, and fluids, to the subdermal target tissue, surface power densities preferably between about 10 mW/cm² to about 10 W/cm², or more preferably between about 100 mW/cm² to about 500 mW/cm², will typically be used to attain the selected power densities at the subdermal target tissue. To achieve such surface power densities, the light source 40 is preferably capable of emitting light energy having a total power output of at least about 25 mW to about 100 W. In various embodiments, the total power output is limited to be no more than about 30, 50, 75, 100, 150, 200, 250, 300, 400, or 500 mW, respectively. In certain embodiments, the light source 40 comprises a plurality of sources used in combination to provide the total power output. The actual power output of the light source 40 is preferably controllably variable. In this way, the power of the light energy emitted can be adjusted in accordance with a selected power density at the subdermal tissue being treated.

Certain embodiments utilize a light source 40 that includes only a single laser diode that is capable of providing about 25 mW to about 100 W of total power output at the skin surface. In certain such embodiments, the laser diode can be optically coupled to the scalp 30 via an optical fiber or can be configured to provide a sufficiently large spot size to avoid power densities which would burn or otherwise damage the scalp 30. In other embodiments, the light source 40 utilizes a plurality of sources (e.g., laser diodes) arranged in a grid or array that together are capable of providing at least about 25 mW to about 100 W of total power output at the skin surface. The light source 40 of other embodiments may also comprise sources having power capacities outside of these limits.

Figure 9A:
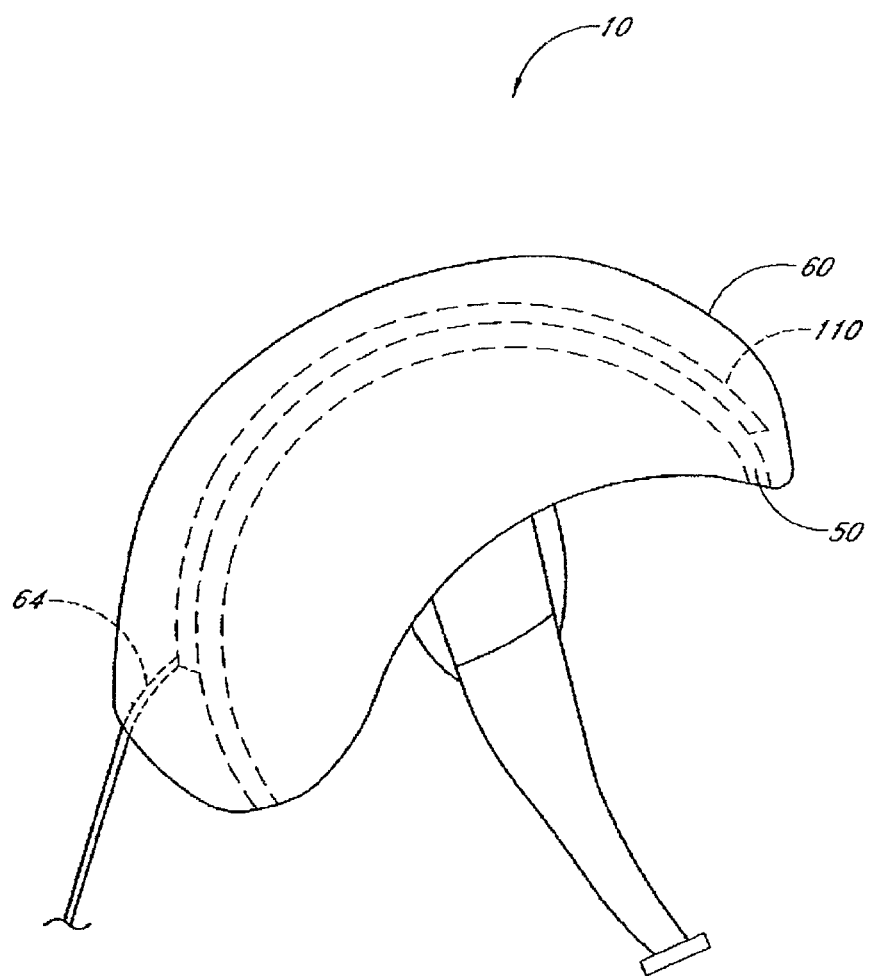
FIG. 9A schematically illustrates a therapy apparatus comprising a cap and a light source comprising a light blanket.
Figure 9B:
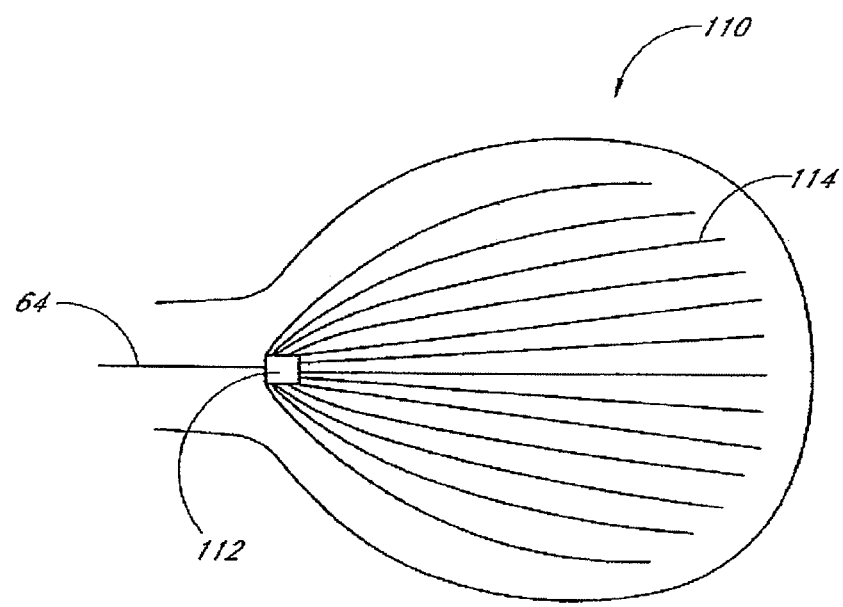
FIGS. 9B and 9C schematically illustrate two embodiments of the light blanket.
Figure 9C:
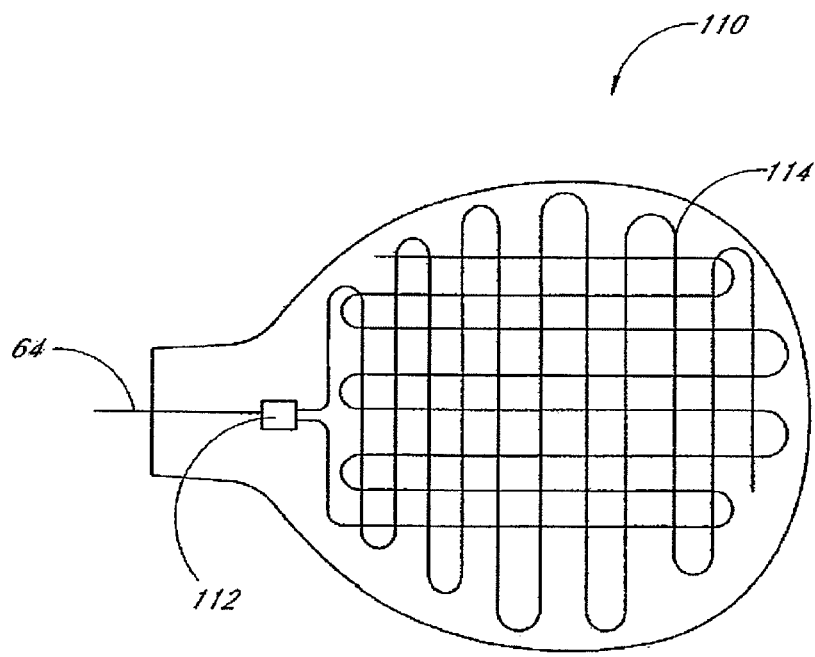

FIG. 9A schematically illustrates another embodiment of the therapy apparatus 10 which comprises the cap 60 and a light source comprising a light-emitting blanket 110. FIG. 9B schematically illustrates an embodiment of the blanket 110 comprising a flexible substrate 111 (e.g., flexible circuit board), a power conduit interface 112, and a sheet formed by optical fibers 114 positioned in a fan-like configuration. FIG. 9C schematically illustrates an embodiment of the blanket 110 comprising a flexible substrate 111, a power conduit interface 112, and a sheet formed by optical fibers 114 woven into a mesh. The blanket 110 is preferably positioned within the cap 60 so as to cover an area of the scalp 30 corresponding to a portion of the brain 20 to be treated.

In certain such embodiments, the power conduit interface 112 is adapted to be coupled to an optical fiber conduit 64 which provides optical power to the blanket 110. The optical power interface 112 of certain embodiments comprises a beam splitter or other optical device which distributes the incoming optical power among the various optical fibers 114. In other embodiments, the power conduit interface 112 is adapted to be coupled to an electrical conduit which provides electrical power to the blanket 110. In certain such embodiments, the power conduit interface 112 comprises one or more laser diodes, the output of which is distributed among the various optical fibers 114 of the blanket 110. In certain other embodiments, the blanket 110 comprises an electroluminescent sheet which responds to electrical signals from the power conduit interface 112 by emitting light. In such embodiments, the power conduit interface 112 comprises circuitry adapted to distribute the electrical signals to appropriate portions of the electroluminescent sheet.

The side of the blanket 110 nearer the scalp 30 is preferably provided with a light scattering surface, such as a roughened surface to increase the amount of light scattered out of the blanket 110 towards the scalp 30. The side of the blanket 110 further from the scalp 30 is preferably covered by a reflective coating so that light emitted away from the scalp 30 is reflected back towards the scalp 30. This configuration is similar to configurations used for the "back illumination" of liquid-crystal displays (LCDs). Other configurations of the blanket 110 are compatible with embodiments described herein.

In certain embodiments, the light source 40 generates light which cause eye damage if viewed by an individual. In such embodiments, the apparatus 50 can be configured to provide eye protection so as to avoid viewing of the light by individuals. For example, opaque materials can be appropriately placed to block the light from being viewed directly. In addition, interlocks can be provided so that the light source 40 is not activated unless the apparatus 50 is in place, or other appropriate safety measures are taken.

Light Delivery Apparatuses

The phototherapy methods for the treatment of stroke described herein may be practiced and described using, for example, a low level laser therapy apparatus such as that shown and described in U.S. Pat. Nos. 6,214,035, 6,267,780, 6,273,905 and 6,290,714, which are all incorporated in their entirety by reference herein, as are the references incorporated by reference therein.

Figure 10:
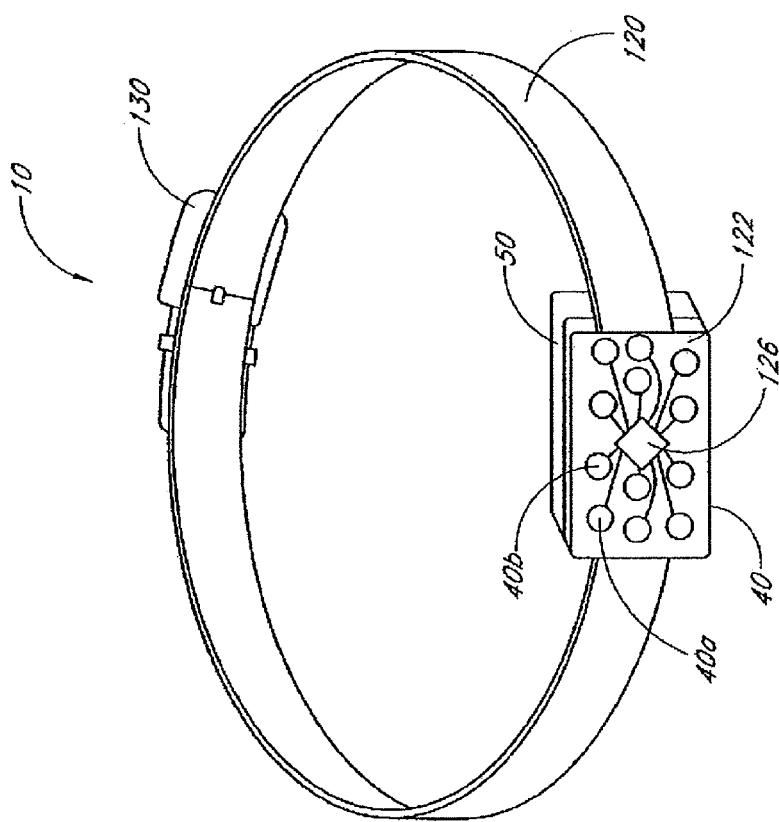
FIG. 10 schematically illustrates a therapy apparatus comprising a flexible strap and a housing.

Another suitable phototherapy apparatus in accordance with embodiments described here is illustrated in FIG. 10. The illustrated therapy apparatus 10 includes a light source 40, an element 50, and a flexible strap 120 adapted for securing the therapy apparatus 10 over an area of the patient's head. The light source 40 can be disposed on the strap 120 itself, or in a housing 122 coupled to the strap 120. The light source 40 preferably comprises a plurality of diodes 40a, 40b, . . . capable of emitting light energy having a wavelength in the visible to near-infrared wavelength range. The element 50 is adapted to be positioned between the light source 40 and the patient's scalp 30.

The therapy apparatus 10 further includes a power supply (not shown) operatively coupled to the light source 40, and a programmable controller 126 operatively coupled to the light source 40 and to the power supply. The programmable controller 126 is configured to control the light source 40 so as to deliver a predetermined power density to the brain tissue 20. In certain embodiments, as schematically illustrated in FIG. 10, the light source 40 comprises the programmable controller 126. In other embodiments the programmable controller 126 is a separate component of the therapy apparatus 10.

In certain embodiments, the strap 120 comprises a loop of elastomeric material sized appropriately to fit snugly onto the patient's scalp 30. In other embodiments, the strap 120 comprises an elastomeric material to which is secured any suitable securing means 130, such as mating Velcro strips, buckles, snaps, hooks, buttons, ties, or the like. The precise configuration of the strap 120 is subject only to the limitation that the strap 120 is capable of maintaining the light source 40 in a selected position so that light energy emitted by the light source 40 is directed towards the targeted brain tissue 20.

In the exemplary embodiment illustrated in FIG. 10, the housing 122 comprises a layer of flexible plastic or fabric that is secured to the strap 120. In other embodiments, the housing 122 comprises a plate or an enlarged portion of the strap 120. Various strap configurations and spatial distributions of the light sources 40 are compatible with embodiments described herein so that the therapy apparatus 10 can treat selected portions of brain tissue.

Figure 11:
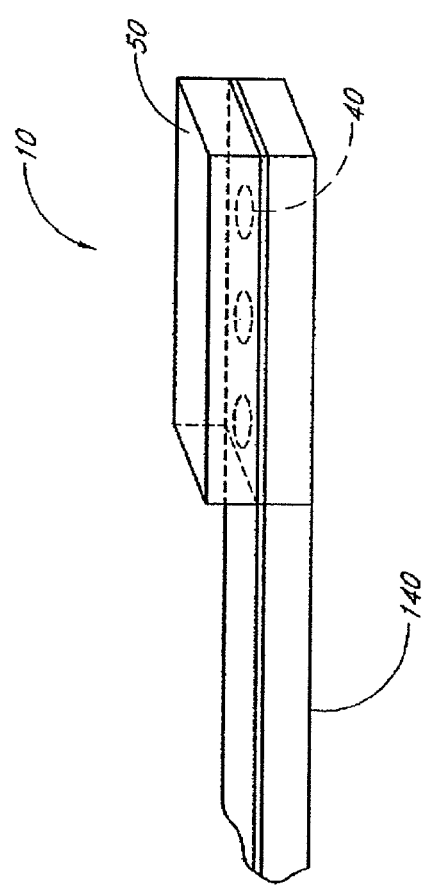
FIG. 11 schematically illustrates a therapy apparatus comprising a handheld probe.

In still other embodiments, the therapy apparatus 10 for delivering the light energy includes a handheld probe 140, as schematically illustrated in FIG. 11. The probe 140 includes a light source 40 and an element 50 as described herein.

Figure 12:
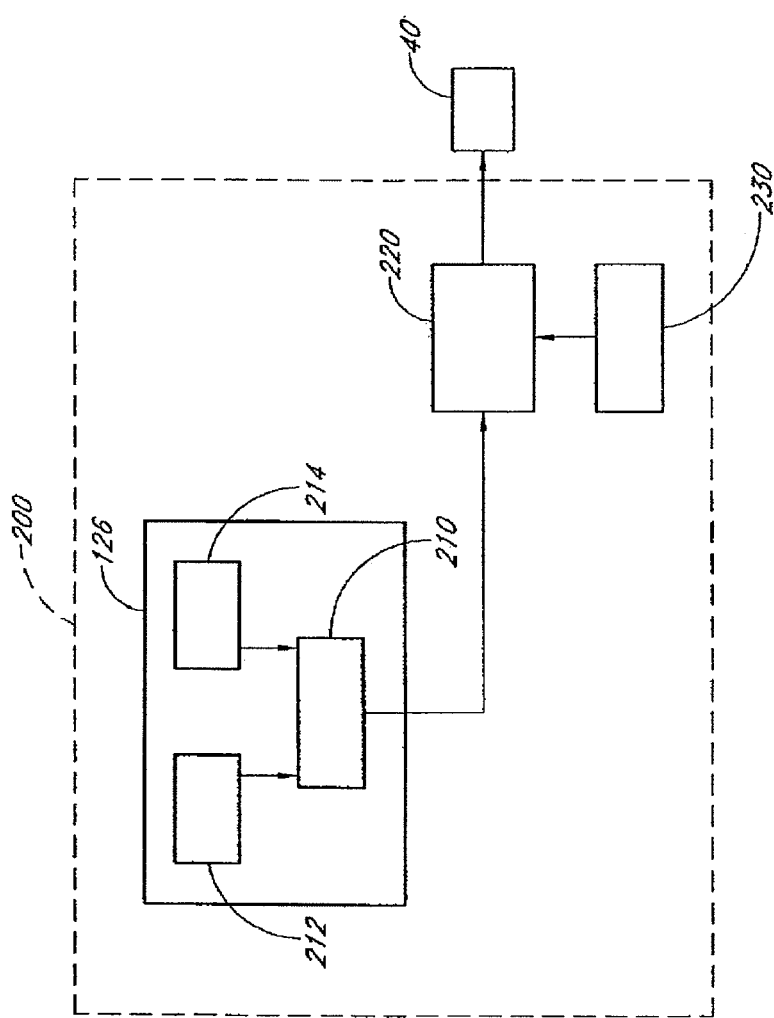
FIG. 12 is a block diagram of a control circuit comprising a programmable controller.

FIG. 12 is a block diagram of a control circuit 200 comprising a programmable controller 126 according to embodiments described herein. The control circuit 200 is configured to adjust the power of the light energy emitted by the light source 40 to generate a predetermined surface power density at the scalp 30 corresponding to a predetermined energy delivery profile, such as a predetermined subsurface power density, to the target area of the brain 20.

In certain embodiments, the programmable controller 126 comprises a logic circuit 210, a clock 212 coupled to the logic circuit 210, and an interface 214 coupled to the logic circuit 210. The clock 212 of certain embodiments provides a timing signal to the logic circuit 210 so that the logic circuit 210 can monitor and control timing intervals of the applied light. Examples of timing intervals include, but are not limited to, total treatment times, pulsewidth times for pulses of applied light, and time intervals between pulses of applied light. In certain embodiments, the light sources 40 can be selectively turned on and off to reduce the thermal load on the scalp 30 and to deliver a selected power density to particular areas of the brain 20.

The interface 214 of certain embodiments provides signals to the logic circuit 210 which the logic circuit 210 uses to control the applied light. The interface 214 can comprise a user interface or an interface to a sensor monitoring at least one parameter of the treatment. In certain such embodiments, the programmable controller 126 is responsive to signals from the sensor to preferably adjust the treatment parameters to optimize the measured response. The programmable controller 126 can thus provide closed-loop monitoring and adjustment of various treatment parameters to optimize the phototherapy. The signals provided by the interface 214 from a user are indicative of parameters that may include, but are not limited to, patient characteristics (e.g., skin type, fat percentage), selected applied power densities, target time intervals, and power density/timing profiles for the applied light.

In certain embodiments, the logic circuit 210 is coupled to a light source driver 220. The light source driver 220 is coupled to a power supply 230, which in certain embodiments comprises a battery and in other embodiments comprises an alternating current source. The light source driver 220 is also coupled to the light source 40. The logic circuit 210 is responsive to the signal from the clock 212 and to user input from the user interface 214 to transmit a control signal to the light source driver 220. In response to the control signal from the logic circuit 210, the light source driver 220 adjust and controls the power applied to the light sources 40. Other control circuits besides the control circuit 200 of FIG. 12 are compatible with embodiments described herein.

In certain embodiments, the logic circuit 110 is responsive to signals from a sensor monitoring at least one parameter of the treatment to control the applied light. For example, certain embodiments comprise a temperature sensor thermally coupled to the scalp 30 to provide information regarding the temperature of the scalp 30 to the logic circuit 210. In such embodiments, the logic circuit 210 is responsive to the information from the temperature sensor to transmit a control signal to the light source driver 220 so as to adjust the parameters of the applied light to maintain the scalp temperature below a predetermined level. Other embodiments include exemplary biomedical sensors including, but not limited to, a blood flow sensor, a blood gas (e.g., oxygenation) sensor, an ATP production sensor, or a cellular activity sensor. Such biomedical sensors can provide real-time feedback information to the logic circuit 210. In certain such embodiments, the logic circuit 110 is responsive to signals from the sensors to preferably adjust the parameters of the applied light to optimize the measured response. The logic circuit 110 can thus provide closed-loop monitoring and adjustment of various parameters of the applied light to optimize the phototherapy.

Figure 13:
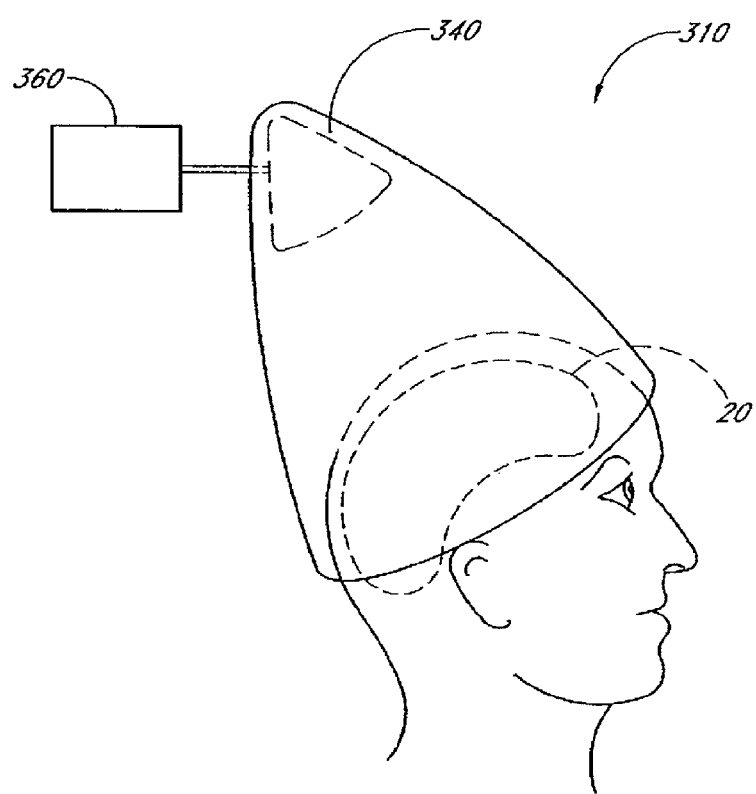
FIG. 13 schematically illustrates a therapy apparatus comprising a light source and a controller.

In certain embodiments, as schematically illustrated in FIG. 13, the therapy apparatus 310 comprises a light source 340 adapted to irradiate a portion of the patient's brain 20 with an efficacious power density and wavelength of light. The therapy apparatus 310 further comprises a controller 360 for energizing said light source 340, so as to selectively produce a plurality of different irradiation patterns on the patient's scalp 30. Each of the irradiation patterns is comprised of a least one illuminated area that is small compared to the patient's scalp 30, and at least one non-illuminated area.

Figure 14:
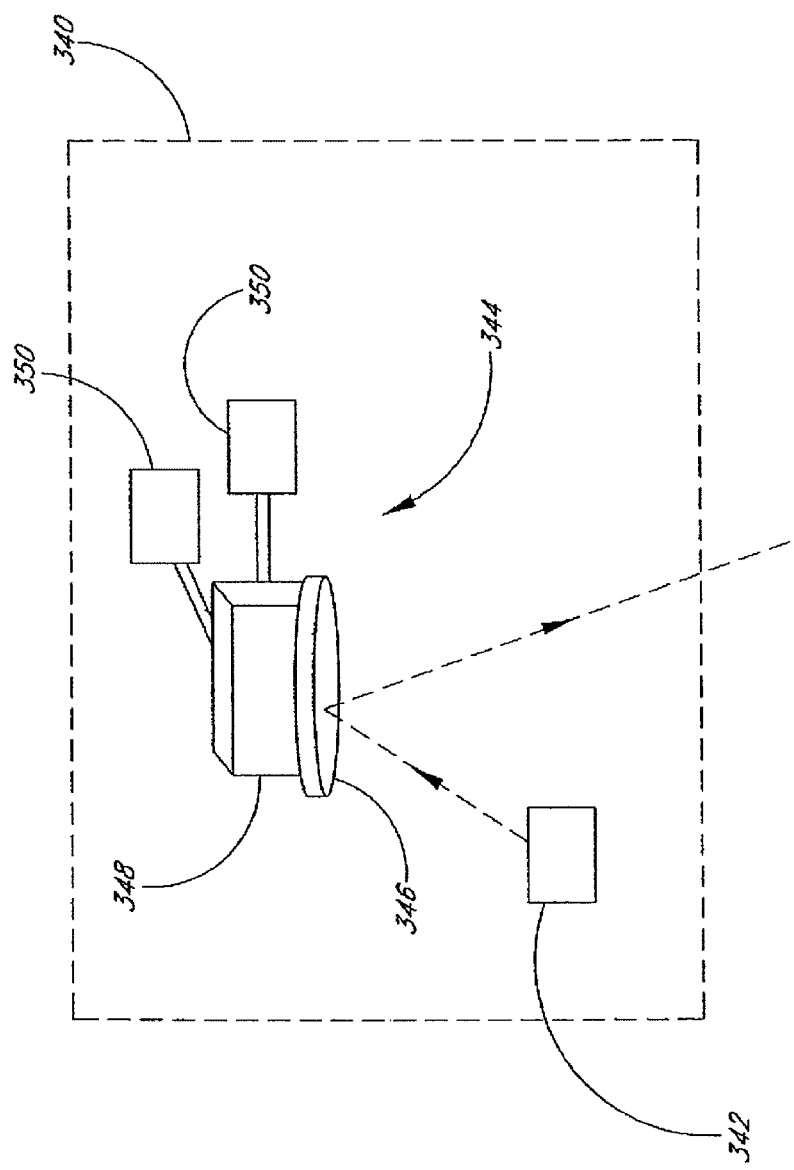
FIG. 14 schematically illustrates a light source comprising a laser diode and a galvometer with a mirror and a plurality of motors.

In certain embodiments, the light source 340 includes an apparatus for adjusting the emitted light to irradiate different portions of the scalp 30. In certain such embodiments, the apparatus physically moves the light source 40 relative to the scalp 30. In other embodiments, the apparatus does not move the light source 40, but redirects the emitted light to different portions of the scalp 30. In an exemplary embodiment, as schematically illustrated in FIG. 14, the light source 340 comprises a laser diode 342 and a galvometer 344, both of which are electrically coupled to the controller 360. The galvometer 344 comprises a mirror 346 mounted onto an assembly 348 which is adjustable by a plurality of motors 350. Light emitted by the laser diode 342 is directed toward the mirror 346 and is reflected to selected portions of the patient's scalp 30 by selectively moving the mirror 346 and selectively activating the laser diode 342. In certain embodiments, the therapy apparatus 310 comprises an element 50 adapted to inhibit temperature increases at the scalp 30 as described herein.

Figure 15A:
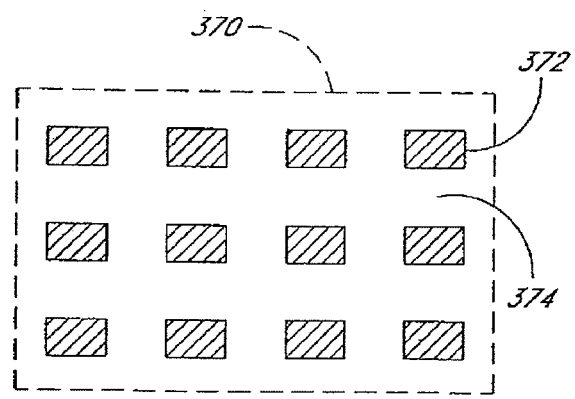
FIGS. 15A and 15B schematically illustrate two irradiation patterns that are spatially shifted relative to each other.

FIG. 15A schematically illustrates an irradiation pattern 370 in accordance with embodiments described herein. The irradiation pattern 370 comprises at least one illuminated area 372 and at least one non-illuminated area 374. In certain embodiments, the irradiation pattern 370 is generated by scanning the mirror 346 so that the light impinges the patient's scalp 30 in the illuminated area 372 but not in the non-illuminated area 374. Certain embodiments modify the illuminated area 372 and the non-illuminated area 374 as a function of time.

Figure 15B:
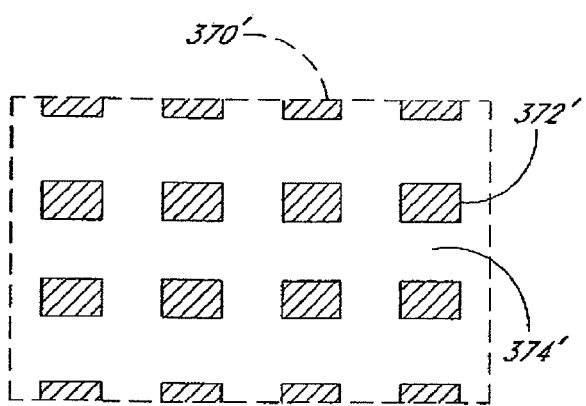

This selective irradiation can be used to reduce the thermal load on particular locations of the scalp 30 by moving the light from one illuminated area 372 to another. For example, by irradiating the scalp 30 with the irradiation pattern 370 schematically illustrated in FIG. 15A, the illuminated areas 372 of the scalp 30 are heated by interaction with the light, and the non-illuminated areas 374 are not heated. By subsequently irradiating the scalp 30 with the complementary irradiation pattern 370' schematically illustrated in FIG. 15B, the previously non-illuminated areas 374 are now illuminated areas 372', and the previously illuminated areas 372 are now non-illuminated areas 374'. A comparison of the illuminated areas 372 of the irradiation pattern 370 of FIG. 15A with the illuminated area 372' of the irradiation pattern 370' of FIG. 15B shows that the illuminated areas 372, 372' do not significantly overlap one another. In this way, the thermal load at the scalp 30 due to the absorption of the light can be distributed across the scalp 30, thereby avoiding unduly heating one or more portions of the scalp 30.

Methods of Light Delivery

Preferred methods of phototherapy are based at least in part on the finding described above that, for a selected wavelength, the power density (light intensity or power per unit area, in $W/cm^2$) or the energy density (energy per unit area, in $J/cm^2$, or power density multiplied by the exposure time) of the light energy delivered to tissue is an important factor in determining the relative efficacy of the phototherapy, and efficacy is not as directly related to the total power or the total energy delivered to the tissue. In the methods described herein, power density or energy density as delivered to a portion of the patient's brain 20, which can include the area of infarct after a stroke, appears to be important factors in using phototherapy to treat and save surviving but endangered neurons in a zone of danger surrounding the infarcted area. Certain embodiments apply optimal power densities or energy densities to the intended target tissue, within acceptable margins of error.

As used herein, the term "neurodegeneration" refers to the process of cell destruction resulting from primary destructive events such as stroke or CVA, as well as from secondary, delayed and progressive destructive mechanisms that are invoked by cells due to the occurrence of the primary destructive event. Primary destructive events include disease processes or physical injury or insult, including stroke, but also include other diseases and conditions such as multiple sclerosis, amyotrophic lateral sclerosis, epilepsy, Alzheimer's disease, dementia resulting from other causes such as AIDS, cerebral ischemia including focal cerebral ischemia, and physical trauma such as crush or compression injury in the CNS, including a crush or compression injury of the brain, spinal cord, nerves or retina, or any acute injury or insult producing neurodegeneration. Secondary destructive mechanisms include any mechanism that leads to the generation and release of neurotoxic molecules, including apoptosis, depletion of cellular energy stores because of changes in mitochondrial membrane permeability, release or failure in the reuptake of excessive glutamate, reperfusion injury, and activity of cytokines and inflammation. Both primary and secondary mechanisms contribute to forming a "zone of danger" for neurons, wherein the neurons in the zone have at least temporarily survived the primary destructive event, but are at risk of dying due to processes having delayed effect.

As used herein, the term "neuroprotection" refers to a therapeutic strategy for slowing or preventing the otherwise irreversible loss of neurons due to neurodegeneration after a primary destructive event, whether the neurodegeneration loss is due to disease mechanisms associated with the primary destructive event or secondary destructive mechanisms.

As used herein, the term "neuroprotective-effective" as used herein refers to a characteristic of an amount of light energy, wherein the amount is a power density of the light energy measured in $mW/cm^2$. A neuroprotective-effective amount of light energy achieves the goal of preventing, avoiding, reducing, or eliminating neurodegeneration.

Thus, a method for the treatment of stroke in a patient in need of such treatment involves delivering a neuroprotective-effective amount of light energy having a wavelength in the visible to near-infrared wavelength range to a target area of the patient's brain 20. In certain embodiments, the target area of the patient's brain 20 includes the area of infarct, i.e. to neurons within the "zone of danger." In other embodiments, the target area includes portions of the brain 20 not within the zone of danger. Without being bound by theory, it is believed that irradiation of healthy tissue in proximity to the zone of danger increases the production of ATP and copper ions in the healthy tissue and which then migrate to the injured cells within the region surrounding the infarct, thereby producing beneficial effects. Additional information regarding the biomedical mechanisms or reactions involved in phototherapy is provided by Tiina I. Karu in "Mechanisms of Low-Power Laser Light Action on Cellular Level", Proceedings of SPIE Vol. 4159 (2000), Effects of Low-Power Light on Biological Systems V, Ed. Rachel Lubart, pp. 1-17, which is incorporated in its entirety by reference herein.

In certain embodiments, delivering the neuroprotective amount of light energy includes selecting a surface power density of the light energy at the scalp 30 corresponding to the predetermined power density at the target area of the brain 20. As described above, light propagating through tissue is scattered and absorbed by the tissue. Calculations of the power density to be applied to the scalp 30 so as to deliver a predetermined power density to the selected target area of the brain 20 preferably take into account the attenuation of the light energy as it propagates through the skin and other tissues, such as bone and brain tissue. Factors known to affect the attenuation of light propagating to the brain 20 from the scalp 30 include, but are not limited to, skin pigmentation, the presence and color of hair over the area to be treated, amount of fat tissue, the presence of bruised tissue, skull thickness, and the location of the target area of the brain 20, particularly the depth of the area relative to the surface of the scalp 30. For example, to obtain a desired power density of 50 $mW/cm^2$ in the brain 20 at a depth of 3 cm below the surface of the scalp 30, phototherapy may utilize an applied power density of 500 $mW/cm^2$. The higher the level of skin pigmentation, the higher the power density applied to the scalp 30 to deliver a predetermined power density of light energy to a subsurface site of the brain 20.

In certain embodiments, treating a patient suffering from the effects of stroke comprises placing the therapy apparatus 10 in contact with the scalp 30 and adjacent the target area of the patient's brain 20. The target area of the patient's brain 20 can be previously identified such as by using standard medical imaging techniques. In certain embodiments, treatment further includes calculating a surface power density at the scalp 30 which corresponds to a preselected power density at the target area of the patient's brain 20. The calculation of certain embodiments includes factors that affect the penetration of the light energy and thus the power density at the target area. These factors include, but are not limited to, the thickness of the patient's skull, type of hair and hair coloration, skin coloration and pigmentation, patient's age, patient's gender, and the distance to the target area within the brain 20. The power density and other parameters of the applied light are then adjusted according to the results of the calculation.

The power density selected to be applied to the target area of the patient's brain 20 depends on a number of factors, including, but not limited to, the wavelength of the applied light, the type of CVA (ischemic or hemorrhagic), and the patient's clinical condition, including the extent of the affected brain area. The power density of light energy to be delivered to the target area of the patient's brain 20 may also be adjusted to be combined with any other therapeutic agent or agents, especially pharmaceutical neuroprotective agents, to achieve the desired biological effect. In such embodiments, the selected power density can also depend on the additional therapeutic agent or agents chosen.

In preferred embodiments, the treatment proceeds continuously for a period of about 10 seconds to about 2 hours, more preferably for a period of about 1 to about 10 minutes, and most preferably for a period of about 1 to 5 minutes. In other embodiments, the light energy is preferably delivered for at least one treatment period of at least about five minutes, and more preferably for at least one treatment period of at least ten minutes. The light energy can be pulsed during the treatment period or the light energy can be continuously applied during the treatment period.

In certain embodiments, the treatment may be terminated after one treatment period, while in other embodiments, the treatment may be repeated for at least two treatment periods. The time between subsequent treatment periods is preferably at least about five minutes, more preferably at least about 1 to 2 days, and most preferably at least about one week. In certain embodiments in which treatment is performed over the course of multiple days, the apparatus 10 is wearable over multiple concurrent days (e.g., embodiments of FIGS. 1, 3, 9A, 10, and 13). The length of treatment time and frequency of treatment periods can depend on several factors, including the functional recovery of the patient and the results of imaging analysis of the infarct. In certain embodiments, one or more treatment parameters can be adjusted in response to a feedback signal from a device (e.g., magnetic resonance imaging) monitoring the patient.

During the treatment, the light energy may be continuously provided, or it may be pulsed. If the light is pulsed, the pulses are preferably at least about 10 nanosecond long and occur at a frequency of up to about 100 kHz. Continuous wave light may also be used.

The thrombolytic therapies currently in use for treatment of stroke are typically begun within a few hours of the stroke. However, many hours often pass before a person who has suffered a stroke receives medical treatment, so the short time limit for initiating thrombolytic therapy excludes many patients from treatment. In contrast, phototherapy treatment of stroke appears to be more effective if treatment begins no earlier than several hours after the ischemic event has occurred. Consequently, the present methods of phototherapy may be used to treat a greater percentage of stroke patients.

In certain embodiments, a method provides a neuroprotective effect in a patient that had an ischemic event in the brain. The method comprises identifying a patient who has experienced an ischemic event in the brain. The method further comprises estimating the time of the ischemic event. The method further comprises commencing administration of a neuroprotective effective amount of light energy to the brain. The administration of the light energy is commenced no less than about two hours following the time of the ischemic event. In certain embodiments, phototherapy treatment can be efficaciously performed preferably within 24 hours after the ischemic event occurs, and more preferably no earlier than two hours following the ischemic event, still more preferably no earlier than three hours following the ischemic event, and most preferably no earlier than five hours following the ischemic event. In certain embodiments, one or more of the treatment parameters can be varied depending on the amount of time that has elapsed since the ischemic event.

Without being bound by theory, it is believed that the benefit in delaying treatment occurs because of the time needed for induction of ATP production, and/or the possible induction of angiogenesis in the region surrounding the infarct. Thus, in accordance with one preferred embodiment, the phototherapy for the treatment of stroke occurs preferably about 6 to 24 hours after the onset of stroke symptoms, more preferably about 12 to 24 hours after the onset of symptoms. It is believed, however, that if treatment begins after about 2 days, its effectiveness will be greatly reduced.

Example

An in vitro experiment was done to demonstrate one effect of phototherapy on neurons, namely the effect on ATP production. Normal Human Neural Progenitor (NHNP) cells were obtained cryopreserved through Clonetics of Baltimore, Md., catalog # CC-2599. The NHNP cells were thawed and cultured on polyethyleneimine (PEI) with reagents provided with the cells, following the manufacturers' instructions. The cells were plated into 96 well plates (black plastic with clear bottoms, Becton Dickinson of Franklin Lakes, N.J.) as spheroids and allowed to differentiate into mature neurons over a period of two weeks.

A Photo Dosing Assembly (PDA) was used to provide precisely metered doses of laser light to the NHNP cells in the 96 well plates. The PDA included a Nikon Diaphot inverted microscope (Nikon of Melville, N.Y.) with a LUDL motorized x,y,z stage (Ludl Electronic Products of Hawthorne, N.Y.). An 808 nanometer laser was routed into the rear epi-fluorescent port on the microscope using a custom designed adapter and a fiber optic cable. Diffusing lenses were mounted in the path of the beam to create a "speckled" pattern, which was intended to mimic in vivo conditions after a laser beam passed through human skin. The beam diverged to a 25 millimeter diameter circle when it reached the bottom of the 96 well plates. This dimension was chosen so that a cluster of four adjacent wells could be lased at the same time. Cells were plated in a pattern such that a total of 12 clusters could be lased per 96 well plate. Stage positioning was controlled by a Silicon Graphics workstation and laser timing was performed by hand using a digital timer. The measured power density passing through the plate for the NHNP cells was 50 mW/cm$^2$.

Two independent assays were used to measure the effects of 808 nanometer laser light on the NHNP cells. The first was the CellTiter-Glo Luminescent Cell Viability Assay (Promega of Madison, Wis.). This assay generates a "glow-type" luminescent signal produced by a luciferase reaction with cellular ATP. The CellTiter-Glo reagent is added in an amount equal to the volume of media in the well and results in cell lysis followed by a sustained luminescent reaction that was measured using a Reporter luminometer (Turner Biosystems of Sunnyvale, Calif.). Amounts of ATP present in the NHNP cells were quantified in Relative Luminescent Units (RLUs) by the luminometer.

The second assay used was the alamarBlue assay (Biosource of Camarillo, Calif.). The internal environment of a proliferating cell is more reduced than that of a non-proliferating cell. Specifically, the ratios of NADPH/NADP, FADH/FAD, FMNH/FMN and NADH/NAD, increase during proliferation. Laser irradiation is also thought to have an effect on these ratios. Compounds such as alamarBlue are reduced by these metabolic intermediates and can be used to monitor cellular states. The oxidization of alamarBlue is accompanied by a measurable shift in color. In its unoxidized state, alamarBlue appears blue; when oxidized, the color changes to red. To quantify this shift, a 340PC microplate reading spectrophotometer (Molecular Devices of Sunnyvale, Calif.) was used to measure the absorbance of a well containing NHNP cells, media and alamarBlue diluted 10% v/v. The absorbance of each well was measured at 570 nanometers and 600 nanometers and the percent reduction of alamarBlue was calculated using an equation provided by the manufacturer.

The two metrics described above, (RLUs and % Reduction) were then used to compare NHNP culture wells that had been lased with 50 mW/cm$^2$ at a wavelength of 808 nanometers. For the CellTiter-Glo assay, 20 wells were lased for 1 second and compared to an unlased control group of 20 wells. The CellTiter-Glo reagent was added 10 minutes after lasing completed and the plate was read after the cells had lysed and the luciferase reaction had stabilized. The average RLUs measured for the control wells was 3808+/−3394 while the laser group showed a two-fold increase in ATP content to 7513+/−6109. The standard deviations were somewhat high due to the relatively small number of NHNP cells in the wells (approximately 100 per well from visual observation), but a student's unpaired t-test was performed on the data with a resulting p-value of 0.02 indicating that the two-fold change is statistically significant.

The alamarBlue assay was performed with a higher cell density and a lasing time of 5 seconds. The plating density (calculated to be between 7,500-26,000 cells per well based on the certificate of analysis provided by the manufacturer) was difficult to determine since some of the cells had remained in the spheroids and had not completely differentiated. Wells from the same plate can still be compared though, since plating conditions were identical. The alamarBlue was added immediately after lasing and the absorbance was measured 9.5 hours later. The average measured values for percent reduction were 22%+/−7.3% for the 8 lased wells and 12.4%+/−5.9% for the 3 unlased control wells (p-value=0.076). These alamarBlue results support the earlier findings in that they show a similar positive effect of the laser treatment on the cells.

Increases in cellular ATP concentration and a more reduced state within the cell are both related to cellular metabolism and are considered to be indications that the cell is viable and healthy. These results are novel and significant in that they show the positive effects of laser irradiation on cellular metabolism in in-vitro neuronal cell cultures.

In certain embodiments, the phototherapy is combined with other types of non-light energy treatments for an improved therapeutic effect. Treatment can comprise directing light through the scalp of the patient to a target area of the brain concurrently with applying an electromagnetic field to the brain. In such embodiments, the light has an efficacious power density at the target area and the electromagnetic field has an efficacious field strength. For example, the apparatus 50 (refer to FIG. 1) can also include systems for delivering electromagnetic treatment 44, e.g., as described in U.S. Pat. No. 6,042,531 issued to Holcomb, which is incorporated in its entirety by reference herein. In certain embodiments, the electromagnetic field comprises a magnetic field, while in other embodiments, the electromagnetic field comprises a radio-frequency (RF) field. As another example, treatment can comprise directing an efficacious power density of light through the scalp of the patient to a target area of the brain concurrently with applying an efficacious amount of ultrasonic energy to the brain. For example, the apparatus 50 can include systems for delivering ultrasonic treatment 46, e.g., as described in U.S. Pat. No. 5,054,470 issued to Fry et al., which is incorporated in its entirety by reference herein.

The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the invention.

What is claimed is:

1. A method of treating one or more disorders of a patient's brain, the method comprising:
   placing an apparatus adjacent to a scalp of the patient, the apparatus comprising a plurality of light sources, the plurality of light sources having irradiances that overlap with one another, thereby reducing areas of increased temperature at the scalp;
   applying an energy delivery profile such that light propagates from the light source to at least a portion of the patient's brain, the light having a wavelength and a peak irradiance between 10 mW/cm2 and 10 W/cm2 at the scalp;
   detecting a temperature of the scalp when the energy delivery profile is being applied using a temperature sensor thermally coupled to the scalp; and
   adjusting one or more parameters of the energy delivery profile based on the detected temperature of the scalp to reduce the temperature of the scalp,
   wherein the energy delivery profile is adjusted based on the temperature of the scalp such that the peak irradiance of the light is decreased,
   wherein the one or more disorders is selected from the group consisting of stroke, multiple sclerosis, amyotrophic lateral sclerosis, epilepsy, Alzheimer's disease, dementia, and traumatic brain injury.

2. The method of claim 1, wherein said light source is configured to generate light with the wavelength between 780 nm and 840 nm.

3. The method of claim 1, further comprising placing a magnetic energy source adjacent to the scalp and activating the magnetic energy source such that an electromagnetic field is applied to the patient's brain.

4. The method of claim 1, wherein the energy delivery profile is adjusted to maintain the temperature of the scalp below a predetermined level.

5. The method of claim 3, wherein the light source and the magnetic energy source are concurrently active.

6. A method of treating one or more disorders of a patient's brain, the method comprising:
   placing an apparatus adjacent to a scalp of the patient, the apparatus comprising a plurality of light sources, the plurality of light sources having irradiances that overlap with one another, thereby reducing areas of increased temperature at the scalp;
   applying an energy delivery profile such that light propagates from the light source to at least a portion of the patient's brain, the light having a wavelength and a peak irradiance between 10 mW/cm2 and 10 W/cm2 at the scalp;
   detecting a biomedical parameter of the patient using a biomedical sensor, the biomedical parameter selected from an ATP production level of at least a portion of the patient's brain or a cellular activity level of at least a portion of the patient's brain; and
   adjusting one or more parameters of the energy delivery profile based on the detected biomedical parameter to cause the biomedical parameter to be adjusted towards a desired level,
   wherein the energy delivery profile is adjusted based on the biomedical parameter such that the peak irradiance of the light is increased,
   wherein the one or more disorders is selected from the group consisting of stroke, multiple sclerosis, amyotrophic lateral sclerosis, epilepsy, Alzheimer's disease, dementia, and traumatic brain injury.

7. The method of claim 6, further comprising placing an ultrasonic treatment system adjacent to the scalp and activating the ultrasonic treatment system such that ultrasonic energy is applied to the patient's brain, wherein the light source and the ultrasonic energy are concurrently active.

8. The method of claim 6, further comprising placing an electromagnetic treatment system adjacent to the scalp and activating the electromagnetic treatment system such that an electromagnetic field is applied to the patient's brain, wherein the light source and the electromagnetic field are concurrently active.

9. The method of claim 6, further comprising placing a radio frequency treatment system adjacent to the scalp and activating the radio frequency treatment system such that a radio frequency (RF) field is applied to the patient's brain, wherein the light source and the RF field are concurrently active.

10. The method of claim 6, further comprising placing a non-light energy source adjacent to the scalp and activating the non-light energy source, wherein the light source and the non-light energy source are concurrently active.

11. The method of claim 6, wherein the light has an irradiance between 0.01 mW/cm$^2$ and 100 mW/cm$^2$ at a depth of 2 centimeters below the patient's dura.

12. The method of claim 6, wherein the light has a target time interval and the energy delivery profile is adjusted based on the detected biomedical parameter such that the target time interval is altered.

13. The method of claim 6, wherein the light has an irradiation pattern and the energy delivery profile is adjusted based on the biomedical parameter such that the irradiation pattern is altered.

14. The method of claim 6, wherein the wavelength is between 780 nm and 840 nm.

* * * * *